(12) United States Patent
Leen et al.

(10) Patent No.: US 9,963,677 B2
(45) Date of Patent: May 8, 2018

(54) GENERATION OF CTL LINES WITH SPECIFICITY AGAINST MULTIPLE TUMOR ANTIGENS OR MULTIPLE VIRUSES

(75) Inventors: Ann M. Leen, Bellaire, TX (US); Ulrike Gerdemann, Houston, TX (US); Cliona M. Rooney, Bellaire, TX (US); Juan Vera, Bellaire, TX (US); John R. Wilson, New Brighton, MN (US)

(73) Assignees: Baylor College of Medicine, Houston, TX (US); Wilson Wolf Manufacturing, New Brighton, MN (US)

( * ) Notice: Subject to any disclaimer, the term of this patent is extended or adjusted under 35 U.S.C. 154(b) by 6 days.

(21) Appl. No.: 12/862,409

(22) Filed: Aug. 24, 2010

(65) Prior Publication Data

US 2011/0182870 A1 Jul. 28, 2011

Related U.S. Application Data

(60) Provisional application No. 61/236,261, filed on Aug. 24, 2009.

(51) Int. Cl.
| | |
|---|---|
| *A61K 38/00* | (2006.01) |
| *C12N 5/00* | (2006.01) |
| *C12N 5/02* | (2006.01) |
| *C12N 5/0783* | (2010.01) |
| *A61K 39/12* | (2006.01) |
| *A61K 39/155* | (2006.01) |
| *A61K 39/245* | (2006.01) |
| *A61K 39/00* | (2006.01) |

(52) U.S. Cl.
CPC ........ *C12N 5/0638* (2013.01); *A61K 39/0011* (2013.01); *A61K 39/12* (2013.01); *A61K 39/155* (2013.01); *A61K 39/245* (2013.01); *C12N 5/0636* (2013.01); *A61K 2039/5158* (2013.01); *A61K 2039/54* (2013.01); *A61K 2039/572* (2013.01); *C12N 2501/23* (2013.01); *C12N 2501/2302* (2013.01); *C12N 2501/2306* (2013.01); *C12N 2501/2307* (2013.01); *C12N 2501/2312* (2013.01); *C12N 2501/2315* (2013.01); *C12N 2502/11* (2013.01)

(58) Field of Classification Search
None
See application file for complete search history.

(56) References Cited

U.S. PATENT DOCUMENTS

| | | | | |
|---|---|---|---|---|
| 5,641,628 | A | 6/1997 | Bianchi | 435/6 |
| 6,274,378 | B1 * | 8/2001 | Steinman et al. | 435/377 |
| 6,455,299 | B1 * | 9/2002 | Steinman et al. | 435/235.1 |
| 6,821,778 | B1 * | 11/2004 | Engleman et al. | 435/372.3 |
| 7,785,875 | B2 * | 8/2010 | Hwang et al. | 435/320.1 |
| 2004/0022761 | A1 | 2/2004 | Banchereau et al. | 424/85.2 |
| 2005/0106717 | A1 * | 5/2005 | Wilson et al. | 435/297.5 |
| 2006/0045883 | A1 | 3/2006 | Molldrem et al. | 424/185.1 |
| 2006/0073126 | A1 | 4/2006 | Shiku et al. | 424/93.21 |
| 2008/0260701 | A1 | 10/2008 | Hope | 424/93.7 |
| 2009/0305324 | A1 | 12/2009 | Kuzushima et al. | |
| 2011/0182870 | A1 | 7/2011 | Leen et al. | |
| 2016/0362658 | A1 | 12/2016 | Leen et al. | |

FOREIGN PATENT DOCUMENTS

| | | | |
|---|---|---|---|
| WO | WO 2005028505 | * | 3/2005 |
| WO | WO 2007/121276 | | 10/2007 |
| WO | WO-2008073313 A2 | | 6/2008 |
| WO | 2009053109 A | | 4/2009 |
| WO | 2011028531 A1 | | 3/2011 |
| WO | 2013088147 A1 | | 6/2013 |

OTHER PUBLICATIONS

Bensussan et al. "Detection of membrane-bound HLA-G translated products with a specific monoclonal antibody," *Proc. Natl. Acad. Sci. USA*, 92:10292-10296, 1995.
Can and Karahuseyinoglu, "Concise review: human umbilical cord stroma with regard to the source of fetus-derived stem cells," *Stem Cells*, 25:2886-2895, 2007.
PCT International Preliminary Report on Patentability issued in International Application No. PCT/US2010/025209, mailed Sep. 9, 2011.
PCT International Search Report issued in International Application No. PCT/US2010/025209, mailed Jul. 14, 2010.
International Search Report and Written Opinion issued in International Application No. PCT/US2010/46505, mailed Oct. 14, 2010.
Leen et al., "Cytotoxic lymphocyte (CTL) therapy for the treatment of EBV negative tumors," Abstract, International Society for Cell and Gene Therapy of Cancer Annual Meeting held in Cork, Ireland, presented Sep. 4, 2009.
Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Nov. 2008.
Leen et al., "Identification of hexon-specific CD4 and CD8 T-cell epitopes for vaccine and immunotherapy," *Journal of Virology*, 82(1):546-554, 2008.
Kedl, Ross M. et al; "T Cells Down-Modulate Peptide-MHC Complexes on APCs in vivo"; Published online: Dec. 3, 2001, DOI: 10.1038/ni/742; 2002 Nature Publishing Group.
Kedl, Ross M. et al; "T Cells Compete for Antigen-bearing Antigen-presenting Cells"; J.P. Med.—The Rockfeller University Press—vol. 192, No. 8, Oct. 16, 2002.
Gerdemann, Ulrike, et al; "Nucleofection of DCs to Generate Multivirus-specific T Cells for Prevention or Treatment of Viral Infections in the Immunocompromised Host"; Molecular Therapy, Jul. 7, 2009, vol. 17, No. 9, pp. 1616-1625.

(Continued)

*Primary Examiner* — Michail Belyavskyi
(74) *Attorney, Agent, or Firm* — Norton Rose Fulbright US LLP

(57) ABSTRACT

The present invention encompasses methods and compositions for the generation and use of cytotoxic T lymphocytes that target multiple viruses or that are specific for multiple tumor antigens. In specific embodiments, the generation methods employ use of certain cytokines to promote proliferation and reduce cell death in an activated T cell population and/or that employ a particular bioreactor having a gas permeable membrane.

28 Claims, 19 Drawing Sheets

(56) References Cited

OTHER PUBLICATIONS

Vera, Juan F., et al; "Accelerated Production of Antigen-Specific T-cells for Pre-Clinical and Clinical Applications using Gas-Permeable Rapid Expansion Cultureware (G-Rex)"; Journal of Immunotherapy, Apr. 2010, vol. 33, No. 3, pp. 305-315.
Gerdemann, et al; "Multivirus-Specific CTL for Adoptive Transfer Using In Vitro Pepmix Stimulation", Biology Blood Marrow Transplant, online Jan. 28, 2011, p. S216.
Bensussan et al. "Detection of membrane-bound HLA-G translated products with a specific monoclonal antibody", Proc. Natl. Acad. Sci. USA, 92:10292-10296, 1995.
Can and Karahuseyinoglu, "Concise review: human umbilical cord stroma with regard to the source of fetus-derived stem cells", Stem Cells, 25:2886-2895, 2007.
Dunne et al., "Selective Expansion and Partial Activation of Human NK Cells and NK Receptor-Positive T Cells by Il-2 and IL-15", Journal of Immunology, 2001, pp. 3129-3138.
Gerdemann et al., "Generation of Multivirus-specific T Cellls to Prevent/treat Viral Infections aftr Allogeneic Hematopoietic Stem Cell Transplant", Journal of Visualized Experiments, May 2011, vol. 51, e2736, pp. 1-6.
Gerdemann et al., "Rapidly Generated Multivirus-specific Cytotoxic T Lymphocytes for the Prophylaxis and Treatment of Viral Infections", Molecular Therapy 2012, vol. 20, No. 8, pp. 1622-1632.
Gerdemann et al., "Multivirus-specific CTL for adoptive transfer using in vitro pepmix stimulation", Biology Blood Marrow Transplant., Feb. 1, 2011, pp. S216.
Gerdemann et al., "Cytotoxic T lymphocytes simultaneously targeting multiple tumor-associates antigens to treat EBV negative lymphoma", Molecular Therapy, Nature Publishing Group, GB, vol. 19, No. 12, Dec. 1, 2011, pp. 2258-2268.
Gerdemann et al., "Safety and clinical efficacy of rapidly-generated trivirus-directed T cells as treatment for adenovirus, EBV, and CMV infections after allogeneic hematopoietic stem cell transplant", Molecular Therapy, vol. 2, No. 11, Jun. 20, 2013, pp. 2112-2121.
Hobeika et al., "Detailed analysis of cytomegalovirus (CMV)-specific T cells expanded for adoptive immunotherapy of CMV infection following allogeneic stem cell transplantation for malignant disease", Intl. Society for cellular Therapy, Cytotherapy, 2008, vol. 10, No. 3, pp. 289-302.
Jennes et al., "Enhanced ELISPOT detection of antigen-specific T cell responses from cryopreserved specimens with addition of both IL-7 and IL-15 the Amplispot assay" Journal of Immunological Methods, 2002, vol. 270, pp. 99-108.
Lapteva and Vera " Optimization Manufacture of Virus- and Tumor-Specific T Cells", Stem Cells International, Apr. 26, 2011, vol. 2011, pp. 1-8.
Montes et al., "Optimum in vitro expansion of human antigen-specific CD8+ T cells for adoptive transfer therapy", British Society for Immunology, Clinical and Experimental Immunology, 2005, vol. 142, pp. 292-302.
Na et al., "Human Bone Marrow as a Source of Multifunctional CMV-Specific CD4+ T Cells for Adoptive Cell Therapy" Blood, 2007, vol. 110, p. 2973.
Trivedi et al., "Generation of CMV-specific T lymphocytes using protein-spanning pools of pp65-derived overlapping pentadecapeptides for adoptive immunotherapy", Blood, Apr. 1, 2005, vol. 105, No. 7, pp. 2793-2794.
van Montfoort et al., "Antigen storage compartments in mature dendritic cells facilitate prolonged cytotoxic T lymphocyte cross-priming capacity", PNAS, Apr. 21, 2009, vol. 106, No. 16, pp. 6730-6735.
Vella et al., "Cytokine-induced survival of activated T cells in vitro and in vivo", Proc. Natl. Acad. Sci. USA 95, Immunology, Mar. 1998, vol. 95, pp. 3810-3815.
Y E Z, et al; In Vitro expansion and Charcterization of Dendritic Cells Derived from Human Bon Marroe CD34+ Cells; Bone Marrow Transpaln, 1996, v 18. 997-1008.
International Preliminary Report on Patentablility dated Feb. 10, 2014, during prosecution of International Application No. PCT/GB2012/053113.
International Search Report on Patentablility dated Mar. 26, 2013, during prosecution of International Application No. PCT/GB2012/053113.
Leen et al., "Overcoming antigenic competition to produce multispecific cytotoxic T lymphocyte lines for adoptive transfer", American Society for Blood and Marrow Transplantation, Feb. 2009, No. 374, p. 134.
Ramaswami et al., Clin Vaccine Immunol, Published on line Mar. 2, 2011, vol. 18, No. 5 815-824.
Suneetha et al., Journal of Immunological Methods, 2009, vol. 342, No. 1-2, pp. 33-48.
Leen et al., Nature Medicine, 2006, vol. 12, No. 10, pp. 1160-1166.
Blyth et al., in Blood, (Nov. 20, 2009) vol. 114, No. 22, pp. 962, Meeting Info.: 51st Annual Meeting of the American-Society-of-Hematology, New Orleans, LA, USA. Dec. 5-8, 2009, Amer Soc Hematol.
Binggeli et al., American Journal of Transplantation, 2007, vol. 7, pp. 1131-1139.
Chakera et al., Clin Exp. Immunol2011, Sep. 156 (3): 401-409.
Khanna et al., Blood, Jul. 2011, vol. 118, No. 4, pp. 1121-1131.
Maecker et al., Journal of Immunological Methods, 2001, vol. 55, pp. 27-40.
Nair et al, "Induction of tumor-specific cyototoxic T lymphocytes in cancer patients by autologous tumor RNA-transfected dendritic cells", Annals of Surgery, Apr. 1, 2002, vol. 235, No. 4, pp. 540-549.
Liao et al., "Transfection of RNA encoding tumor antigens following maturation of dendritic cells leads to prolonged presentation of antigen and the generation of high-affinity tumor-reactive cytotoxic T lymphocytes", Molecular Therapy, May 1, 2004, vol. 9, No. 5, pp. 757-764.
Morandi et al., "Tumor mRNA-Transfected Dendritic Cells: Stimulate the Generation of CTL that Recognize Neuroblastoma-Associated Antigens, Kill Tumor Cells: Immunotherapeutic Implications", Neoplasia, Oct. 1, 2006, vol. 8, No. 10, pp. 833-842.

* cited by examiner

Lymphoma CTL

| Donor | SSX2 | MAGE 4 | Survivin |
|-------|------|--------|----------|
| No 1  | X    |        |          |
| No 2  | X    | X      | X        |
| No 3  | X    | X      | X        |
| No 4  | X    | X      | X        |
| No 5  | X    | X      |          |
| No 6  |      | X      | X        |
| No 7  |      | X      | X        |

Leukemia CTL

| Donor | PRAME | Survivin | PR3 | WT-1 |
|-------|-------|----------|-----|------|
| No 1  | X     |          |     |      |
| No 2  | X     |          | X   | X    |
| No 3  | X     | X        |     |      |
| No 4  | X     |          | X   | X    |
| No 5  | X     | X        |     | X    |

FIG. 14

SFG – IL7Rα  Vera et al, Mol Ther 2009
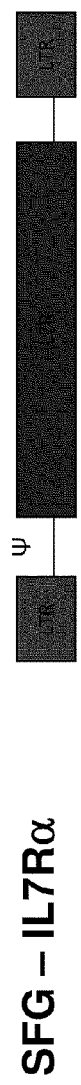
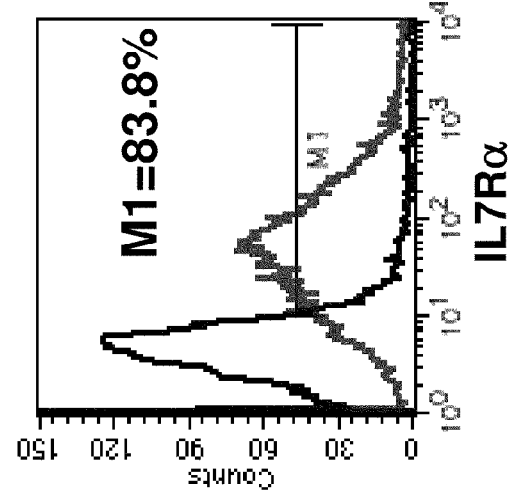
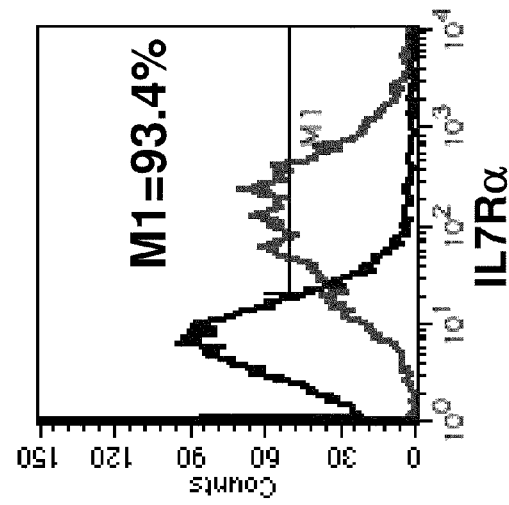
FIG. 15

GENERATION OF CTL LINES WITH SPECIFICITY AGAINST MULTIPLE TUMOR ANTIGENS OR MULTIPLE VIRUSES

CROSS-REFERENCE TO RELATED APPLICATIONS

The present invention claims priority to U.S. Provisional Patent Application Ser. No. 61/236,261, filed Aug. 24, 2009, which is incorporated by reference herein in its entirety.

STATEMENT REGARDING FEDERALLY SPONSORED RESEARCH OR DEVELOPMENT

This invention was made with government support under P50 CA126752 awarded by NIH-NCI. The government has certain rights in the invention.

TECHNICAL FIELD

The present invention generally concerns the fields of cell biology, immunology, molecular biology, and medicine. In particular embodiments, the invention generally concerns immunotherapy for cancer.

BACKGROUND OF THE INVENTION

Multivirus-specific T Cells for Prevention and/or Treatment of Viral Infections in the Immunocompromised Host Viral infections account for substantial morbidity and mortality in the immunocompromised host, for example patients who have received allogeneic stem cell transplantation (SCT). Infections caused by persistent herpesviruses such as Epstein-Barr virus (EBV), cytomegalovirus (CMV), and herpes simplex virus, as well as by respiratory viruses such as respiratory syncytial virus, parainfluenza, and influenza are well known, whereas the importance of infections caused by adenovirus (Adv), BK virus, and human herpesvirus-6 have more recently been appreciated (Kim et al., 2007; Myers et al., 2007; Kadakia et al., 1996; Comoli et al., 2006; de Pagter et al., 2008). Although pharmacological agents are standard therapy for some infections, they have substantial toxicities, generate resistant variants, and are frequently ineffective.

Immunotherapeutic strategies to restore virus-specific immunity offer an attractive treatment alternative. Donor-derived EBV-specific cytotoxic T lymphocytes (CTLs) have been prepared using EBV-transformed lymphoblastoid cell lines (EBVLCLs) as a source of antigen, and infusion of these lines prevented and treated EBV-driven B cell lymphoproliferative diseases (EBV-LPDs) after allogeneic hematopoietic SCT (HSCT) (Heslop et al., 1996; Comoli et al., 2007) (Heslop et al., 2010) with minimal toxicity (Cruz et al, 2010).

Similarly, adoptively-transferred donor-derived CMV-specific CTL generated using CMV peptides, lysate, or vector-transduced antigen-presenting cells (APCs) were able to reconstitute immune responses against this virus and protect patients against the development of CMV disease or late recurrences (Riddell et al., 1992; Walter et al., 1995; Einsele et al., 2002a; Einsele et al., 2002b; Peggs et al., 2003; Micklethwaite et al., 2008; Micklethwaite et al., 2007). More recently, trivirus-reactive CTL targeting EBV, CMV, and Adv were produced by genetically modifying monocytes and EBV-LCL with a chimeric adenoviral vector expressing CMV-pp65 as a transgene.

As few as $2 \times 10^5$/kg trivirus-specific CTL proliferated by several logs after infusion into HSCT recipients and appeared to protect the recipients against disease produced by all three viruses (Leen et al., 2006). Despite these encouraging clinical results, the broader implementation of T-cell immunotherapy is limited by (i) the infectious virus material (EBV/CMV/Adv) generally required for CTL generation, (ii) the expense of manufacture of clinical grade vectors for antigen presentation, and (iii) the prolonged period of culture (10-12-week manufacturing process) that is required to eliminate alloreactive T cells, with its attendant demands on technical skill and time. To address this latter problem, some groups have evaluated more rapid approaches for antigen-specific T-cell selection.

Cobbold and colleagues selected CMV-specific CD8+ T cells from the blood of stem cell transplant donors using human leukocyte antigen (HLA)-peptide tetramers followed by selection with magnetic beads, and saw impressive clinical responses with eight of nine treated patients clearing their infection following infusion of tiny numbers of selected cells (median $8.6 \times 10^3$/kg) (Cobbold et al., 2005). Selection of T cells that secrete interferon-γ (IFN-γ) after exposure to antigen (the IFN-γ capture assay) has also been used clinically by Feuchtinger and colleagues, who specifically selected Adv-specific T cells directly from peripheral blood after in vitro stimulation with viral peptides and showed that small numbers of cells ($1.2-50 \times 10^3$/kg) were safe, protective, and effective in vivo (Feuchtinger et al., 2004; Feuchtinger et al., 2006). However, both these approaches are expensive and require a large starting blood volume, which is not always available, particularly in the matched unrelated donor setting. Tetramer reagents are limited already known epitopes and to CD8 selection. Gamma capture limits the infusions to T cells that secrete gamma interferon. Antigen-specific T cells with other functions may be lost So far, their use has been limited to restricted cases of urgent medical need.

The art needs an alternative good manufacturing practice-compliant method that overcomes all three limitations (volume, time, and infectious agents) to allow the rapid generation of multivirus-specific CTL from small blood volumes for immunotherapeutic purposes. The present invention provides how dendritic cells (DCs) can be nucleofected with DNA plasmids encoding a range of immunodominant and subdominant viral antigens and used as in vitro T-cell stimulators to generate multivirus-reactive CTLs that target multiple different epitopes in antigens from multiple common viruses within 10 days (Gerdemann et al., 2009).

Multi-Tumor Associated Antigen (TAA) T Cells for Prevention and/or Treatment of Cancer For example, EBV is associated with Hodgkin's and non-Hodgkin's lymphoma and nasopharyngeal carcinoma. In these cases, the tumor cells express three of about 90 Epstein-Barr viral antigens. To optimize the antigenic targeting of CTLs, our group has prepared CTLs whose specificity was directed towards the three expressed viral antigens by sequentially using dendritic cells (DCs) and then EBV-LCL genetically modified to overexpress LMP1 and LMP2 (two of the three antigens) to reactivate and expand LMP-specific CTLs from patients or their HLA-matched allogeneic donors. The LMP antigens were expressed from an adenoviral vector. In HL and NHL the clinical results were encouraging, and 16 of 17 patients treated in remission of high-risk HL remained in remission, while 12/15 patients with active relapsed disease had tumor responses. However, >70% of the patients referred to our studies have EBV negative lymphomas and are not eligible for EBV antigen-specific T cells.

One of the challenges of adoptive immunotherapy for non-viral cancers remains the identification of strongly immunogenic target antigens. The model tumor antigens should be specifically and universally expressed on tumor cells in order to limit collateral damage, and ideally should be essential for the maintenance of the oncogenic phenotype of the tumor. However, the majority of antigens do not meet these criteria since they are not necessarily neo-antigens uniquely present in cancer cells but rather antigens that are also expressed in normal cells and against which peripheral blood T cells are tolerized or deleted. However antigens that are essentially tumor-specific have been identified, but the pattern of tumor antigens expressed is highly tumor type-dependent. This underscores the importance of identifying appropriate antigens that are not expressed or poorly expressed on normal tissues and of optimizing cell culture conditions for tumor-specific CTL production, to overcome the mechanisms that establish T cell tolerance against "self" antigens.

T cell immunotherapies for non-viral tumor antigen have been described, with promising clinical results in some studies. Rosenberg and colleagues reported that infusion of melanoma-specific tumor-infiltrating lymphocytes (TILs) together with high-dose interleukin 2 (IL-2) produced clinical responses in approx. 35% of patients with metastatic melanoma. The specificity of the infused cells was not analyzed but it is likely that they targeted multiple epitopes/tumor associated antigens. More promising results were subsequently achieved using a modified treatment protocol which incorporated a lymphodepletion step prior to CTL infusion, in order to improve the expansion and persistence of adoptively-transferred cells. Ninety three patients with metastatic melanoma refractory to standard therapies received immunodepleting chemotherapy−/+total body irradiation followed by the adoptive transfer of highly selected, TIL-derived, tumor-reactive T cells and high-dose IL-2 (720,000 IU/kg q 8 h to tolerance). Fifty two of the 93 patients had objective clinical responses to treatment (39 PR, 12 CR), including regression of large bulky tumors. However, the collection of autologous TILs is not possible for most tumors. Furthermore the in vitro expansion of large numbers of tumor-specific T cells (>1010 CTL) is a complex and expensive procedure. The same group also infused T cell clones directed targeting a single epitope in the melanoma-associated antigen, gp100+/−IL-2 but reported poor clinical responses, with only one minor response and one mixed response, and showed that the cells failed to engraft or persist in vivo. These studies demonstrate the potential of adoptively-transferred antigen-specific T cells to eliminate cancer, but highlights the importance of targeting multiple epitopes/antigens to produce optimal clinical results.

BRIEF SUMMARY OF THE INVENTION

The present invention relates to the production of CTLs that either multiple tumor antigens or that target multiple pathogens (including viruses or bacteria, for example). The CTLs are more rapidly generated than conventional methods because of novel improvements provided herein. Such improvements include at least the use of the source of the antigens being from particular types of vectors (for example, plasmids) or particular libraries of peptides. Other improvements include the use of certain cytokines and cell culture environments in the cell proliferation media.

In specific embodiments, the present invention provides methods to produce multivirus-specific CTLs for treating individuals with multiple virus infections (such as those having multiple virus infections post allogeneic stem cell transplant) or individuals with cancer having particular tumor-associated antigens. In embodiments of both multivirus and tumor-associated antigen cases, the source of the antigen may be either plasmids or peptide libraries. In embodiments of both multivirus and tumor-associated antigen cases, the CTLs may be cultured in vessels having gas permeable membrane. In specific embodiments of the multivirus embodiments, the culture medium comprises IL4 and IL7. In specific embodiments of the tumor-associated antigen embodiments, the culture medium comprises IL-7, IL12, IL15 and either IL6 or IL27.

In certain embodiments, the present invention describes the generation of multivirus CTL lines or multi-TAA CTL lines. For multivirus CTL generation, dendritic cells may be pulsed with pepmixes spanning the viral antigens or DCs may be nucleofected with plasmids encoding the viral antigens to produce antigen-presenting cells (APCs). Alternatively, PBMCs can be stimulated directly with pepmixes to activate antigen-specific cells. These strategies obviate the need to use adenovirus vectors and EBV-transformed APCs (LCLs). For multi-TAA CTL generation, DCs may be pulsed with pepmixes spanning the target antigen or DCs may be nucleofected with plasmids encoding at least part of the tumor antigens. Additional embodiments include the use of a certain cytokine(s) that act to promote proliferation and reduce cell death in the activated T-cell population, and use of cell culture in a bioreactor, such as a G-Rex bioreactor, to promote optimal T-cell expansion in vitro.

Multivirus-Specific T Cells for Viral Infections

In particular aspects of the invention, there is a rapid and effective method to generate multivirus-specific CTL with broad epitope reactivity. The invention in particular cases can be applied to the generation of CTL with "broad spectrum" specificity that could be generated using plasmids encoding immunodominant and protective antigens derived from a variety of viruses or other pathogens.

In some embodiments of the invention, there is preparation and/or administration of multivirus-specific CTLs for the prophylaxis and/or treatment of infection in an immunocompromised individual (solid organ transplantation, HIV infection, chemotherapy, genetic immunodeficiency). Although the individual may be immunocompromised for any reason, in specific cases the individual is post allogeneic stem cell transplant. The viral infection may be of any kind(s), although in specific embodiments it is EBV, CMV, Adenovirus, BK, HHV6, RSV, Influenza, Parainfluenza, Bocavirus, Coronavirus, LCMV, Mumps, Measles, Metapneumovirus, Parvovirus B, Rotavirus, and West Nile Virus.

In certain embodiments related to multivirus-specific CTLs, the present invention utilizes a certain cytokine combination of IL-4 and IL-7 that acts to promote proliferation and reduce cell death in the activated T-cell population.

In certain aspects, multivirus-specific CTLs are developed using the following plasmids that express exemplary viral proteins: (i) Adenovirus hexon and/or penton; (ii) Cytomegalovirus (CMV) immediate early 1 (IE1) and/or pp65; and (iii) Epstein Barr virus (EBV) EBNA1, LMP2, and/or BZLF1. In particular embodiments, the broad spectrum CTLs incorporate all of the expression vectors used to make tri-virus specific cells, plus, in specific embodiments, additional plasmids that express, for example, the following viral proteins: (i) BK polyoma virus large T antigen and/or VP1;

and/or (ii) Human herpesvirus-6 (HHV-6) immediate early 1 (IE1) and/or tegument proteins U90, U11, U14, and/or U71; and/or (iii) Respiratory Syncytial Virus (RSV) F, M and/or N proteins; and/or (iv) Parainfluenza virus (PIV) F, HN, and/or NP proteins.

In some embodiments of the invention, there is a method for generating donor-derived multivirus-specific cytotoxic T-cells to treat and/or prevent viral infection and/or reactivation in a subject in need of such treatment, comprising at least one or more of the following steps: (i) isolation of peripheral blood mononuclear cells (PBMCs) from a donor; (ii) generation of antigen-presenting cells (APCs) called dendritic cells from the PBMCs by selecting for the ability to adhere to a cell culture substrate, followed by culture in medium containing GM-CSF and IL4; (ii) separate nucleofection of DCs with plasmid DNA expression vectors that encode at least one viral protein from at least two viruses as follows: (a) an expression plasmid encoding the immunodominant adenovirus antigens hexon and penton; (b) Cytomegalovirus (CMV) immediate early 1 (IE1) and pp65; (c) Epstein Barr virus (EBV) EBNA1, LMP1, and BZFL1; (d) BK polyoma virus large T antigen and VP1; (e) Human herpesvirus-6 (HHV-6) immediate early 1 (IE1) and tegument proteins U90, U11, U14, and U71; (f) Respiratory Syncytial Virus (RSV) F, M, and NP proteins; (g) Parainfluenza virus (PIV) F, HN, and NP proteins; (iii) co-culturing the nucleofected DCs with T-cells retained from the non-adherent PBMC fraction; (iv) culturing the stimulated T-cells in medium that contains added IL7+IL4, for a period ranging from 9-12 days; (v) expanding the CTL in the G-Rex device to support optimal expansion; and (vi) verifying the antigen specificity and lack of alloreactivity of the stimulated T-cells.

To use T cells to target tumors, which are not virus associated and arise in immunocompetent individuals, non viral tumor-expressed antigens can be targeted. These antigens, which are expressed or overexpressed on tumor cells include SURVIVIN, PRAME, NY-ESO-1, MAGE-A4, SSX2, and SSX4 (as examples), which are commonly expressed in HL and NHL and are targets for antigen-specific T cells, in particular embodiments. To this end the inventors have developed protocols to generate polyclonal CTL lines with simultaneous specificity against multiple tumor antigens using DCs pulsed with a mastermix of pepmixes spanning for example SSX2, Survivin, and MAGEA4 to prime both CD4+ and CD8+ T cells tumor-specific T cells. This strategy of targeting multiple antigens simultaneously should maximize CTL efficacy and minimize tumor immune escape. For in vitro expansion the inventors defined an optimized cytokine cocktail to promote maximum specific proliferation while preserving the multi-specificity of the lines. The resultant CTL were functional in vitro and produced IFNγ and TNFα when stimulated with TAA pepmixes in ELIspot and intracellular cytokine assays, and specifically lysed pepmix-pulsed and whole antigen-expressing target cells in traditional $Cr^{51}$ release assays. The inventors successfully generated TAA-CTL from PBMCs isolated from heavily pretreated HL patients that were able to lyse autologous tumor material.

Multitumor-Associated Antigen-Specific T Cells for Cancer

In certain embodiments of the invention, CTLs are developed that target TAA that are highly expressed on tumor cells, including, for example, MAGE1, 3, PRAME, and NY-ESO-1, for example (see below).

In certain embodiments the present invention concerns CTL therapy for the treatment of particular tumors, including EBV negative tumors.

In specific embodiments, the present invention concerns generation of CTLs for multiple tumor antigens. Although the invention may be utilized for any cancer, including lung, breast, brain, stomach, ovarian, pancreatic, kidney, liver, bone, cervical, uterine, testicular, prostate, head and neck tumors, and so forth, in certain embodiments the invention is utilized for cancers associated with blood and bone marrow.

In specific embodiments of the invention, the CTL product is designed to specifically correspond to the antigenic expression pattern exhibited by the individual's tumor. Thus, given that one can now nucleofect multiple antigen expression vectors into DCs provides a route by which a single CTL product is generated that responds to the unique antigenic signature of an individual's tumor.

To this end the inventors have developed an approach to generate CTL lines reactive against multiple tumor antigens simultaneously by stimulation with dendritic cells pulsed with pepmixes spanning the antigens of interest as a stimulus in the presence of the cytokine cocktail IL7, 12, 15 and either IL6 or IL27 for the first 9 days, which the inventors have shown to be essential for generating CTL lines with multi-antigen specificity (FIG. 14). Subsequently, the CTL are restimulated using DCs pulsed with the same pepmixes and cultured in IL7 and IL2.

In certain embodiments of the invention, there is a method of generating cytotoxic T-lymphocytes (CTLs) that target at least one antigen from two or more viruses, comprising the steps of nucleofecting a population of dendritic cells (DCs) from an individual with a plurality of plasmids, wherein each plasmid in the plurality encodes at least one antigen from one of the two or more viruses, and thereby producing a population of dendritic cells that expresses and presents at least one antigen from two or more viruses; contacting peripheral blood mononuclear cells (PBMC) from the individual with the nucleofected DCs (APCs) to produce a population of antigen-specific T lymphocytes that are capable of responding to at least one antigen from two or more viruses; and culturing the antigen-specific T lymphocytes in medium in a vessel that has a gas permeable membrane, wherein components of medium comprise IL-4 and IL-7, to produce cytotoxic T-lymphocytes (CTLs) that target at least one antigen from two or more viruses. In specific embodiments, the CTLs are administered to an immunocompromised individual. In some cases, the individual has had allogeneic stem cell transplant. In particular cases, the viruses are selected from the group consisting of EBV, CMV, Adenovirus, BK, HHV6, RSV, Influenza, Parainfluenza, Bocavirus, Coronavirus, LCMV, Mumps, Measles, Metapneumovirus, Parvovirus B, Rotavirus, West Nile Virus, and a combination thereof. In specific embodiments, the cells are administered by injection, such as by intravenous injection.

In certain embodiments, there is a method of generating cytotoxic T-lymphocytes (CTLs) that target at least one antigen from two or more viruses, comprising the steps of either (1) nucleofecting a population of dendritic cells (DCs) from an individual with a plurality of plasmids, wherein each plasmid in the plurality encodes at least one antigen from one of the two or more viruses, and thereby producing a population of dendritic cells that expresses and presents at least one antigen from two or more viruses; or (2) contacting a population of DCs from an individual with a library of peptides, wherein the peptides overlap in sequence to span part or all of an entire viral antigen, thereby producing a population of DCs (APCs) that present at least one epitope from two or more different antigens; and contacting peripheral blood mononuclear cells (PBMC) from the individual with the nucleofected DCs (APCs) to produce a population of antigen-specific T lymphocytes that are capable of responding to at least one antigen from two or more viruses; and culturing the antigen-specific T lymphocytes in medium in a vessel that has a gas permeable membrane, wherein components of medium comprise IL-4 and IL-7, to produce cytotoxic T-lymphocytes (CTLs) that target at least one antigen from two or more viruses.

In some embodiments, there is a method of generating cytotoxic T-lymphocytes (CTLs) that target two or more tumor antigens, comprising the steps of either (1) nucleofecting a population of DCs from an individual with a plurality of plasmids, wherein each plasmid in the plurality encodes at least one epitope of one or more tumor antigens, thereby producing a population of DCs (APCs) that express and present at least one epitope from two or more tumor antigens; or (2) contacting a population of DCs from an individual with a library of peptides, wherein the peptides overlap in sequence to span part or all of an entire antigen, thereby producing a population of DCs (APCs) that present at least one epitope from two or more different antigens; and contacting peripheral blood mononuclear cells (PBMCs) from the individual with the APCs to produce a population of antigen specific T lymphocytes that are capable of responding to at least one epitope from two or more tumor antigens; and culturing the T-lymphocytes in medium in a vessel that has a gas permeable membrane, wherein the components of the medium comprise IL-7, IL12, IL15 and either IL6 or IL27. In specific embodiments, the individual has lymphoma or leukemia. In certain embodiments, the T-lymphocytes are administered to the individual, such as by injection, including by intravenous injection.

BRIEF DESCRIPTION OF THE DRAWINGS

FIG. 14 illustrates that CTL lines show simultaneous specificity for two or more antigens.

FIG. 15 shows that tumor CTLs can be transduced with a transgenic IL7 receptor.

DETAILED DESCRIPTION OF THE INVENTION

Figure 1:
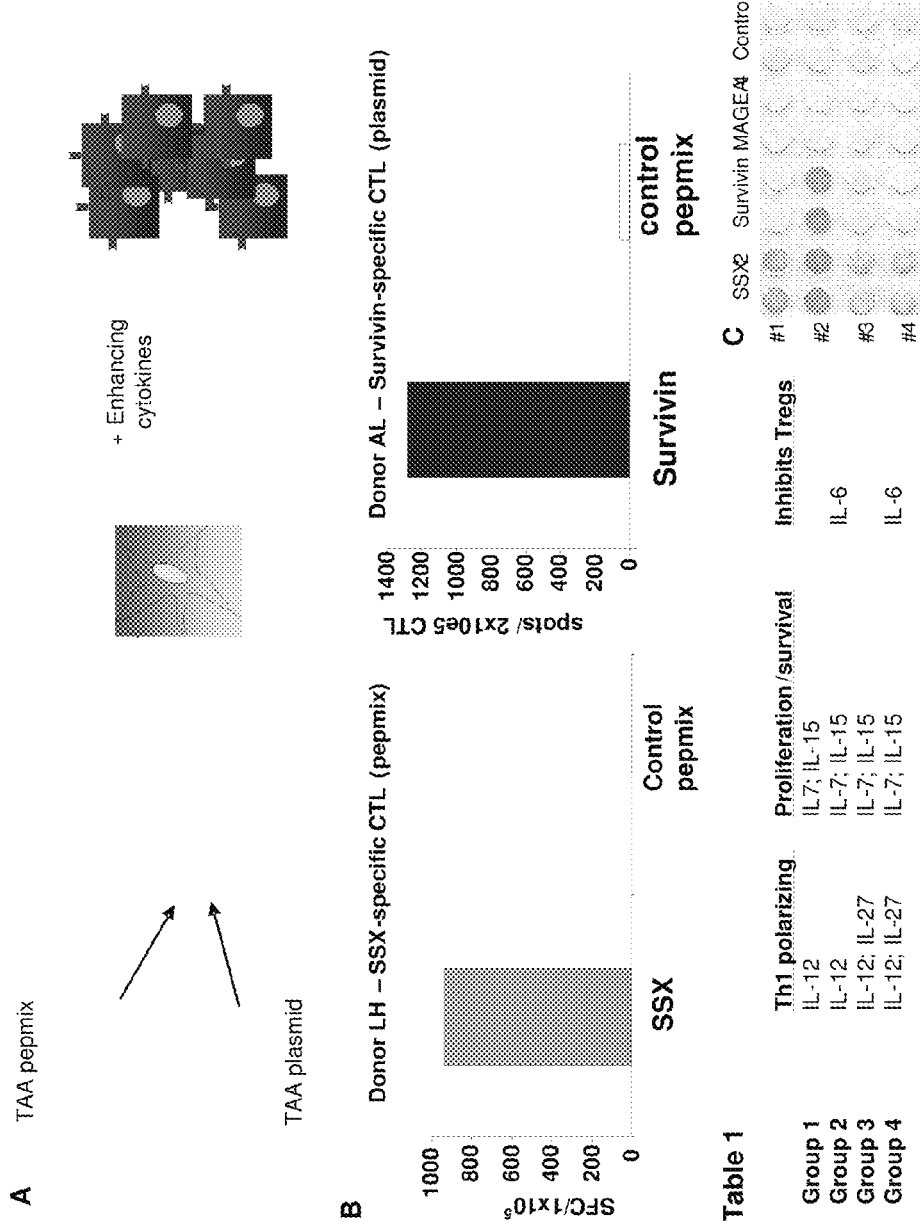
FIGS. 1A-1C show generation of TA-specific CTL lines in healthy donors. (A) CTL were generated using either pepmix-pulsed or plasmid transfected DCs as APCs, and CTL were cultured in the presence of combinations of enhancing cytokines, such as those shown in Table 1. (B) IFN-γ ELIspot analysis of CTL lines generated using either pepmix (left panel) or DNA plasmids (right panel) as a source of antigen. (C) The cytokine combination IL7, IL12, IL15, and IL6 produced multivirus-specific CTL with simultaneous specificity against SSX2, Survivin, and MAGE-A4, for example, as measured by IFN-γ ELIspot.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

U.S. Provisional Patent Application 61/267,761, "Culture Method for More Efficient Production of Cells", filed Dec. 8, 2009, and U.S. patent application Ser. No. 10/961,814, filed Oct. 8, 2004, are both incorporated by reference herein in their entirety.

I. General Embodiments Of The Invention

The present invention concerns the generation of CTLs that target multiple pathogens (including viruses or bacteria, for example) or that target multiple tumor antigens. The CTLs are produced more rapidly than conventional methods by employing improvements provided by the invention. The improvements include the use of particular types of vectors or particular libraries of peptides as a source of the antigens, and the use of certain cytokines in the cell proliferation media and the use of specialized cell culture equipment to support optimal cell culture proliferation and expansion.

In particular, the present invention provides methods to produce multivirus-specific CTLs for treating individuals with multiple virus infections (such as those having multiple virus infections post allogeneic stem cell transplant) or individuals with cancer having particular tumor-associated antigens. In embodiments of both multivirus and tumor-associated antigen cases, the source of the antigen may be either plasmids or peptide libraries. In embodiments of both cases, the CTLs may be cultured in vessels having gas permeable membrane. In specific embodiments of the multivirus embodiments, the culture medium comprises IL4 and IL7. In specific embodiments of the tumor-associated antigen embodiments, the culture medium comprises IL-7, IL12, IL15 and either IL6 or IL27.

II. Exemplary Cell Culture Equipment And Reagents

In certain embodiments of the invention, any cells are cultured under conditions to facilitate proliferation of the desired cells. In particular cases, the cells are cultured under conditions as described in U.S. Provisional Patent Application 61/267,761, "Culture Method for More Efficient Production of Cells", filed Dec. 8, 2009, and U.S. patent application Ser. No. 10/961,814, filed Oct. 8, 2004, which are both incorporated by reference herein in their entirety. In specific embodiments of the invention, cells are cultured in a gas permeable cell culture device. In certain cases, the cell culture equipment allows T cells to proliferate to higher densities while dramatically reducing manipulations on the part of a cell culture technician. In some embodiments, the device has a gas permeable bottom that permits cells to gravitate to the bottom to access oxygen via the gas permeable bottom.

In certain embodiments of the invention, there is utilized a gas permeable cell culture device comprising a top and a bottom joined by a plurality of sides, wherein the bottom comprises a gas permeable material and at least a portion of a side is comprised of a gas permeable material such that cells can be cultured when the apparatus is oriented in at least two positions, vertically and horizontally. In particular embodiments, there are gas permeable devices and methods are disclosed for cell culture, including cell culture devices and methods that contain medium at heights and certain gas permeable surface area to medium volume ratios. These devices and methods allow improvements in cell culture efficiency and scale up efficiency.

Certain embodiments disclosed herein provide more efficient cell culture devices and methods that overcome the limitations of prior devices and methods by creating gas permeable devices that can integrate a variety of novel attributes. These various attributes include gas exchange without reliance upon a gas/liquid interface, increased medium height, reduced gas permeable surface area to medium volume ratios, gas exchange through the device, side walls, cell support scaffolds that are comprised of traditional materials, and increased gas permeable material thickness. In particular embodiments, with gas permeable devices comprised of a lower gas permeable material it is beneficial to increase medium height beyond that dictated by conventional wisdom or allowed in commercially available devices such that convection of substrates within cell culture medium plays a role Reducing the ratio of gas permeable surface area to medium volume to a ratio not contemplated in prior cell culture devices or methods can also increase culture efficiency. It allows an increase in medium height without a corresponding increase in device length or width. In the preferred embodiments, provisions are made that allow either medium height to increase or the ratio of gas permeable surface area to medium volume to decrease. Provisions can also be made that allow both the medium height to increase and the ratio of gas permeable surface area to medium volume to decrease.

If it is the design objective to reduce the gas permeable surface area to medium volume ratio relative to conventional wisdom, a wide variety of embodiments for gas permeable devices and methods are possible. They can take the form of prior devices, or entirely new forms. If the form is a gas permeable petri dish up below 50 mm in diameter, the gas permeable surface area to medium volume ratio should preferably be below 2.74 $cm^2$/ml. If the form is a gas permeable petri dish 50 mm or greater in diameter, the gas permeable surface area to medium volume ratio should preferably be below 1.96 $cm^2$/ml. If the form is a multiple well tissue culture plate with 384 wells or more, the gas permeable surface area to medium volume ratio should preferably be below 1.10 $cm^2$/ml; less than 24 wells to less than 384 wells, the gas permeable surface area to medium volume ratio should preferably be below 1.03 $cm^2$/ml; 24 wells or less, the gas permeable surface area to medium volume ratio should preferably be below 0.97 $cm^2$/ml. If the form is a gas permeable cartridge in which two sides of the cartridge are gas permeable, the surface area to medium volume ratio should preferably be below 0.79 $cm^2$/ml. If in the form of a cell culture bag, the gas permeable surface area to medium volume ratio should preferably be below 1.0 $cm^2$/ml. If the form is a compartmentalized device, and all medium in the device resides entirely above the semi-permeable membrane, the gas permeable surface area to medium volume ratio should preferably be below 1.74 $cm^2$/ml. If the form is a compartmentalized device, and all medium in the device does not reside entirely above the semi-permeable membrane, the gas permeable surface area to medium volume ratio should preferably be below 0.31 $cm^2$/ml.

The lower gas permeable material can be any membrane, film, or material used for gas permeable cell culture devices, such as silicone, fluoroethylenepolypropylene, polyolefin, and ethylene vinyl acetate copolymer. A wide range of sources for learning about gas permeable materials and their use in cell culture can be used for additional guidance, including co-pending U.S. patent application Ser. No. 10/460,850 incorporated herein in its entirety. The use of the words film and membrane imply a very thin distance across the gas permeable material, and the inventors have found that the embodiments of this invention function when the gas permeable material of the described devices and methods is beyond the thickness associated with films and membranes. Therefore, the portion of the device that contributes to gas exchange of the culture is called a gas permeable material herein. Those skilled in the art will recognize that the gas permeable material should be selected based on a variety of characteristics including gas permeability, moisture vapor transmission, capacity to be altered for desired cell interaction with cells, optical clarity, physical strength, and the like. A wide variety of information exists that describe the types of gas permeable materials that have been successfully used for cell culture. Silicone is often a good choice. It has excellent oxygen permeability, can allow optical observation, is not easily punctured, typically does not bind the cells to it, and can be easily fabricated into a wide variety of shapes. If silicone is used, it may be less than about 0.2 inches, about 0.1 inches, about 0.05 inches, or about 0.030 inches in the areas where gas transfer is desired.

The height of walls of the device plays an important role in device scale up efficiency. An object of this invention is to provide for increased medium height, thereby increasing device efficiency. The height of the walls can dictate how much medium is allowed to reside in the device. Adding medium provides a larger source of substrates and a larger sink for waste products. By increasing wall height when more medium is needed during scale up, the geometry of the device is more compatible with the shape of incubators, flow hoods, and biohazard disposal bags. Furthermore, the increase in volume relative to the surface area upon which cells reside can allow more medium per cell to be present. That can have the effect of reducing feeding frequency, thereby reducing labor and contamination risk. It can also have the effect of increasing the number of cells residing per square centimeter of device footprint. Structuring walls to allow an increase in medium volume can also have the beneficial effect of diminishing the effects of medium evaporation.

In a certain embodiment, walls are capable of allowing medium to reside at a height that exceeds that of devices that rely upon a gas/liquid interface and more preferably exceeds that of typical static gas permeable devices. For example, the height of wall is beyond 3 mm, and in some cases beyond 2.0 cm, and will thus provide advantages. By providing users of the device the option of adding more medium to the device than prior gas permeable devices, many advantages accrue including the ability to house more cells per device, feed the device less frequently, and scale the device up without increasing the footprint. Walls can be comprised of any biocompatible material and should mate to lower gas permeable material in a manner that forms a liquid tight seal. The methods of mating a lower gas permeable material to walls include adhesive bonding, heat sealing, compression squeeze, and any other method commonly used for generating seals between parts. As an option, walls and lower gas permeable material can be formed of the same material and fabricated as a single entity.

In certain embodiments, there is a multiple well tissue culture device, such as a plate, having multiple wells each composed of a well bottom comprising a gas permeable material and the well sidewalls exceed a certain height, for example exceed 5 mm, 7 mm, 9 mm, 10 mm, 10.5 mm, 10.7 mm, 10.9 mm, 11 mm, 11.1 mm, 11.5 mm, 12 mm, 13 mm, 14 mm, 15 mm, 16 mm, 16.5 mm, 17 mm, 18 mm, and so forth. In specific embodiments, the ratio of surface area of gas permeable material to the volume of a cell culture compartment (such as a well bottom and sidewall(s)) is less than a particular size, for example, less than 3, 2, 1, 0.58, 0.94, 0.91, $cm^2/ml$.

In particular embodiments, there a gas permeable cartridge is employed in the invention, wherein the cartridge is comprised of a lower wall comprised of a gas permeable material, an upper wall, wherein the lower and upper walls are affixed to an intermediate sidewall forming a cell culture compartment, wherein the intermediate sidewall exceeds 0.5 cm, 0.75 cm, 0.9 cm, 1.0 cm, 1.2 cm, 1.27 cm, 1.3 cm, 1.4 cm, 1.5 cm, and 1.6 cm in height.

In certain cases, there is a gas permeable cell culture device employed in the invention consisting essentially of a static cell culture container, wherein the cell culture container includes a top, a bottom, and a sidewall, wherein at least the bottom is comprised at least in part of non-porous gas permeable material, the bottom not being curved, an access port to the cell culture container, and at least a portion of the sidewall residing at a height greater than a certain amount from the surface of the bottom, for example, greater than 3 cm, 4 cm, 5 cm, 5.2 cm, 6 cm, 7 cm, and so forth.

In some embodiments, there is a gas permeable cell culture device comprising a static cell culture container, wherein the cell culture container includes a top, a bottom, and a sidewall, wherein at least the bottom is comprised at least in part of non-porous gas permeable material, the bottom not being curved, an access port to the cell culture container, and not including mixing equipment, wherein the sidewall is not interrupted by the access port at least below a height of a certain amount (for example, 1 cm, 1.5 cm, 2.0 cm, 2.5 cm, 2.6 cm, 2.7 cm, 2.8 cm, 3.0 cm, and so forth) from the bottom when the top is not comprised entirely of gas permeable material or at least beyond a height of a certain amount (for example, 1.5 cm, 1.7 cm. 1.8 cm, 1.9 cm, 2.0 cm, 2.1 cm, 2.2 cm, 2.3 cm, and so forth) from the bottom when the top is comprised entirely of gas permeable material.

In some embodiments of the invention, there includes a method of culturing cells including forming a cell culture container that includes a gas permeable bottom; and adding cell culture medium and seeding cells of a predetermined cell type and of a predetermined quantity in the cell culture container such that the cell type and cell culture medium reside in the cell culture container; and allowing the predetermined quantity of cells to gravitate to the gas permeable bottom in order to establish a first cell surface density, the first cell surface density defined as cells per square centimeter of container surface area upon which they reside at the seeding stage of cell culture; and the first cell surface density, when normalized to $cells/cm^2$, being less than the first cell surface density that has been established by conventional methods for culturing the given cell type when cultured in flasks or multiple well plates, and not mixing the cell culture medium and allowing the cell type to grow to a second cell surface density; and the second cell surface density being greater than the maximum attainable cell surface density of conventional methods.

For multivirus CTL generation, one may employ a ratio of DCs:PBMCs of 1:10-20. Cells may be cultured in a G-Rex40 in a volume of 30 ml of medium+IL4+IL7. On days 5-7 cells will be counted and if there are $>5\times10^7$ cells the culture will be split 1:1 and few with fresh media, in certain embodiments.

III. Tumor Antigens

In embodiments wherein multiTAA-specific CTL are employed for the treatment and/or prevention of cancer, a variety of TAA may be targeted. Tumor antigens are substances produced in tumor cells that trigger an immune response in a host.

Exemplary tumor antigens include at least the following: carcinoembryonic antigen (CEA) for bowel cancers; CA-125 for ovarian cancer; MUC-1 or epithelial tumor antigen (ETA) or CA15-3 for breast cancer; tyrosinase or melanoma-associated antigen (MAGE) for malignant melanoma; and abnormal products of ras, p53 for a variety of types of tumors; alphafetoprotein for hepatoma, ovarian, or testicular cancer; beta subunit of hCG for men with testicular cancer; prostate specific antigen for prostate cancer; beta 2 microglobulin for multiple myelom and in some lymphomas; CA19-9 for colorectal, bile duct, and pancreatic cancer; chromogranin A for lung and prostate cancer; TA90 for melanoma, soft tissue sarcomas, and breast, colon, and lung cancer. Examples of tumor antigens are known in the art, for example in Cheever et al., 2009, which is incorporated by reference herein in its entirety.

Specific examples of tumor antigens include at least CEA, MHC, CTLA-4, gp100, mesothelin, PD-L1, TRP1, CD40, EGFP, Her2, TCR alpha, trp2, TCR, MUC1, cdr2, ras, 4-1BB, CT26, GITR, OX40, TGF-β. WT1, MUC1, LMP2, HPV E6 E7, EGFRvIII, HER-2/neu, MAGE A3, p53 non-mutant, NY-ESO-1, PSMA, GD2, Melan A/MART1, Ras mutant, gp 100, p53 mutant, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1, for example.

IV. Generation Of Pepmix Libraries

Pepmixes utilized in the invention may be from commercially available peptide libraries made up of peptides that are 15 amino acids long and overlapping one another by 11 amino acids, in certain aspects. Examples include those from JPT technologies or Miltenyi. In particular embodiments, the peptides are 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example, and there is overlap of 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length.

V. Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

DNA methyltransferase inhibitors and/or histone deacetylase inhibitors. Exemplary DNA methyltransferase inhibitors include, for example, 5-azacytidine, 5-aza-2'-deoxycytidine, 1-beta-D-arabinofuranosyl-5-azacytosine and dihydro-5-azacytidine. Exemplary HDAC inhibitors include hydroxamic acids, such as trichostatin A; cyclic tetrapeptides (such as trapoxin B), and the depsipeptides; benzamides; electrophilic ketones; and the aliphatic acid compounds such as phenylbutyrate and valproic acid.

VI. Examples

The following examples are presented in order to more fully illustrate the preferred embodiments of the invention. They should in no way, however, be construed as limiting the broad scope of the invention.

A. Multivirus-Specific CTLS

Figure 3:
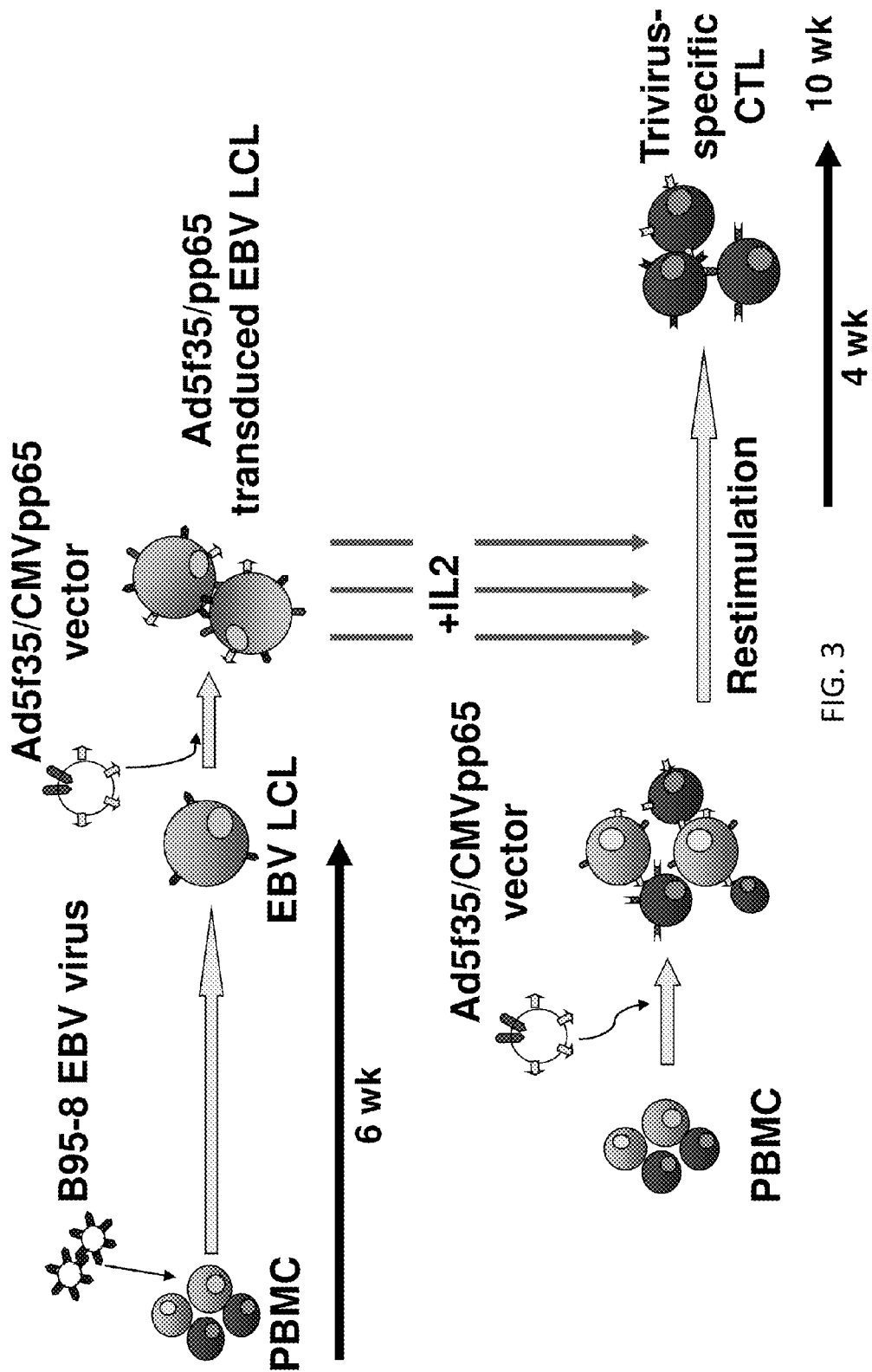
FIG. 3 shows production of trivirus-specific CTL by previous methods in the art.
Figure 4:
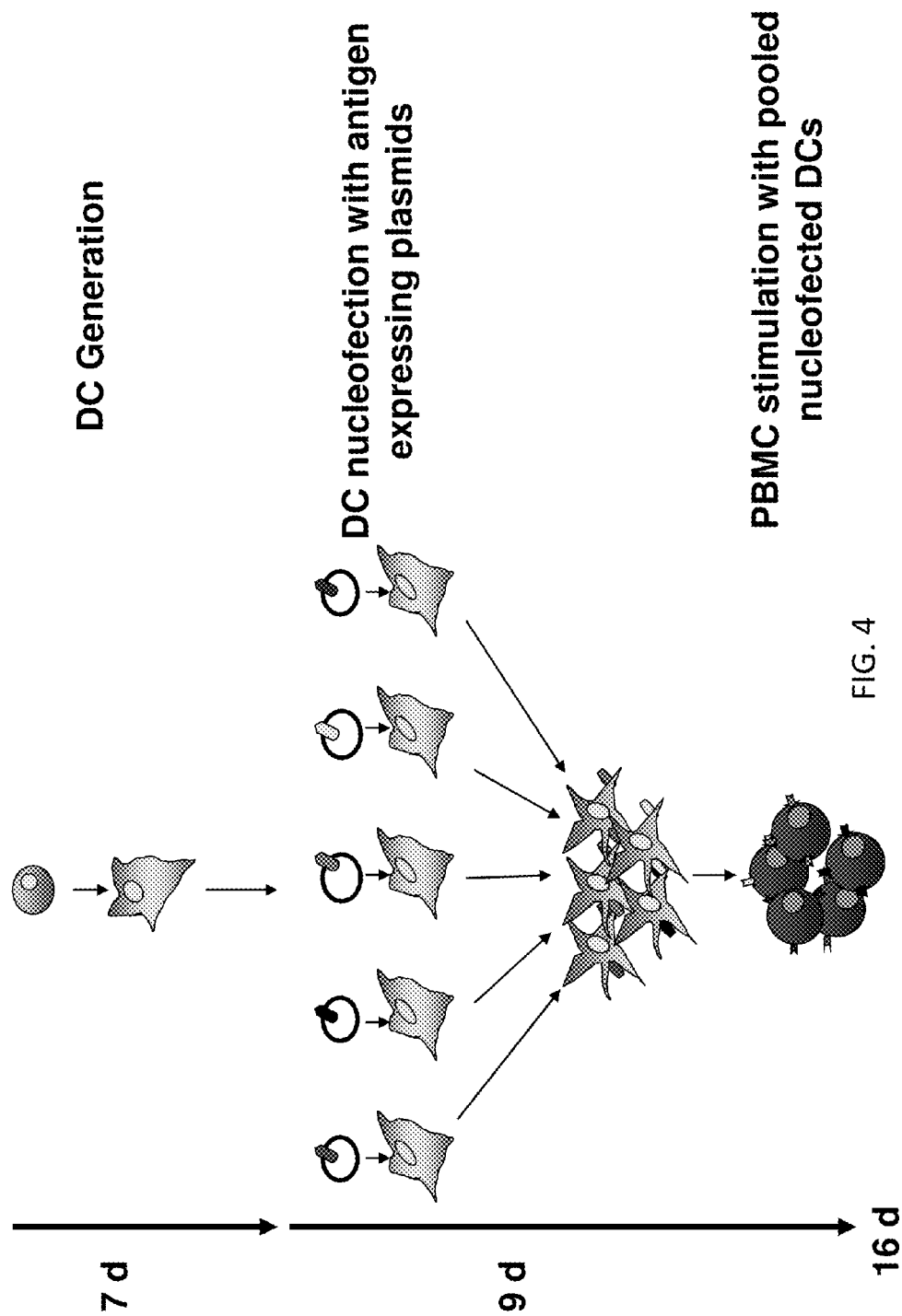
FIG. 4 illustrates exemplary generation of multivirus-specific CTL pursuant to at least certain methods of the invention.
Figure 5:
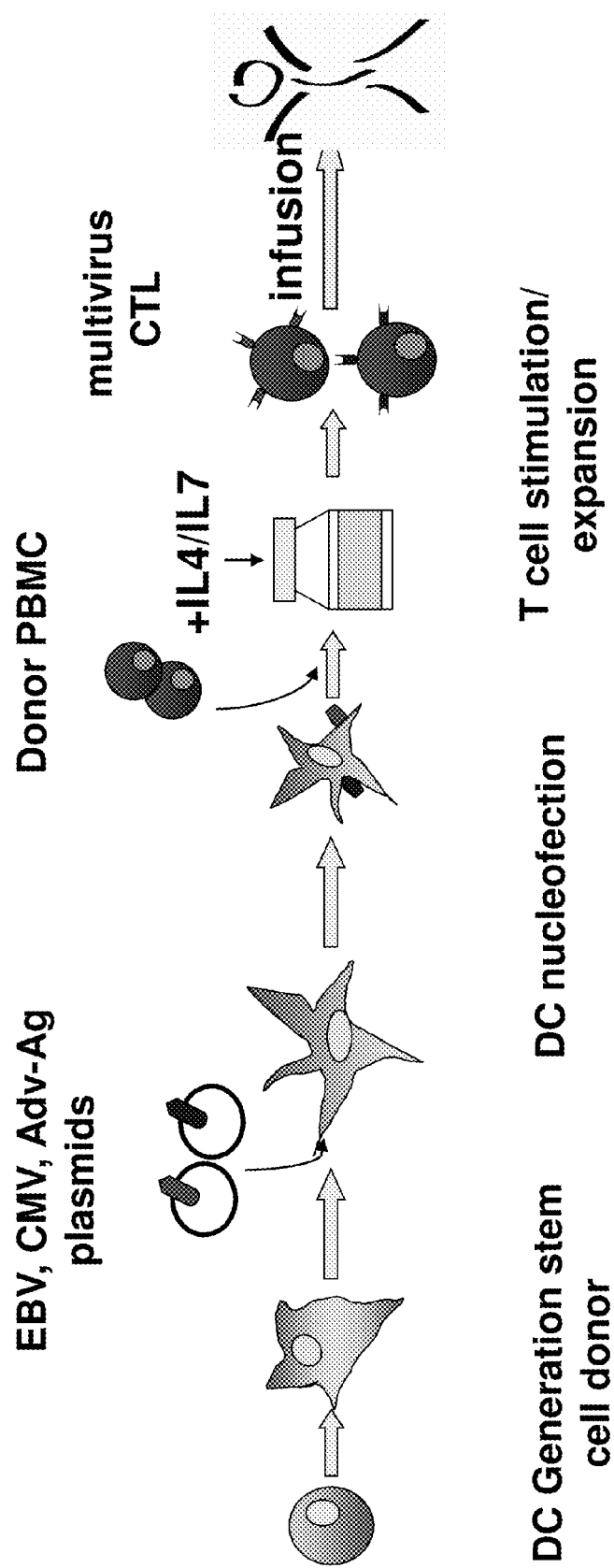
FIG. 5 illustrates one embodiment of a novel protocol to generate multivirus CTL using plasmids as a source of antigen and other exemplary refinements, such as the addition of the cytokines IL4 and IL7 and culture in the G-Rex bioreactor.

FIG. 3 provides a conventional approach for generating virus-specific (for example) CTL for adoptive transfer. Donor-derived B cells were first transformed in EBV-transformed lymphoblastoid cell lines (LCL) to use as antigen presenting cells. Once established (which can take 4-6 wks) donor PBMCs are transduced with an adenoviral vector expressing the immunodominant pp65 antigen from CMV. Monocytes in the PBMCs are preferentially transduced and stimulate virus-specific T cells which then are expanded in additional rounds of stimulation using LCLs transduced with the same vector as APCs (Leen et al., 2006). This process is time consuming and expensive (for production of clinical grade Ad vector and EBV virus). In certain embodiments of the invention, there is generation of multivirus-specific CTL (FIG. 4) that is an alternative to using Ad vector and EBV virus as sources of antigen for T cell stimulation. DNA plasmids were generated encoding viral antigens from EBV, CMV and Ad (for example). These can be expressed in APCs by nucleofection, and then the APCs can be pooled and used to stimulate T cells (Gerdemann et al., 2009). In the present invention, the inventors have now developed a novel protocol to generate multivirus CTL using plasmids or pepmixes as a source of antigen and, in certain embodiments, other refinements such as the addition of the cytokines IL4 and IL7 to the cell culture medium in which the CTLs are cultured. Such embodiments are useful for maintaining the breadth of reactivity in the CTL lines, and culture in the G-Rex bioreactor supports maximal T cell expansion (FIG. 5).

Figure 9:
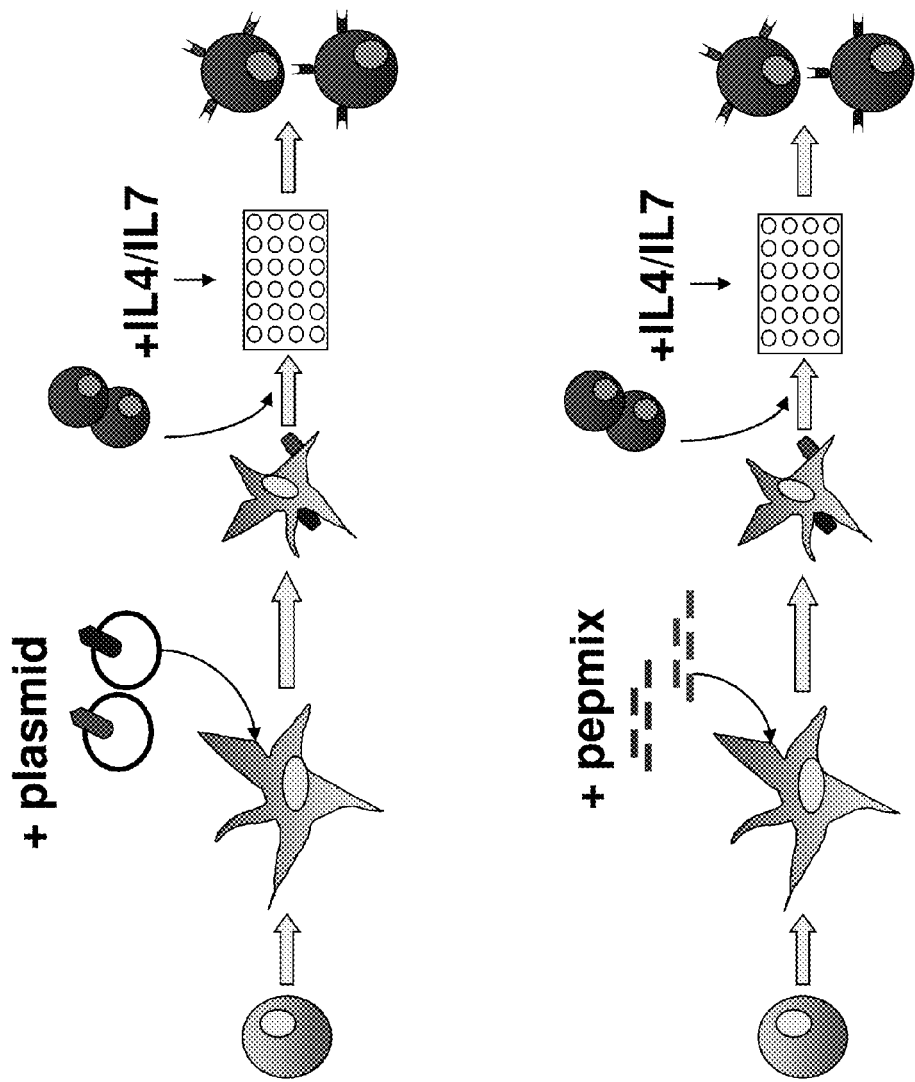
FIG. 9 shows a comparison of CTL generation utilizing plasmids or pepmixes.
Figure 10:
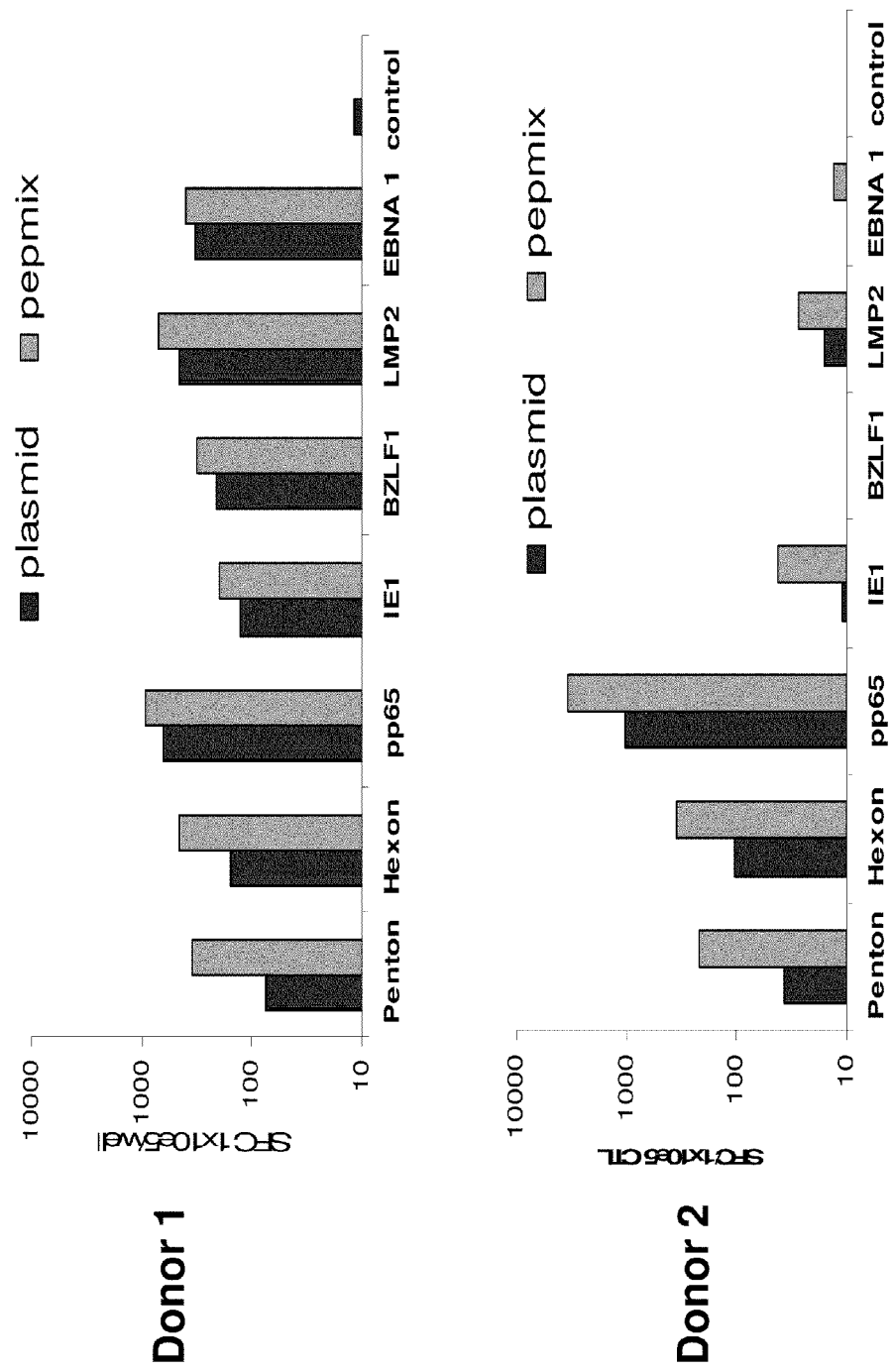
FIG. 10 shows a comparison of plasmid vs. pepmixes for CTL specificity.
Figure 11:
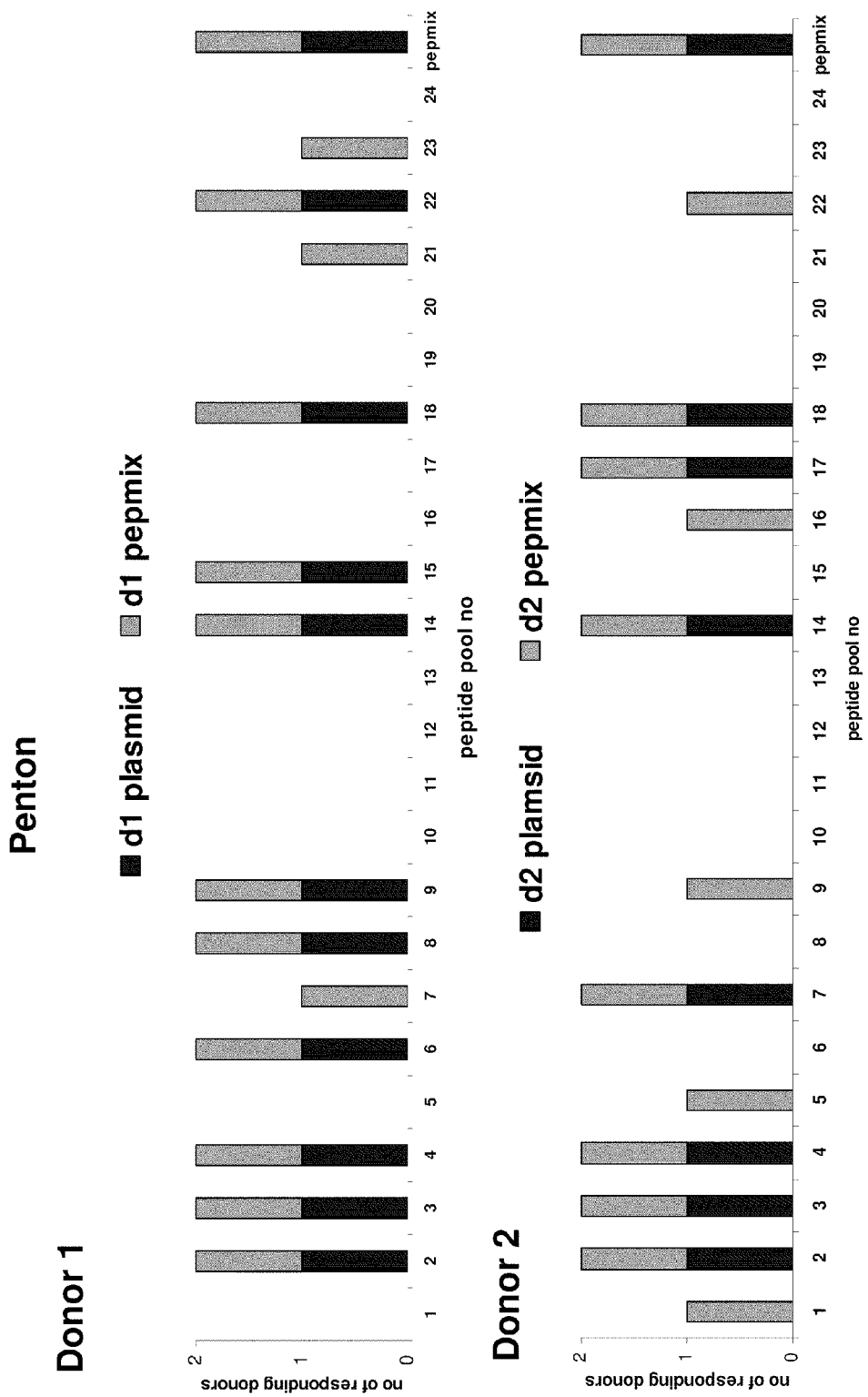
FIG. 11 demonstrates a broader epitope spectrum with pepmixes.
Figure 12:
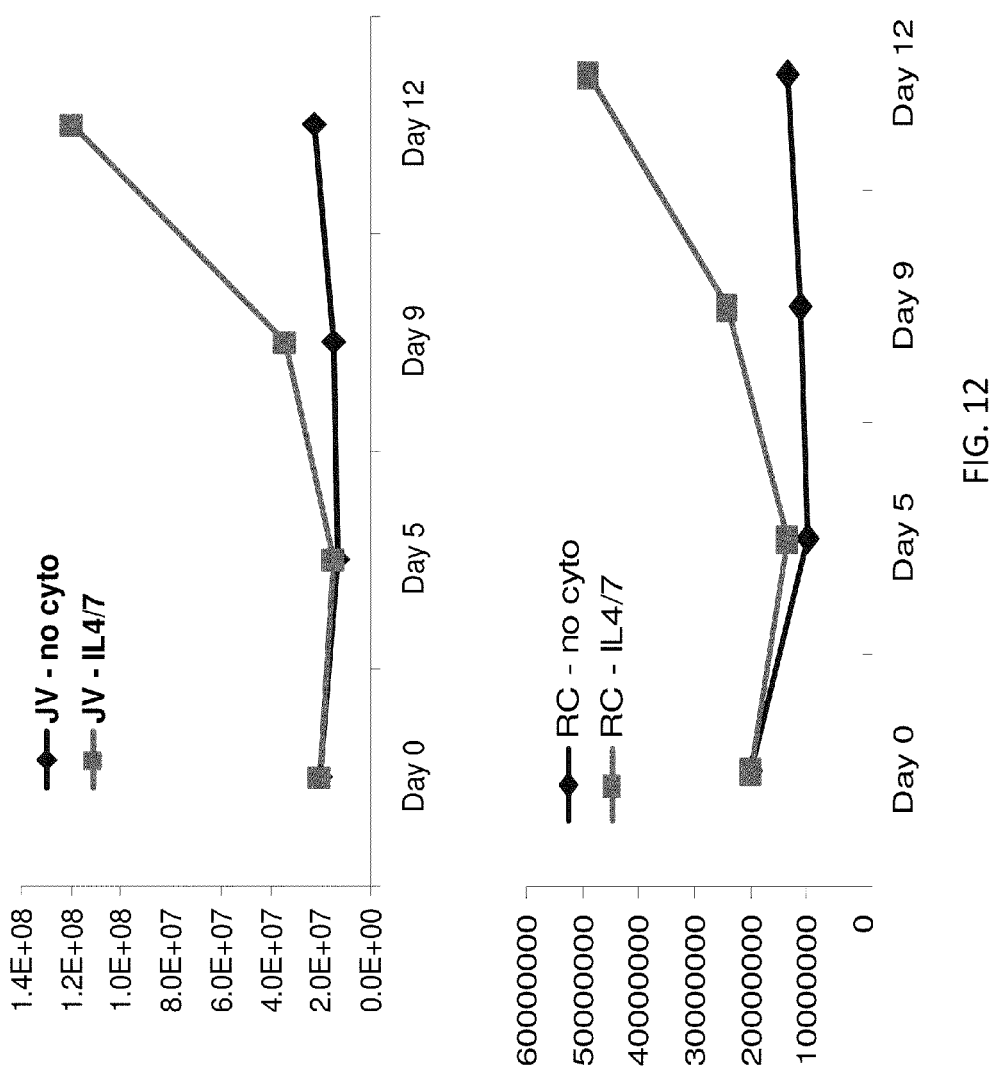
FIG. 12 illustrates CTL generation using pepmixes/bioreactor.

CTL generated in the presence of IL4 and IL7 recognize a broad repertoire of peptides from the target antigens/viruses (FIGS. 9, 10, 11) and have minimal alloreactivity—i.e. do not recognize normal cells from a potential recipient (FIG. 12). Thus, CTL produced in the invention are highly virus-specific and do not recognize uninfected cells of the intended recipient and therefore should not induce graft-vs-host disease (GVHD) after infusion.

For the exemplary plasmids for multivirus-specific CTLs, one can employ multicistronic plasmids expressing (for example) 2 or 3 or more immunogenic genes from the target viruses Ad, EBV, and CMV (for example). One exemplary Adenoviral construct (7970 bp) comprises Hexon:IRES:Penton (2858 bp Hexon and 1715 bp Penton). One exemplary EBV construct (6641 bp) comprises EBNA1ΔGALMP2:IRES:BZLF1 (1926 bp EBNΔ1A; 1493 bp for LMP2; and for 737 bp BZLF1). One exemplary CMV construct (6583 bp) comprises TEL IRES: pp65 (1471 bp for IE1 and 1686 bp for pp65). The bicistronic plasmids were efficient at activating T cells. For generation of the plasmids, one or more of the following characteristics would be useful, in certain aspects: backbone as small as possible (2.8-3 kbp, for example); optimized promoter, such as a CMV promoter (SV40 enhancer); no antibiotic resistance gene; and no homology to human genomic DNA. In some cases, instead of an antibiotic resistance gene, the plasmid comprises bacterial selection via sucrose (levansucrase (SacB) is a conditional lethal in bacteria) (Nature Technology Corporation).

In certain embodiments of the invention, the CTL line is a mixture of both CD4+ and CD8+ T cells. In some cases, an expected profile of reactivated cells against the different target antigens is as follows:

| Antigen | Predominant T cell restriction |
|---------|-------------------------------|
| IE1     | CD8                           |
| pp65    | CD8                           |
| EBNA1   | CD4                           |
| LMP2    | CD4+CD8                       |
| BZLF1   | CD8                           |
| Hexon   | CD4                           |
| Penton  | CD4                           |

Figure 6:
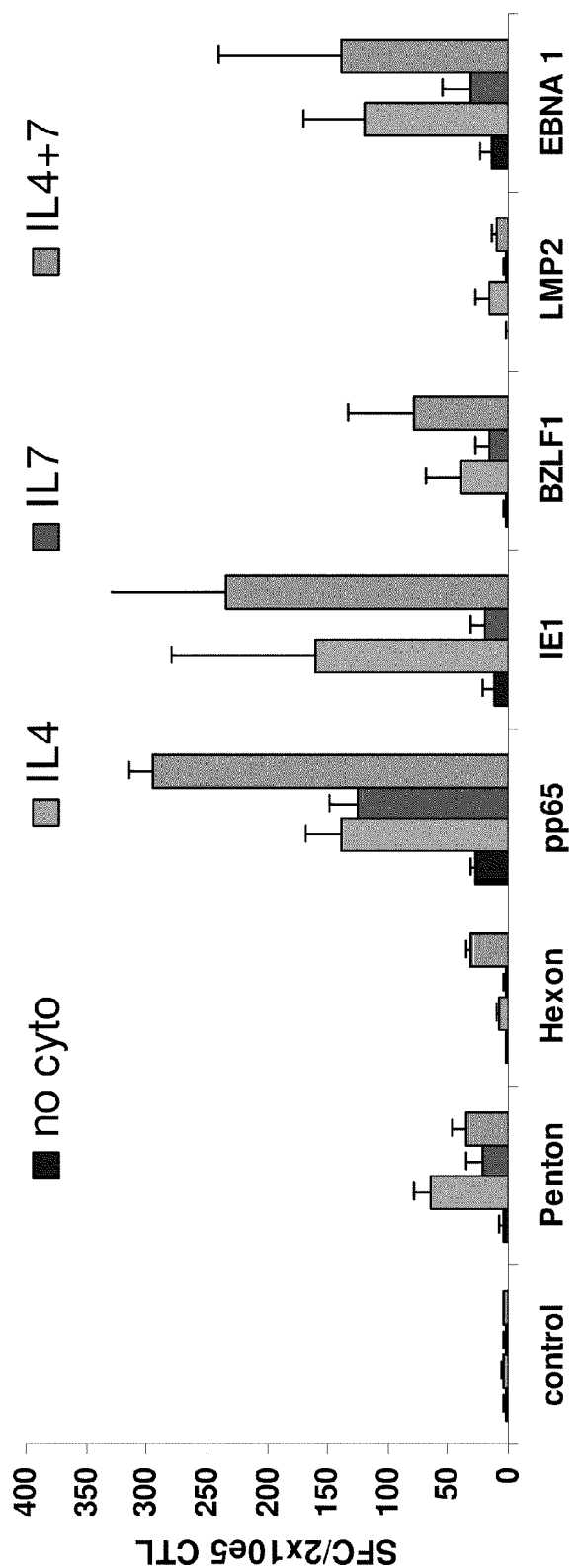
FIG. 6 illustrates a higher CTL specificity with the addition of IL4 and IL7.
Figure 7:
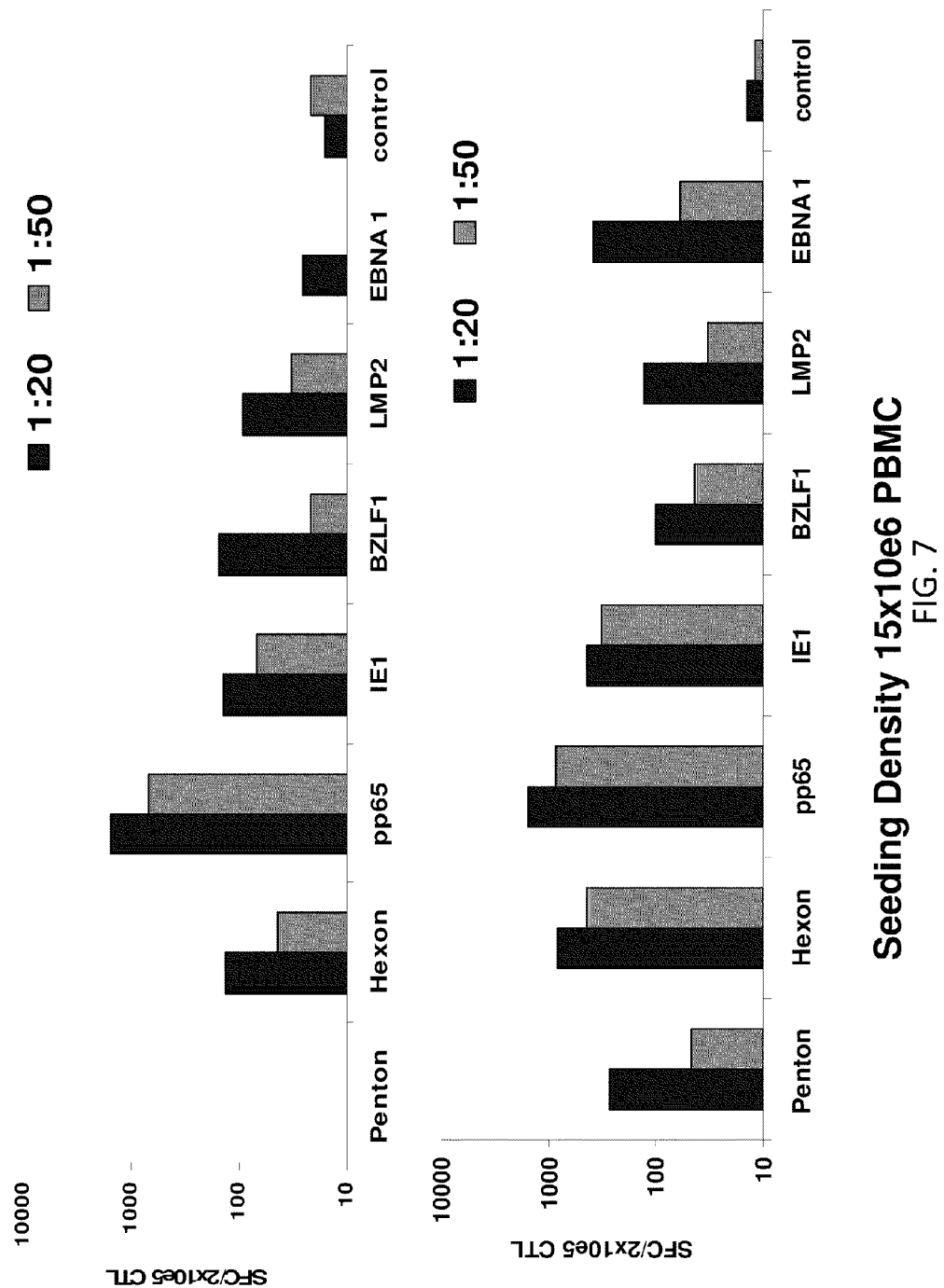
FIG. 7 demonstrates optimization of the seeding density of DCs:PBMCs for the initial stimulation and showed that a ratio of at least 1:20 was required for optimal activation.

Regarding cytokines, FIG. 6, IL4 and/or IL7 enhanced the frequency of virus-reactive cells in at least certain cultures. FIG. 7 shows optimization of the seeding density of DCs:PBMCs for the initial stimulation and showed that a ratio of at least 1:20 was required for optimal activation.

Figure 8:
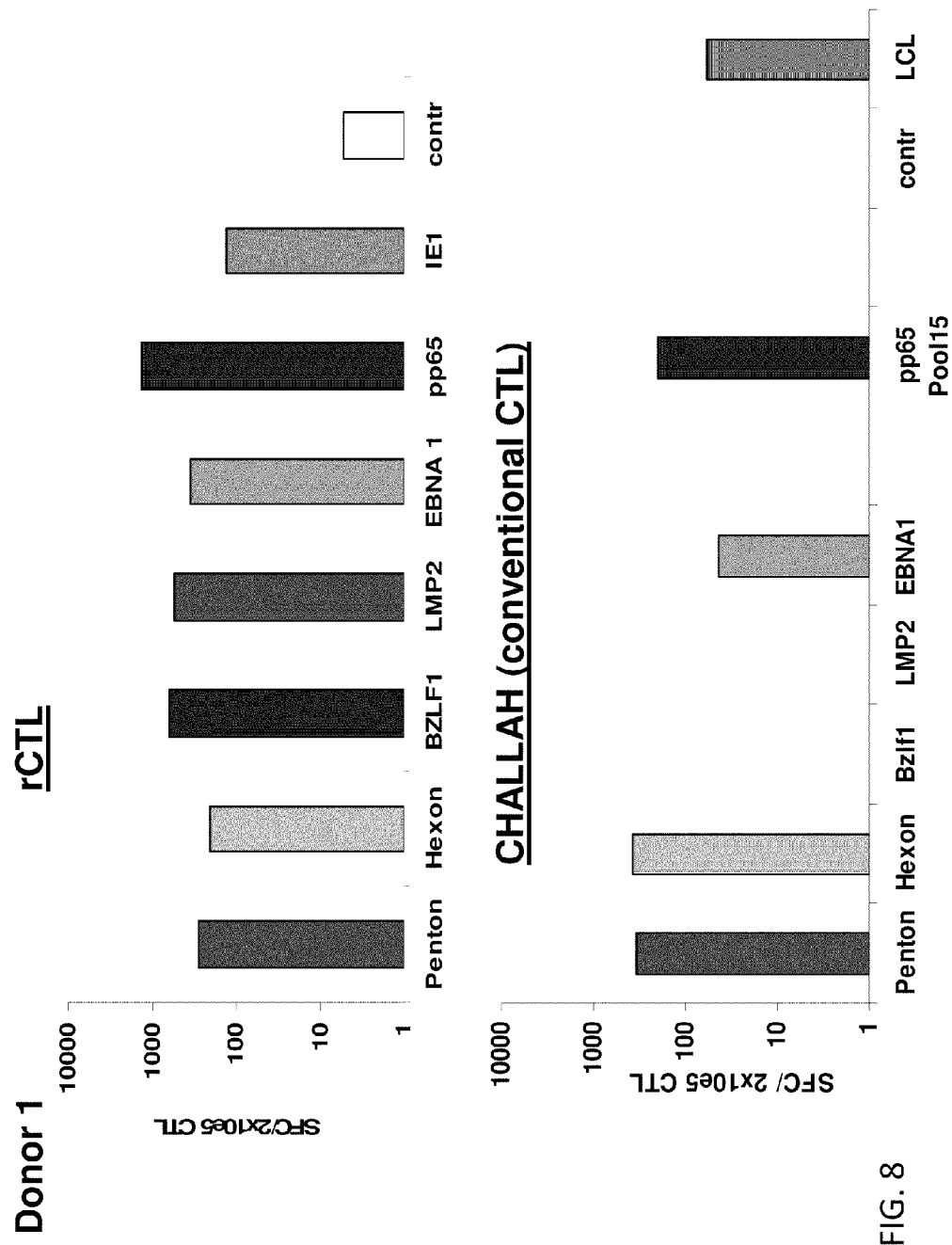
FIG. 8 illustrates that rCTL are comparable in specificity to those produced using a conventional protocol.
Figure 18:
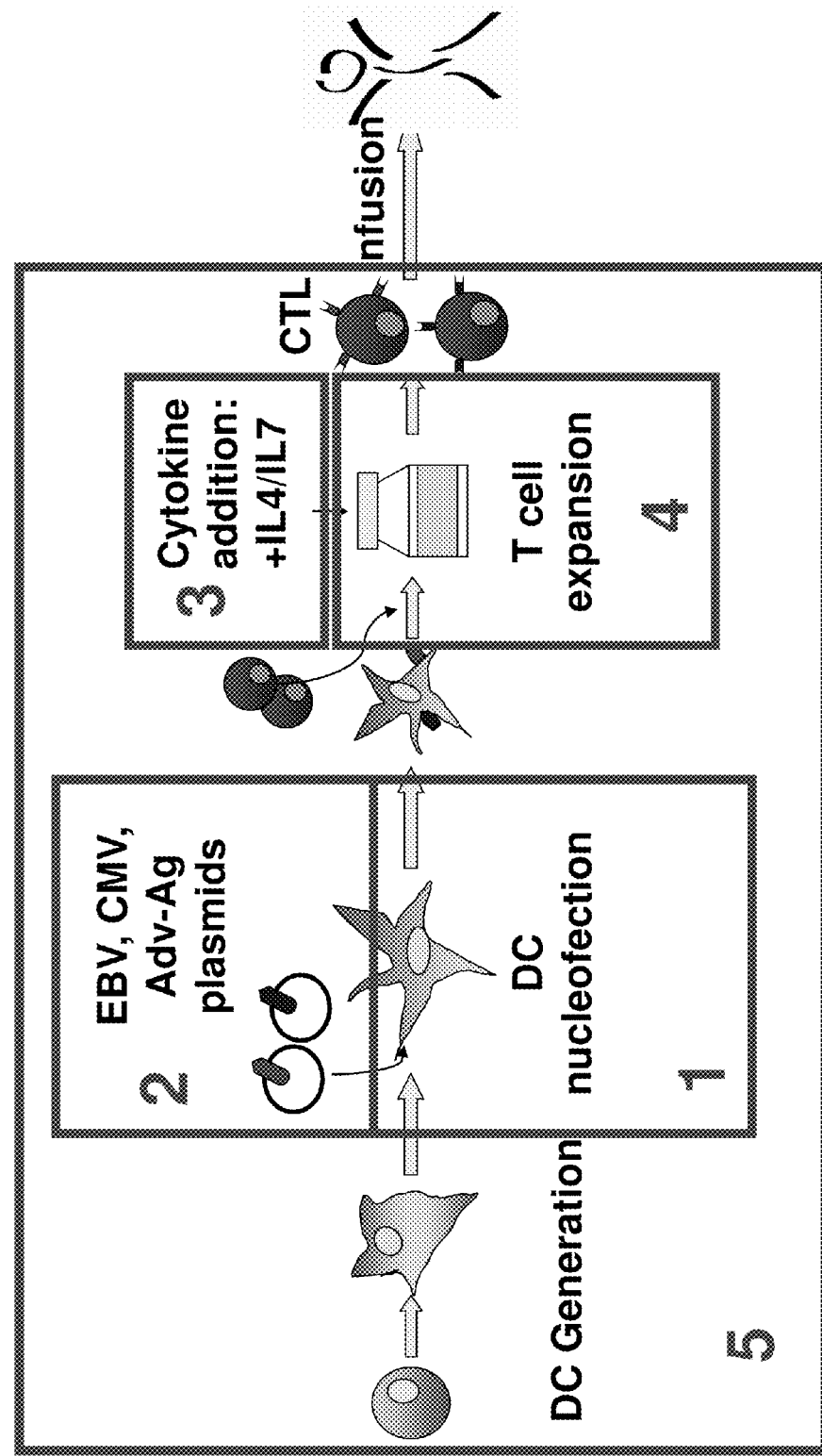
FIG. 18 shows the results of clinical rCTL generation procedure including multiple components of an embodiment of a system of the invention.

FIG. 18 shows the results of clinical rCTL generation procedure including multiple components of an embodiment of a system of the invention, for example the following: 1) DC nucleofection; 2) EBV, CMV, Adv-Ag plasmids; 3) cytokine addition of IL4/IL7; 4) T cell expansion in G-Rex; and 5) DC generation. In FIG. 8, it is shown that the inventors could produce CTL with characteristics similar to those produced using the conventional protocol but in a fraction of the time. These cells should be safe in vivo and associated with minimal alloreactivity as assessed by chromium release assay.

For rapid multivirus rCTL generation, nucleofecting the DCs may occur by any useful means in the art, including, for example the Amaxa® nucleofection system or the InVitrogen® nucleofection system. Multivirus CTL can also be rapidly generated by pulsing DCs with pepmixes spanning the target antigens or by stimulating PBMCs directly with the antigens of interest.

Model antigens expressed by Lymphomas include, for example, SSX2, Survivin, MAGE-4, PRAME, and NY-ESO-1. Model antigens expressed by Leukemias include, for example, Survivin, WT1, Proteinase 3, and PRAME. In certain embodiments, the whole antigen source includes a PepMix, which is an overlapping library of peptides, for example 15-mer peptides (and has the benefit of imparting no HLA restriction).

EXAMPLE 1

Generation and Dna Nucleofection of Dendritic Cells For Ctl Stimulation

Dendritic cells are the most powerful antigen-presenting cells known. Stimulation of peripheral blood (PB) T cells with mature dendritic cells (DC) expressing antigen, can lead to reactivation of antigen-specific cytotoxic T lymphocytes (CTL). DC can be differentiated from adherent PB mononuclear cells (PBMC) by culture in GM-CSF and IL-4. Antigen(s) can be introduced into DCs by nucleofection with DNA plasmids and the DCs can then be matured by culture in a cytokine cocktail containing IL1β, IL6, TNFα, and PGE-2.

In this example, an exemplary procedure is provided for preparing and nucleofecting dendritic cells as a component required for the generation of therapeutic T cells. The specimen in certain embodiments may comprise heparinized peripheral blood from patient or donor (or previously frozen PBMC). Infectious disease testing may have been performed within 7 days of blood collection.

Preparation of PBMCs from Fresh Blood is Performed (if using cryopreserved blood, proceed as described below). Dilute heparinized peripheral blood (ideally 60 ml) in an equal volume of D-PBS or RPMI 1640 at ambient (room) temperature. In a 50 ml centrifuge tube, carefully overlay approximately 10 ml Lymphoprep with approximately 20 ml of diluted blood. Adjust as necessary to utilize all the available cells. Centrifuge at 400×G for 40 minutes at ambient temperature. Save 3×1 ml plasma aliquots and store at −80° C. Harvest PBMC interface into an equal volume of D-PBS or RPMI 1640. Centrifuge at 450×G for 10 minutes at ambient temperature. Aspirate supernatant. Loosen pellet by "finger-flicking" and resuspend in 20 ml of D-PBS or RPMI 1640. Remove 20 µl of cells. Add 20 µl of 50% red cell lysis buffer and count using a hemacytometer.

For preparation of previously frozen PBMCs, thaw cells at 37° C., dilute in 10 mL of warm CellGenix DC medium per 1 mL of frozen cells, and count. For DC initiation, proceed as follows. Calculate the number of 35 mm wells of a 6 well plate(s) seeded at ~10×10$^6$ PBMC per plate (range 7 to 14×10$^6$) to use all available PBMC. Centrifuge at 400×G for 5 minutes at ambient temperature. Resuspend cells in 2 mLs per plate to be seeded. Transfer to 37° C./5% CO$_2$ incubator for two hours to adhere DC precursors. Rinse wells three times with 10 mls of D-PBS or RPMI, combining the supernatants containing the PBMC non-adherent fraction. To the remaining adherent cells, add 2 mls of DC culture medium containing 1000 units per ml of IL-4 and 800 units per ml of GM-CSF per well. Return flasks/plate(s) to 37° C., 5% CO$_2$ incubator. If not previously cryopreserved, non-adherent cells may be cryopreserved for future use responder T cells.

Immature DC are fed. On day 3 or 4, replenish IL-4 to 1000 units per ml and GM-CSF to 800 units per ml. Make up CellGenix medium containing 20×GM-CSF and IL-4 and add 100 µL per well.

At maturation of DC, harvest immature DC on day 5 or 6 by gentle resuspension (by now there should only be a few cells adhering to the flask). To remove remaining adherent cells, add 5 mls of cold D-PBS for approximately 1 minute and gently resuspend and combine with immature DC.

Perform cell count using hemacytometer. Count only large dendritic cells. Resuspend DCs at $2\times10^6$ per mL in Cell-Genix medium and aliquot 1 mL per well of a 24 well plate. Add sterile water to unused wells. Add 1 ml of DC culture medium containing the cytokine maturation cocktail.

| Cytokine | Final Concentration |
| --- | --- |
| GM-CSF | 800 U/ml |
| IL-4 | 1000 U/ml |
| TNF-α | 10 ng/ml |
| PGE-1 | 1 µg/ml |
| IL-1β | 10 ng/ml |
| IL-6 | 100 ng/ml |

Incubate DCs for 20-28 h in 37° C., 5% $CO_2$ incubator. Harvest 24 h-mature DC after 20-28 h by gentle resuspension with a 3 ml transfer pipette. Perform cell count using hemacytometer. Count only large dendritic cells. For nucleofection of dendritic cells, pre-warm 4 ml of Cell Genix media in a 6 well plate in a 37° C./5% $CO_2$ incubator. Divide harvested dendritic cells in 3 (Tube 1-3) 15 ml centrifugation tubes. DC cell number/tube should not be lower than $0.5\times10^6$ and higher than $2\times10^6$. Centrifuge DCs for 10 min at 200 g. Aspirate supernatant and add DNA plasmids to DC pellet in a final concentration of 5 µg/tube. Add DNA plasmid NTC IE1-pp65 to tube 1, add DNA plasmid NTC E1dGALMP2-BZLF1 to tube 2 and add DNA plasmid NTC Hexon-Penton to tube 3. Resuspend DCs and DNA with 100 µl of nucleofection solution, mix well and transfer to the nucleofection cuvettes. Place the cuvettes in to the Nucleofector, choose program U2 and start the nucleofection by pressing the start button. After Nucleofection immediately add 500 µl of the pre-warmed Media to the cuvette and transfer the cuvette to a 37° C./5% $CO_2$ incubator. After 10 minutes transfer nucleofected DCs to a 12 well tissue culture treated plate and add 1.5 ml of DC culture medium containing the cytokine maturation cocktail.

| Cytokine | Final Concentration |
| --- | --- |
| GM-CSF | 800 U/ml |
| IL-4 | 1000 U/ml |
| TNF-α | 10 ng/ml |
| PGE-1 | 1 µg/ml |
| IL-1β | 10 ng/ml |
| IL-6 | 100 ng/ml |

Incubate for 12-18 h at 37° C. in 5% $CO_2$ incubator.

DCs are harvested and irradiated for use as APCs. Harvest and count. Irradiate DC for use as APCs with 30 Gy. Wash once with 10 ml of medium. Resuspend at 2 or $1\times10^5$ per mL with CTL culture medium. DC are now ready for use as stimulators for PBMCs or CTLs.

EXAMPLE 2

Generation of Antigen-Specific Cytotoxic T-Lymphocytes (Ctls) Using Plasmid Nucleofected Dendritic Cells The present example concerns exemplary manufacturing of antigen specific cytotoxic lymphocytes. This procedure may be used to prepare cells for protocols that use plasmid nucleofected DCs as antigen-presenting cells. In certain cases, DCs are nucleofected with plasmids encoding Hexon-IRES-Penton, IE1-IRES-pp65, and E1dGALMP2-IRES-BZLF1, for example.

Antigen-specific cytotoxic T cell lines (CTLs) can be generated by stimulation of peripheral blood mononuclear cells (PBMC) with autologous antigen-presenting cells (APC) expressing the antigen from a DNA plasmid. The APC are the dendritic cells (DC), in certain embodiments of the invention. Dendritic cells are potent APCs that can be efficiently nucleofected and are used to generate virus-specific T cells from patients. In certain embodiments, plasmid-nucleofected dendritic cells can be used for second or subsequent stimulations. Under the culture conditions employed, outgrowing T cell lines should contain T cells specific for the antigens of interest (CMV-IE1 and pp65, Adenovirus antigens and EBV antigens). Cytokines (IL-4 and IL-7) are added at the first stimulation.

Heparinized peripheral blood may be used from the patient, or previously frozen patient PBMC. Infectious disease testing may be performed within 7 days (depending on specific protocol) of blood collection. Plasmid nucleofected dendritic cells (DC) are prepared from the patient or donor.

One may calculate the final expanded T cell numbers required. Sufficient cells are required for patient doses and QC testing according to the patient's body surface area, predicted dose levels and whether additional doses are allowed. In certain embodiments, one allows for the chance that the patient may be enrolled on a higher dose level than expected. DCs should be prepared in CellGenix medium to ensure they do not present fetal calf serum antigens, in particular cases. CTL initiation is performed in the presence of FCS.

Preparation of mononuclear "responder" cells from fresh blood is performed (for frozen blood, see below). Dilute heparinized peripheral blood (for example, 60 ml) in an equal volume of D-PBS or RPMI 1640 at ambient (room) temperature. In a 50 ml centrifuge tube, carefully overlay approximately 10 ml Lymphoprep with approximately 20 ml of diluted blood. Adjust as necessary to utilize all the available cells. Centrifuge at 400×G for 40 minutes at ambient temperature. Save 3×1 ml plasma aliquots and store at −80° C. Harvest PBMC interface into an equal volume of D-PBS or RPMI 1640. Centrifuge at 450×G for 10 minutes at room temperature. Aspirate supernatant. Loosen pellet by "finger-flicking" and resuspend in 20 ml of D-PBS or RPMI 1640. Remove 20 µl of cells. Add 20 µl of 50% red cell lysis buffer and count using a hemacytometer. If appropriate, one can then proceed to PBMC stimulation by dendritic cells in plates or bioreactors.

preparation of responder cells from previously frozen PBMCs or non-adherent mononuclear cells may be performed, if necessary. Thaw cells at 37° C., dilute in 10 mL of warm medium per 1 mL of frozen cells. Cells are counted.

In appropriate situations, one can proceed to PBMC stimulation by dendritic cells, for example in plates or in bioreactors. Centrifuge at PBMCs at 400×G for 5 minutes at room temperature. Remove supernatant and resuspend at $2\times10^6$ cells per mL in CTL media+IL4 (1000 U/ml—final concentration) and IL7 (10 ng/ml—final concentration). Aliquot 1 mL of cells per well of a 24 well and return plate to incubator or aliquot 5 to 7.5 mL (10 to $15\times10^6$) PBMCs in a GP40 bioreactor and return to incubator. Obtain prepared plasmid nucleofected DCs, irradiated with 30Gy and washed 4 times. Resuspend antigen presenting cells at $2\times10^5$ to $1\times10^5$ (DC) cells/ml for a 10:1 or 20:1 ratio of PBMC to DC. Aliquot 1 ml DCs into PBMC wells, or 7.5 mL of DCs into Bioreactor and add medium to 30 mL. Culture at 37° C. in 5% $CO_2$ in air for 7 days. On Day 7: If there are $<3\times10^6$ cells/well perform a one-half media change. Remove ~1 mL of medium per well and replace with ~1 mL of fresh CTL medium+cytokines. On Day 7: If there are >3×10⁶ cells/well split and feed CTL; transfer ~1 mL of CTL to new well; feed with ~1 mL of fresh CTL medium+cytokines. On Day 7: If there are <50×10⁶ cells in bioreactor remove 10 ml media and replenish with fresh media+cytokines. On Day 7: If there are >50×10⁶ cells in bioreactor transfer 15 ml CTL to new bioreactor and replenish both with fresh media+cytokines. Culture for additional 4-6 days. For clinical cryopreservation, when sufficient cells have been obtained, cryopreserve and characterize cells. Within one week of freezing CTLs, cytotoxicity assays should be set up with $5 \times 10^6$-$1 \times 10^7$ cells and phenotyping should be done with an additional $2 \times 10^6$ cells according to specific protocol requirements.

In certain embodiments, the cells may have the following characteristics, in certain embodiments: 1) sufficient CTL numbers for infusion of the patient at the appropriate dose level (determined at that time) and for all QC requirements; <10% killing of recipient PHA blasts at 20:1 (if allogeneic); and 3)<2% CD 83+/CD3 cells (exclusion of DC).

EXAMPLE 3

Figure 19:
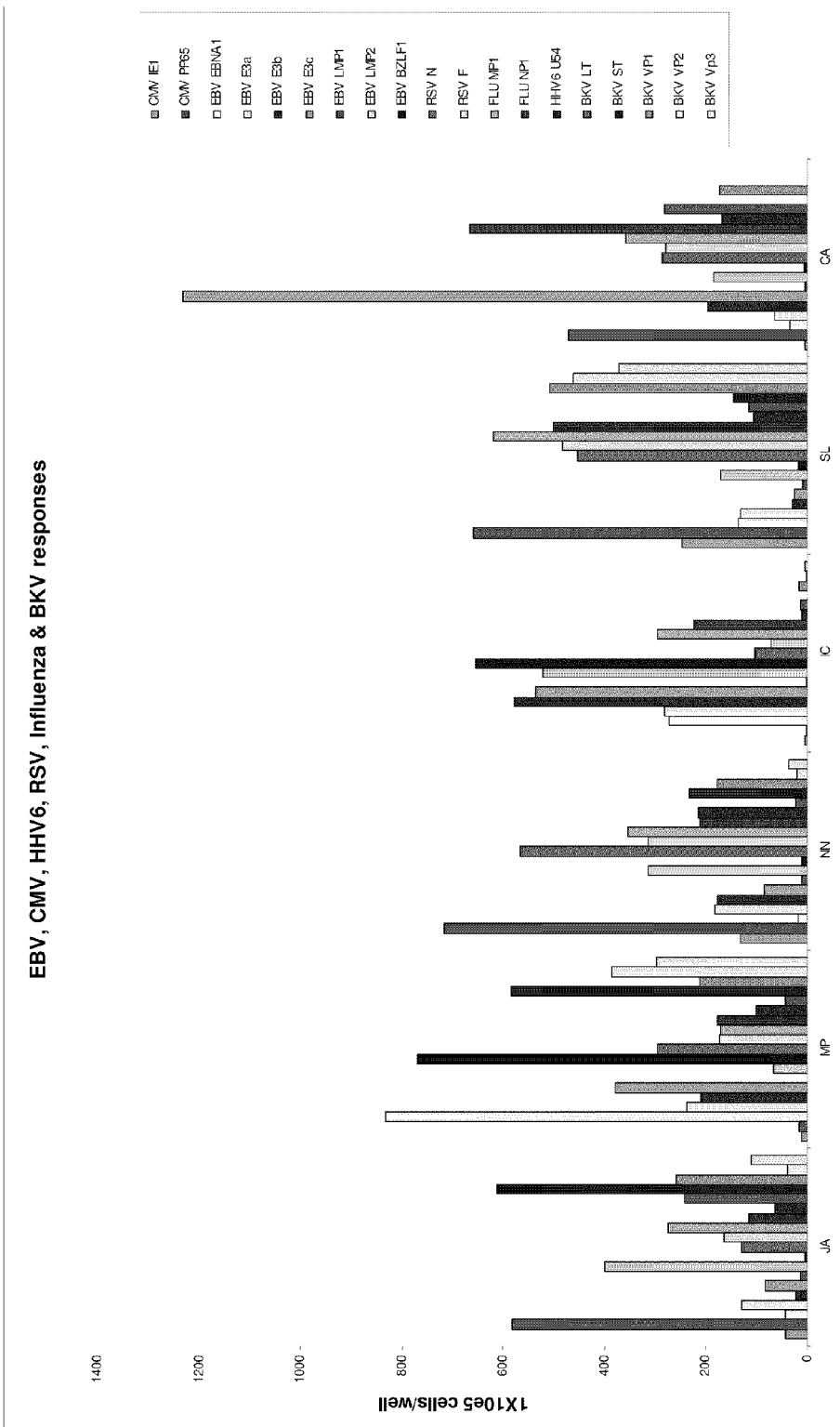
FIG. 19 shows responses to 5 exemplary viruses (CMV, EBV, Ads, BK and Influenza). The antigens from each of the viruses used are in the legend, where the bars are ordered from left to right as the legend proceeds from top to bottom.

Multivirus-Specific Ctl For The Prophylaxis and Treatment Of EBV, CMV and Adenovirus Infection Post Allogeneic Stem Cell Transplant One can use the methodology of the present example to generate a multivirus-specific T cell product that also targets any combination of viruses, not just those illustrated herein. In certain embodiments of the invention, there are rapidly generated donor-derived multivirus-specific CTL lines that have antiviral activity against three exemplary viruses: EBV, CMV and adenovirus. However, the multivirus CTLs may be directed against two, three, four, five, six, seven, eight, nine, ten, or more viruses. In addition to EBV, CMV and/or adenovirus as a target, the CTLs may be directed against one or more of HHV-6, BK, RSV, Influenza, or Parainfluenza, for example (see FIG. 19).

The present example describes an exemplary phase I/II study to evaluate the safety and toxicity of donor-derived rapidly generated multi-virus-specific cytotoxic T lymphocytes (rCTLs) in patients at risk of developing CMV, adenovirus or EBV infections after allogeneic stem cell transplant. First, a phase I dose-escalation study is employed to address safety of four exemplary rCTL dose levels and determine the maximum tolerated dose (MTD) level. Dose-limiting toxicity is defined as development of Grade III-IV GVHD within 42 days or NCI grade 3-5 infusion-related adverse events in any organ system that can be attributed to rCTLs but is not pre-existing and not due to the underlying malignancy or relapse within 30 days of CTL administration.

Background

Reconstitution of anti-viral immunity by donor-derived CTLs is useful for preventing and treating infections with CMV, EBV and adenovirus post-transplant (Leen et al., 2006). However, the broader implementation of T cell immunotherapy using conventional protocols is limited by (i) the cost of production (ii) the complexity of production limiting scalability, and (iii) the time required for CTL production, which not only contributes to cost and complexity but also precludes urgent treatment of seriously ill patients, unless CTLs have been prepared speculatively, and well in advance.

Provided herein is a rapid protocol for the generation of donor-derived multivirus-specific CTLs (rCTL) for infusion to allogeneic hematopoietic stem cell transplant (HSCT) recipients at risk of developing infection, such as CMV, adenovirus or EBV infections or with early infection. In specific embodiments, there is administering of rapidly generated donor-derived multivirus-specific CTLs to mediate antiviral activity in HSCT recipients at risk of developing or with active viral reactivation or infection.

Patients may receive the cells as prophylaxis and/or treatment for early infection following any type of allogeneic transplant. If patients are receiving steroids for treatment of graft-versus-host disease (GVHD) or for other reasons, dosage must be tapered to ≤0.5 mg/kg Prednisone (or equivalent). Patients may not have received ATG, or Campath or other immunosuppressive monoclonal antibodies in the previous 28 days, in certain aspects of the invention.

In certain embodiments of the invention, patients receive between $5 \times 10^6$ and $5 \times 10^7$ rCTL/m² in a single infusion on the dose escalation safety phase of the study and $5 \times 10^7$ rCTL/m² for the fixed dose Phase II efficacy component. If they have a partial response (as defined) or receive therapy post-infusion that could ablate the infused T cells, they are eligible to receive up to 2 additional doses, for example. Individuals may be followed by PCR analyses of viral load and may have GvHD scores recorded at the intervals defined.

In the present example, it is determined whether rCTLs are safe and have activity against three exemplary viruses EBV, CMV and adenovirus. Patients may have one or more of the following characteristics: 1) prior allogeneic hematopoietic stem cell transplant using either bone marrow or PBSC; 2) Karnofsky/Lansky score of ≥50; 3) ANC greater than 500/μL; 4) Bilirubin<2×, AST<3×, Serum creatinine<2× upper limit of normal, Hgb>8.0; 6) Pulse oximetry of >90% on room air; 7) Negative pregnancy test (if female of childbearing potential); and 8) Available tri-virus-specific cytotoxic T lymphocytes.

In an exemplary clinical protocol, a primary endpoint For Phase 1 component encompasses safety including acute GvHD by day 42 and infusion-related adverse events or nonhematological adverse events within 30 days of the last CTL infusion. An exemplary primary endpoint for Phase II component includes safety and antiviral responses. Exemplary secondary Endpoints for both phases includes effects of rCTL on viral loads in patients with infection; reconstitution of antiviral immunity at 1, 2, 4, 6 and 8 weeks and 3 months; and/or viral reactivations within 3 months.

Viral Infection Post Transplant

During the period of immune recovery after hematopoietic stem cell transplantation (HSCT) viral infections, which are normally controlled by T-cell immunity, are an important cause of morbidity and mortality. The degree of risk for infection is dictated by the degree of tissue mismatch between donor and recipient, and the resultant degree of immunosuppression, and by the immune status of the donor. Reactivation of latent viruses such as cytomegalovirus (CMV) and Epstein-Barr virus (EBV), for example, is common and often causes symptomatic disease. Respiratory viruses such as adenovirus, influenza, and respiratory syncytial virus (RSV), for example, also frequently cause infection. Antiviral pharmacologic agents are only effective against some of these viruses; their use is costly and is associated with significant toxicities and the outgrowth of drug-resistant mutants. As delay in recovery of virus-specific cellular immune response is clearly associated with viral reactivation and disease in these patients, cellular immunotherapy to restore viral-specific immunity is useful to target three exemplary common viruses; CMV, EBV and adenovirus.

CMV

Cytomegalovirus (CMV) is a latent beta-herpesvirus that usually causes an asymptomatic infection in immunocompetent individuals. It persists in approximately 70% of healthy adults and replicates in epithelial cells, fibroblasts and monocytes. Reactivation of CMV in the stem cell recipient can result in significant morbidity and mortality, with clinical manifestations including interstitial pneumonitis, gastroenteritis, fevers, hepatitis, encephalitis and retinitis (Boeckh et al., 2003). Cell-mediated immunity is considered the most important factor in controlling CMV infection and CMV-specific CD4+ and CD8+ lymphocytes play an important role in immune protection both primary infection and subsequent reactivations. The most frequently used drugs for prophylactic or preemptive therapy are ganciclovir and foscarnet. These drugs have been successful in reducing mortality associated with CMV disease and in preventing early CMV disease in combination with intravenous immune globulin. However, both have significant side effects including neutropenia and nephrotoxocity.

Epstein-Barr Virus

Epstein-Barr virus (EBV) is a gamma-herpesvirus that infects more than 95% of the world's population. Primary infection usually produces a mild self-limiting disease, which is followed by latent infection in B cells and productive replication in B cells and mucosal epithelium. There are at least four types of viral latency: type 1, expressing only the virus nuclear antigen 1 (EBNA1); type 2, expressing in addition to EBNA1, the latent membrane proteins, LMP1 and LMP2; and type 3, expressing all the seven latency-associated proteins including the immunodominant EBNA3 viral antigens (Young and Rickinson, 2004). In these types of latency the viral small RNAs and EBERs are abundantly expressed as well as transcripts from the BamHI A region of the viral genome, BARTs. In the fourth type of latency, found in the majority of circulating B cells of healthy individuals, no viral RNA expression can be detected. In immunocompromised hosts, outgrowth of B cells expressing Type 3 latency, which are highly susceptible to virus-specific T cells, may lead to the development of post-transplant lymphoproliferative disease (PTLD). The overall incidence of PTLD after HSCT is less than 1%, but the incidence is increased in recipients with an underlying diagnosis of immunodeficiency and for recipients of stem cells from unrelated or human-leukocyte-antigen (HLA)-mismatched donors who receive grafts that are selectively depleted of T cells to prevent graft-versus-host disease (GVHD) (Curtis et al., 1999; Cohen et al., 2007; Brunstein et al., 2006).

Few small molecule drugs have any effect on B cells already transformed by EBV, although nucleoside analogs, like ganciclovir, do inhibit the viral replicative cycle. Chemotherapy is rarely effective and associated with significant toxicity. One option for prophylaxis and treatment of PTLD after HSCT is rituximab, a monoclonal antibody against the B cell phenotypic antigen, CD20. Response rates to rituximab between 55% and 100% have been reported in different series (Brunstein et al., 2006; Keuhnle et al., 2000; Comoli et al., 2007). However, not all patients respond and rituximab depletes normal B-cells for more than 6 months, which can be problematic in a patient population that is already immunosuppressed.

Adenovirus

Adenovirus is a non-enveloped lytic DNA virus. Humans are susceptible to infection with 51 serotypes of adenovirus, forming six distinct species (A to F), which differ in their tissue specificity and virulence. Although acutely infecting viruses, adenoviruses may persist for many months after resolution of disease and therefore are frequently carried undetected into the transplant by donor or recipient. While acute infection is rarely fatal in healthy adults, it is a significant cause of morbidity and mortality in immunocompromised individuals, in whom it may produce pneumonia, hemorrhagic cystitis, nephritis, colitis, hepatitis, and encephalitis. Adenovirus has a particularly high incidence after pediatric HSCT (Myers et al., 2005). Several reports have shown that clearance of adenovirus infection is associated with detection of adenovirus-specific T cells (Feuchtinger et al., 2005; Myers et al., 2007) and recovery is significantly delayed in recipients of matched unrelated donor and haploidentical transplant who receive intensive immunosuppression such as Campath (Myers et al., 2007). The most frequently used drug for disease treatment is Cidofovir, but the associated nephrotoxicity is a major concern and in the absence of prospective, randomized, controlled trials, the efficacy of the drug is uncertain.

Adoptive Immunotherapy with Virus-Specific CTLs

Since recovery of virus-specific T cells is clearly associated with protection from infection with each of these viruses (Feuchtinger et al., 2005; Cwynarski et al., 2001; Gottschalk et al., 2005) adoptive immunotherapy to decrease the time to immune reconstitution is an attractive approach. Virus-specific T cells generated by repeated stimulation with antigen presenting cells expressing viral antigens have been evaluated in clinical trials to prevent and treat viral infections in immunocompromised hosts (Leen et al., 2006; Leen et al., 2009; heslop et al., 2009; Walter et al., 1995; Pegs et al., 2003). This approach eliminates alloreactive T cells.

There are several considerations in developing protocols for generating virus-specific CTLs ex vivo. Knowledge of the immunodominant antigens that induce protective T cells specific for the targeted virus is required and a delivery system to transfer the antigen to effective antigen-presenting cells (APCs) must be identified. The APC must be autologous, express major histocompatibility complex (MHC) antigens presenting relevant virus-derived peptides as well as co-stimulatory molecules sufficient to induce T cell activation and expansion. These reagents all need to be suitable for GMP manufacturing, which limits the use of some types and sources of antigen.

T Cell Therapy for CMV

The first study evaluating whether adoptively-transferred T cells could reconstitute anti-viral immunity targeted CMV. In this study, CMV-specific T-cell clones were derived from sibling donors after stimulation with autologous fibroblasts pulsed with CMV (Walter et al., 1995). There were no adverse effects and CMV-specific immune responses were reconstituted, with none of the patients developing CMV disease or late recurrence. Anti-CMV activity did decline, however, in recipients who did not develop CD4+ CMV-specific T-cell responses, indicating CD4 T cells may be necessary for long-term persistence, in certain cases. In another prophylaxis study, Peggs et al., generated CMV-specific CD4+ and CD8+ T cells by stimulation of peripheral blood mononuclear cells (PBMC) with dendritic cells pulsed with CMV antigens derived from a CMV-infected human lung fibroblast cell line (Peggs et al., 2003). Small doses of CTLs were able to reconstitute immunity with considerable in-vivo expansion of CMV-specific CTLs. To avoid the use of live CMV during T cell manufacture, a more recent study stimulated CTLs with dendritic cells pulsed with the HLA-A2 restricted peptide NLV derived from the cytomegalovirus-pp65 protein (Micklethwaite et al., 2007). While this approach also appeared effective, a concern is the restricted specificity of the infused CTLs, since targeting a single epitope may allow escape variants and limits the study to patients who are HLA A2-positive.

CMV-specific CTLs have also been used therapeutically in patients with CMV infection that has persisted or recurred despite prolonged antiviral medication (Einsele et al., 2002). The results were encouraging with suppression of viral reactivation in 6 of 7 subjects. In this study, the source of antigen was a CMV lysate, which has the advantage of producing a broad immune response but which is unsuitable for Phase III studies because of the risk of infection from live virus in the lysate.

The CTL therapies described above all employed methods of T cell production that require prolonged periods of activation and expansion in specialized GMP facilities with significant regulatory support. These requirements reduce the practicality of adoptive immunotherapy since CTL lines must be made long in advance of disease and few centers have the facilities or infrastructure required for this type of cell processing. A recently reported clinical trial using tetramer selection of CMV peptide-specific T cells directly from peripheral blood avoided both ex vivo expansion and live viral antigens. Although exclusively CD8+ T cells were infused, they expanded by several logs after infusion, clearing infection in 8/9 cases (Cobbold et al., 2005). This approach, however, is impeded by the limited availability of tetramers for uncommon HLA types and a lack of class II tetramers.

T Cell Therapy for EBV

The outgrowing EBV-infected B cells of PTLD have the same phenotype and viral antigen expression as the EBV-transformed lymphoblastoid cell lines (LCLs) generated by infecting peripheral blood B cells with a laboratory strain of EBV. As LCLs can be readily prepared from any donor, they have been used as APCs in clinical studies evaluating EBV specific CTLs (Comoli et al., 2007; Rooney et al., 1995; Rooney et al., 1998; Heslop et al., 1996; Gustafsoon et al., 2000). EBV-specific CTLs generated using this methodology are polyclonal, contain both CD4+ and CD8+ EBV-specific T cells, and recognize multiple latent and lytic viral antigens. Adoptively transferred EBV-specific CTLs can survive for at least 8 years, expand up to 2-4 logs after infusion, and reduce the high virus load that is observed in about 20% of patients (Heslop et al., 2009; Rooney et al., 1995; Heslop et al., 1996). In a recent review of three studies targeting high-risk patient populations, none of 101 patients who received EBV CTLs as prophylaxis developed PTLD (Heslop et al., 2010). Of 13 patients with active PTLD at the time of infusion, donor-derived EBV-specific CTL lines induced remission in 11 (Heslop et al., 2009), while in one of the non-responders, tumor virus had deleted the immunodominant epitopes in EBNA3 that were the targets of the infused effector T cells (Gottschalk et al., 2001). Other studies have confirmed the activity of EBV specific CTLs post transplant (Comoli et al., 2007; Gustafsson et al., 2000).

T Cell Therapy for Adenovirus.

Feuchtinger et al. treated patients with adenovirus infection using CD4+ and CD8+ adenovirus-specific T cells isolated from the donor after a short in vitro stimulation with adenovirus viral antigen followed by selection of gamma-interferon-secreting cells (Feuchtinger et al., 2006). Small numbers of adenovirus-specific donor T cells were infused into nine children with systemic adenovirus infection after HSCT. Adenovirus specific immune responses were detected in five of six evaluable patients, associated with a sustained decrease in viral load and clearance of infection (Feuchtinger et al., 2006).

Multivirus-Specific T Cells

The strategies described above each target only one virus. To broaden the specificity of single CTL lines to include the three most common viral pathogens of stem cell recipients, the inventors reactivated CMV and adenovirus-specific T cells by using mononuclear cells transduced with a recombinant adenoviral vector encoding the CMV antigen pp65. Subsequent stimulations with EBV-LCL transduced with the same vector both reactivated EBV-specific T cells and maintained the expansion of the activated adenovirus and CMV-specific T cells.1 This method reliably produced CTLs with cytotoxic function specific for all three viruses, which were infused into 14 stem cell recipients in a Phase I prophylaxis study. There was recovery of immunity to CMV and EBV in all patients but an increase in adenovirus-specific T cells was only seen in patients who had evidence of adenovirus infection pre-infusion (Leen et al., 2006). A follow-up study in which the frequency of adenovirus-specific T cells was increased in the infused CTLs produced similar results, thus highlighting the importance of endogenous antigen to promote the expansion of infused T cells in vivo (Leen et al., 2009). Nevertheless, all patients in both clinical trials with pre-infusion CMV, adenovirus or EBV infection or reactivation were able to clear the infection, including one patient with severe adenoviral pneumonia requiring ventilatory support (Leen et al., 2006). CTLs recognizing multiple antigens can therefore produce clinically relevant effects against all three viruses.

Limitations of Current CTL Generation Protocols

It is now evident that adoptive transfer of CTLs can treat viral infections and hematologic malignancies that are not amenable to conventional therapies. Because the benefits are sustained long term and the cells produce minimal toxicities, this approach has a potentially outstanding pharmaco-economic profile. Unfortunately, wider application is limited by (i) the cost of production, which requires the initial manufacture of EBV-transformed lymphoblastoid cell lines (EBV-LCL) and the production and testing of clinical grade adenoviral vectors; (ii) the complexity of CTL production, which necessitates generation and genetic modification of APCs for weekly CTL stimulation, repeat feeding of open culture systems, and multiple skilled "judgment calls", thereby limiting scalability, and (iii) the time required for CTL production; to the 4 to 6 weeks for initial generation of EBV-LCLs must be added the additional 4 to 8 week CTL activation and expansion period required to increase the frequency of antigen-specific T cells and eliminate alloreactive T cells. Not only does this delay contribute to cost and complexity, it also precludes urgent treatment of seriously ill patients, unless CTLs have been prepared speculatively, and well in advance.

Rapid Generation of Multivirus-Specific CTL

Generation of Multivirus-Specific CTL Using DNA Plasmid-Nucleofected DCs as APCs To produce multivirus CTL more rapidly the inventors developed a protocol to replace both an Ad5 pp65 vector (Adv and CMV specificities) and an EBV-LCL (EBV specificities) with DNA plasmids that encode multiple viral antigens. These DNA plasmids can be introduced into the nucleus of APCs, such as monocytes or DCs, using the clinically applicable Lonza/AMAXA nucleofection system. After transfer, high level transgene expression is achieved with good target cell viability during the period of T cell activation (Gerdemann et al., 2009). Plasmids are non-infectious, non-replicative, and integrate poorly into the transfected cell genome. Clinical grade DNA can be rapidly and cost-effectively produced in scalable quantities with excellent long term stability. Substitution of plasmids reduces the cost of manufacture by more than 50%, by reducing the time of CTL manufacture and the extent of immunogen testing, since the cost of plasmid testing is about one tenth that of adenovirus vector testing.

The evaluation of protective and immunogenic Adv and CMV antigens encoded by these plasmid DNAs can be based on the encouraging clinical results showing that T cells directed against Adv-hexon and penton, and to CMV1-E1 and to CMV-pp65 are protective in vivo (Leen et al., 2009; Leen et al., 2008). CMV-IE1-specific T cells may target cells that reactivate CMV from latency, while pp65-specific T cells target newly-infected cells. The inclusion of two proteins for each virus in the immunogen increases the number of potential target epitopes and hence the probability that T cells will be reactivated irrespective of the HLA type of the T cell donors. Once administered, polyepitope-specific CTLs are less likely to fail as a consequence of immune escape by epitope mutation in infected cells. For EBV, EBNA1 is an immunodominant CD4+ T cell target antigen expressed in all EBV-associated malignancies and in normal EBV-infected B cells, LMP2 is immunogenic across multiple HLA types and expressed in most EBV malignancies, while BZLF1 encodes an immunodominant, immediate early lytic cycle antigen that stimulates both CD4+ and CD8+ T cells from most individuals.

Generation of Multivirus Specific CTL Using Growth Promoting Cytokines

The inventors and others have demonstrated that virus-specific CTL can efficiently and rapidly be expanded in the presence of enhancing cytokines IL-7 (10 ng/ml) and IL-4 (1,000 U/ml). These cytokines reduce activation induced cell death of antigen-specific T cells that correspondingly helps increase the frequency and repertoire of responding antigen-specific T cells compared to T cells from the same patients generated in the absence of cytokine. Further, the addition of these cytokines to our cultures produces CTL lines with negligible alloreactivity, even after a single stimulation. Thus, supplementing our CTL cultures with these cytokines, which are available as clinical grade reagents, reduces the cost of manufacture by >50%, by diminishing the time of CTL manufacture.

Generation of Multivirus Specific CTL Using an Optimized Culture Device

Currently CTLs have to be made by progressive expansion in traditional tissue-culture treated 24-well plates, with weekly restimulation. This system is extremely labor intensive, highly skilled and difficult to scale. Even though cell culture in 24-well plates requires frequent media changes and manipulation to optimize nutrient levels and removal of waste products, T cells undergo significant cell death while infection is an ever present risk for all but the most skilled tissue culture technician, since no antibiotics are used. Unfortunately, efforts to date to substitute the closed, scalable bioreactor systems that are widely used in other types of clinical cell culture systems have failed. The resultant CTL product has been either non-functional or non-specific.

The inventors utilize a new gas permeable rapid expansion device (G-Rex) that dramatically reduces T cell apoptosis during culture, resulting in more efficient expansion in vitro. Gas exchange ($O_2$ in and $CO_2$ out) occurs across a gas permeable silicon membrane at the base of the flask, preventing hypoxia while allowing a greater depth of medium above the cells, providing more nutrients and diluting waste products. These culture conditions allow the stable cell:cell interactions essential for CTL production to proceed unencumbered by physical disruptions, reducing technician time>10 fold, increasing cell output by >3 fold, and accelerating CTL manufacturing time>2 fold without affecting the phenotype or function of the CTLs (Vera et al., 2010).

Overall, by combining these three novel procedures we will be able to produce large quantities of multivirus CTL devoid of alloreactive cells using a simple one-step procedure, which will dramatically reduce cost, complexity and time associated with traditional CTL protocols.

Design Of Certain Embodiments Of The Invention

In certain aspects of the invention, the feasibility, safety and efficacy of rapidly generated trivirus-specific lines (rCTLs) in HSCT patients at risk of developing EBV, CMV or adenovirus infections or with early reactivations is evaluated.

Primary Objective and Rationale for Study Design

The primary purpose of the study is to assess the safety of administering rCTLs in transplant patients at risk of EBV, CMV, or adenovirus infection or with early reactivation or infection. We have elected to use 4 different dose levels starting with $5\times10^6$ followed by $1\times10^7$, $2\times10^7$ and a final dose of $5\times10^7$ rCTLs/m$^2$. CTLs manufactured by our previous methodology were safe at doses up to $10^8$ cells/kg (Leen et al., 2006). However as the manufacturing methodology has been modified, the inventors in some cases start at a lower dose of $5\times10^6$ cells/m$^2$ in this study. In certain cases, there is administering of additional doses (at the same level) in subjects that have a partial response after one dose or who receive other therapy that may affect the persistence or function of the infused CTL.

Patients in a feasibility/safety study are eligible following any type of allogeneic transplant to receive CTLs as prophylaxis or for early reactivations as defined herein, including, for example: 1) early treatment may be given to eligible patients with a single or multiple infections (patients with multiple infections with one reactivation and one controlled infection may be included); 2) clinical status at enrollment to allow tapering of steroids to less than 0.5 mg/kg/day prednisone; 3) negative pregnancy test in female patients if applicable (childbearing potential who have received a reduced intensity conditioning regimen); 4) prior myeoloablative or non-myeloablative allogeneic hematopoietic stem cell transplant using either bone marrow or peripheral blood stem cells within 12 months; 5) prophylaxis for patients at risk of CMV, adenovirus or EBV infection; 6) early treatment of reactivation or infection which is defined for specific embodiments for each virus as delineated:

CMV (Nichols et al., 2001; Ljungman et al., 2001)

CMV antigenemia is monitored at least weekly post transplant. Early reactivation is defined at CMV antigenemia with <10 leucocytes positive. If any patient develops CMV antigenemia (with >10 leukocytes positive) or clinical evidence of CMV infection (defined as the demonstration of CMV by biopsy specimen from visceral sites (by culture or histology) either pre or after CTL infusions, standard treatment with Ganciclovir, and/or Foscarnet and Immunoglobulins will be initiated. Patients may receive CTLs for antigenemia or elevated PCR without visceral infection.

Adenovirus

Adenovirus infection is defined as the presence of adenoviral positivity as detected by PCR or culture from ONE site such as stool or blood or urine or nasopharynx. Adenovirus disease is defined as the presence of adenoviral positivity as detected by culture from more than two sites such as stool or blood or urine or nasopharynx. In patients who meet the criteria for disease, Cidofvir may be added unless the subject could not tolerate this agent due to nephrotoxicity. Patients may receive CTLs for elevated PCR in blood or stool.

EBV

EBV-LPD is defined according to recent guidelines (Styczynski et al., 2009) as proven EBV-LPD defined by biopsy or probable EBV-LPD defined as an elevated EBV DNA level associated with clinical symptoms (adenopathy or fever or masses on imaging) but without biopsy confirmation. Patients with EBV DNA reactivation only may receive CTLs on study. Patients with proven or probable EBV-LPD should also receive Rituxan.

In certain aspects of the design, certain patients may be excluded: 1) patients receiving ATG, or Campath or other immunosuppressive T cell monoclonal antibodies within 28 days of screening for enrollment; 2) patients with other uncontrolled infections (For bacterial infections, patients must be receiving definitive therapy and have no signs of progressing infection for 72 hours prior to enrollment; for fungal infections patients must be receiving definitive systemic anti-fungal therapy and have no signs of progressing infection for 1 week prior to enrollment; progressing infection is defined as hemodynamic instability attributable to sepsis or new symptoms, worsening physical signs or radiographic findings attributable to infection. (persisting fever without other signs or symptoms will not be interpreted as progressing infection.); 3) patients who have received donor lymphocyte infusion (DLI) within 28 days; 4) patients with active acute GVHD grades II-IV; 5) active and uncontrolled relapse of malignancy Donors Donors for allogeneic (i.e. HLA matched or mismatched related or unrelated) stem cell transplants may be evaluated, including with the following: complete history and physical examination; CBC, platelets, differential; Electrolytes, BUN, creatinine, glucose, total protein, albumin, total bilirubin, alkaline phosphatase, ALT, AST, LDH, serum protein electrophoresis (if indicated); HIV-1 antibody, HIV-2 antibody, HIV NAT, HTLV-1/2 antibodies, HBsantigen, HBc antibody, HCV NAT, CMV antibody, RPR, West Nile virus NAT, and Chagas testing; ABO and Rh typing; Hemoglobin electrophoresis or Sickle Prep test (if indicated); Complete urinalysis Treatment Plan CTL Lines Trivirus specific CTL lines may be generated using a rapid protocol, using plasmid-nucleofected DCs, growth promoting cytokines and the G-Rex culture device optimized for T cell expansion, for example.

To initiate the trivirus-specific CTL line, monocyte-derived DCs are generated using plastic aherence for 2 hrs, culture in IL4+GM-CSF for 5 days and maturation for 1 day using PGE1, TNFa. After 24 hrs of maturation DCs are nucleofected with DNA plasmids expressing protective and immunogenic viral antigens of EBV, CMV and Adenovirus using the GMP compatible Lonza/AMAXA system, for example. Bicistronic plasmids are constructed that encode 1) CMV-pp65 and IE1 and 2) Adv hexon and penton, each linked by an IRES sequence. For EBV, a construct is generated encoding three EBV antigens, EBNA1, LMP2, and BZLF1. Nucleofected DCs are then used to stimulate virus specific T cell retained from the non adherent PBMC fraction, at a stimulator/responder ratio of 1:10.

To inhibit apoptosis and promote expansion of multivirus-specific T cells, the cytokines IL7 and IL4 are added in a concentration of 10 ng/ml and 1,000 U/ml respectively at the day of stimulation. T cell stimulation and expansion will take place in an optimized GMP-compatible G-Rex device which has been validated for the production of multivirus-specific T cells (Vera et al, in press).

At the end of the CTL culture period (9-12 days), the frequency of T cells specific for each virus and antigen is determined using multimer reagents, for example. To test the functional antigen specificity of the CTL one can use overlapping peptide libraries (pepmixes) spanning CMV-pp65 and IE1, Adv-hexon and penton, and EBV-EBNA1, LMP2 and BZLF1 as a stimulus in IFNg ELIspot assays. One can also use autologous and allogeneic LCLs as stimulators to measure EBV reactivity. Cytotoxicity assays are performed using recipient PHA blasts as a measure of residual alloreactiviity, and one can test antigen-specific T cell killing using LCLs either alone, or nucleofected with the three stimulating plasmids, and one can assess killing of antigen presented by shared alleles using recipient PHA blasts pulsed with pepmixes spanning pp65, IE1, Hexon, Penton, EBNA1, LMP2 and BZLF1.

The CTL lines are checked for identity, phenotype and sterility, and cryopreserved prior to administration according to SOP, in certain embodiments. Release criteria for administering the CTL to patients include viability>70%, negative culture for bacteria and fungi for at least 7 days, endotoxin testing≤5EU/ml, negative result for Mycoplasma, <2% CD83 positive cells, <10% killing of recipient PHA blasts at 20:1 ratio in Cr51 release assay and HLA identity.

Administration and Monitoring

Multivirus specific T cells are thawed and given by intravenous injection, for example. Patients may be pre-medicated with Benadryl 0.25-0.5 mg/kg (max 25 mg) IV and Tylenol 5-10 mg/kg (max 650 mg) PO. Patients may be monitored according to institutional standards for administration of blood products and at a minimum will be monitored according to below: Patients may remain on continuous pulse oximetry for at least 30 minutes, for example. Vital signs are monitored at the end of infusion then at 30 and 60 minutes. Patients may receive supportive care for acute or chronic toxicity, including blood components or antibiotics, and other intervention as appropriate. If a patient has a partial response (as defined by a 50% fall in viral load) or receives medication (such as steroids) which may affect the persistence or function of the infused CTL they are eligible to receive up to 2 additional doses at the same initial dose.

The possibility for onset of GVHD is monitored for 6 weeks following infusion. Weekly GVHD organ stage scores, overall clinical grade, biopsy information for GVHD and relevant differential diagnosis are recorded. The weekly score may encompass all information since the last assessment. Organ involvement, biopsy information, staging, differential diagnosis, and GVHD therapy are documented. Definite manifestations of Chronic GVHD include scleroderma (superficial or fasciitis), lichen planus, vitiligo, scarring alopecia, hyperkeratosis pilaris, contractures from skin immobility, nail bed dysplasia; non-infectious ulcers, corneal erosions/non-infectious conjunctivitis; Esophageal strictures, steatorrhea; Vaginal stricture, Non-septic arthritis, myositis, myasthenia, polyserositis, contractures from joint immobilization, and Bronchiolitis obliterans. Possible manifestations of chronic GVHD include eczematoid rash, dry skin, maculopapular rash, hyperpigmentation, hair loss; Xerostomia, keratoconjunctivitis sicca; Anorexia, malabsorption, weight loss, diarrhea, abdominal pain; elevation of alkaline phosphatase, transaminitis, cholangitis, hyperbilirubinemia; non-infectious vaginitis, vaginal atrophy; arthralgia; thrombocytopenia, eosinophilia, autoimmune cytopenias; bronchiolitis obliterans with organizing pneumonia, and interstitial pneumonitis. CTLs are susceptible to killing by steroids given at a dose of 1-2 mg/kg. This is standard therapy for GVHD and could also be given if a recipient develops other complications considered possibly related to CTL administration.

Primary Endpoint

The primary objectives for the phase I component are feasibility and safety. The primary endpoint for the phase II component is antiviral efficacy. Safety of administration of CTLs is 42 days for GVHD and 30 days for other toxicities. The safety endpoint will be defined as acute GvHD grades III-IV within 42 days of the last dose of CTLs or grades 3-5 infusion-related adverse events within 30 days of the last CTL dose or grades 4-5 nonhematological adverse events within 30 days of the last CTL dose and that are not due to the pre-existing infection or the original malignancy or pre-existing co-morbidities as defined by the NCI Common Terminology Criteria for Adverse Events (CTCAE), Version 4.0. Toxicities to consider include GI toxicity, renal toxicity, hemorrhagic toxicity, cardiovascular toxicity (hypotension, cardiac arrhythmia and left ventricular systolic dysfunction), neurological toxicity (somnolence and seizure), coagulation toxicity, vascular toxicity and pulmonary toxicity.

Staging and Grading of Acute GVHD

Acute GVHD grading may be performed by the consensus conference criteria (Przepiorka, et al., 1994).

Effects on Clinical Signs of Viral Infection

If a patient has organ involvement clinical response is monitored. For patients with EBV lymphoma and measurable disease, response is assessed by RECIST criteria.

Survival

Overall survival at 6 and 12 months post CTL infusion is computed.

Chronic GVHD

Chronic GVHD is assessed at 3, 6 and 12 months post CTL infusion.

Viral Reactivations

All CMV, EBV or adenovirus reactivations occurring within 3 months of CTL infusion are collected Secondary Graft Failure Secondary graft failure is defined as initial neutrophil engraftment followed by subsequent decline in the ANC to <500/mm$^3$ for three consecutive measurements on different days, unresponsive to growth factor therapy that persists for at least 14 days in the absence of a known cause such as relapse. Secondary graft failure will be assessed at 30 days post CTL infusion.

|  | Stage 0 | Stage 1 | Stage 2 | Stage 3 | Stage 4 |
|---|---|---|---|---|---|
| Skin | No rash | Rash <25% BSA | 25-50% | >50% Generalized erythroderma | Plus bullae and desquamation |
| Gut | <500 mL diarrhea/day | 501-1000 mL/day | 1001-1500 mL/day | >1500 mL/day | Severe abdominal pain & ileus |
| UGI |  | Severe nausea/vomiting |  |  |  |
| Liver | Bilirubin ≤2 mg/dl | 2.1-3 mg/dl | 3.1-6 mg/dl | 6.1-15 mg/dl | >15 mg/dl |

Grading Index of Acute GVHD*

|  | Skin | Liver | Gut | Upper GI |
|---|---|---|---|---|
| 0 | None and | None and | None and | None |
| I | Stage 1-2 and | None and | None | None |
| II | Stage 3 and/or | Stage 1 and/or | Stage 1 and/or | Stage 1 |
| III | None-Stage 3 with | Stage 2-3 or | Stage 2-4 | N/A |
| IV | Stage 4 or | Stage 4 | N/A | N/A |

Antiviral Activity

Viral load is monitored for CMV, EBV and adenovirus. For the infection under treatment response in viral load will be defined as follows:

Complete response: Return to normal range as defined by specific assay used and clinical signs and symptoms Partial response: Decrease in viral load of at least 50% from baseline or 50% improvement of clinical signs and symptoms Mixed response: Decrease in viral load of at least 50% from baseline for one infection and an increase or no change in viral load for a second infection (only applicable for patients with two infections at baseline).

Stable disease: Changes insufficient to qualify as partial response or progression Progression: Increase in viral load of at least 50% from baseline or dissemination to other sites of disease.

Reconstitution of Antiviral Immunity

Patients are monitored using ELIspot assays or multimer assays with appropriate viral specific peptide mixtures.

Patient Evaluation

Follow-Up Schedule

The Follow-up Schedule for scheduled study visits is outlined below. The timing of follow-up visits is based on the date of CTL infusion. If a patient has multiple CTL doses the schedule resets again at the beginning, so follow up relates to the last CTL dose.

FOLLOW-UP SCHEDULE

| Assessment Time | Target Day[1] (Days Post-Enrollment) |
|---|---|
| 1 week | 7 days |
| 2 weeks | 14 days |
| 3 weeks | 21 days |
| 4 weeks | 28 days |
| 5 weeks | 35 days for weekly |
| 6 weeks | 42 days |
| 8 weeks | 56 days |
| 90 days | 90 days |
| 6 months | 180 days |
| 12 months | 365 days |

[1]Target day range = ±2 days up to Week 8, and ±14 days for Days 90, 120, and ±28 days for 6 and 12 months, post-enrollment.

Assessments

All assessments are considered standard-of-care unless identified below by "*."

Pre-Infusion, assessments may include history and physical exam including height and weight; viral loads for EBV, adenovirus, CMV; complete acute GVHD staging and grading information including assessments of rash, diarrhea, nausea/vomiting, weight and liver function tests; CBC with differential, platelet count; liver function tests (bilirubin, alkaline phosphatase, AST, ALT) plus creatinine; tacrolimus/cyclosporine level if on these agents; pregnancy test if of childbearing potential and has received a reduced intensity transplant regimen; and/or samples for research laboratory studies. Post-Infusion, assessments may include viral loads for CMV, EBV, adenovirus weekly at 1, 2, 3, 4, 6 and 8 weeks, and 3 months; complete acute GVHD staging and grading information including assessments of rash, diarrhea, nausea/vomiting, weight and liver function tests weekly until Day 42; chronic GVHD evaluation (if present) 3, 6, and 12 months; CBC with differential and platelet count at 1, 2, 3, 4, 6 and 8 weeks, and 3 months; liver function tests (bilirubin, alkaline phosphatase, AST, ALT) plus creatinine at 1, 2, 3, 4, 6 and 8 weeks, and 3 months; infusion-related toxicities within 24 hours and toxicity evaluation weekly until Day 30, and acute GVHD until Day 45; steroid dose weekly until Day 42, and 3, 6 and 9 months; **samples for laboratory studies on 1, 2, 3, 4, 6 and 8 weeks, and 3 months; and/or viral reactivations through 3 months.

Research laboratory studies include assessment of virus-specific immunity based on CTL levels as measured by ELIspot or multimer assays. After the initial follow up for safety is complete at 30 days for toxicity and 42 days for GVHD, patients continue to be followed per routine clinical care post transplant. Clinical and laboratory records at 3, 6 and 12 months are assessed to evaluate for any long term effects attributable to the gene transfer component of the study.

Assessments may include one or more of the following: History and physical exam; CMV, EBV, adenovirus load; Acute GVHD evaluation; Chronic GVHD evaluation; CBC with differential, platelet count; basic chemistry (creatinine); liver function tests (alkaline phosphatase, bilirubin, AST, ALT); toxicity evaluation; steroid dose; blood and serum for ancillary laboratory studies; infections.

Upon the completion of the phase I trial, additional patients are accrued on the maximum tolerated dose (MTD) level to evaluate the clinical endpoint on antiviral activity in an early phase II study. Depending on safety data, the maximum sample size for the phase I trial is 18. Including the 6 subjects treated at the MTD dose level, an additional 10 subjects will be accrued in the early phase II study. The maximum sample size for the phase I/II study is 28 patients.

Sample Size Determination and Design Characteristics

Dose escalation is guided by the modified continual reassessment method (mCRM) to determine the MTD of rCTL (Przepiorka et al., 1995). The risk that adoptively transferred rCTL will cause GVHD is very low. The target probability of acceptable toxicity is set to be no more than 20% of eligible cases. MTD is thus defined as the dose at which the probability of dose limiting toxicity (DLT) is at most 20%. Based on previous trials, the inventors expect a shallow dose-toxicity curve. Four dose levels will be evaluated, namely, $5 \times 10^6$, $1 \times 10^7$, $2 \times 10^7$, and $5 \times 10^7$, with prior probabilities of toxicity estimated to be 3%, 5%, 10%, and 21%, respectively. In this trial, mCRM is implemented based on the exponential dose-toxicity model with a cohort of size 2. To reduce the probability of treating patients at unacceptable toxic dose levels, one can employ the modifications to the original CRM (Przepiorka et al., 1995). Specifically, there are two subject treated in each cohort, dose escalation is limited to no more than one dose level, and patient enrollment starts at the lowest dose level shown to be safe in previous studies of CTL post HSCT (Leen et al., 2009).

Depending on patient's toxicity responses at each dose level, maximum 18 patients are accrued into this Phase I trial. Two patients are initially allocated to the lowest dose level cohort and followed for 42 days post CTL infusion for evaluation of DLTs including GvHD and infusion-related toxicity. If there is one or more DLTs at the lowest dose level, the trial is stopped. Otherwise, two patients will be enrolled at the next dose level. For the intermediate dose levels, if any or both patients develop DLTs, the mCRM guides the next dose-level by estimating the toxicity probability. The dose is the same or de-escalated depending on the current estimated probability of MTD. Two more patients are recruited at the dose level recommended by the mCRM. If a previously treated dose level is selected and any of the patients develops DLTs, the trial is stopped; otherwise, two patients are enrolled at the next dose level. If none of the patients develops DLTs at the mCRM recommended dose level, two patients continue to the next dose level. The dose selection process is repeated until the MTD or the highest dose level is reached.

The final MTD is the dose level with probability closest to the targeted 20% toxicity probability. If the estimated probability of DLTs for any dose level (taking into account all patients treated at that dose level) becomes greater than 20%, the dose is de-escalated. By the dose-escalation algorithm, there are at most 2 cohorts at each dose level. The inventors do not anticipate seeing any CTL-related AE at any dose-level. Hence, upon completion of the dose escalation, all three dose-levels are safe, in certain embodiments. If this is the case, a minimum of 12 patients are treated with total six patients accrued at the MTD level. If there are one or more DLT events, the inventors expect at most 18 patients enrolled in this trial.

Simulations were performed with 10,000 replications to determine the operating characteristics of the proposed design, and the inventors compared this with a standard 3+3 dose-escalation design. The proposed design provides better estimates of the MTD based on a higher probability of declaring the appropriate dose level as the MTD, afforded smaller number of patients accrued at lower dose levels, and maintained a lower average total number of patients required for the trial. As indicated above, the first dose level is the same as that used in previous studies of CTL post HSCT and the highest dose is less than half that of the previous trail (Leen et al., 2009). In certain embodiments, there is a shallow dose-toxicity curve over the range of doses.

DLTs that occur within 42 days after initial infusion are factored into the CRM calculations to determine the recommended dose for the subsequent cohort, so the next cohort will wait until the completion of the 42 days DLT evaluation. During the study, real-time monitoring of patient toxicity outcome is performed in order to estimate the dose-toxicity curve and dose level is determined for the next patient cohort using one of the pre-specified dose levels.

After determining the MTD, additional patients are treated at the MTD level to further assess its antiviral activity. It is tested whether the rate of treatment response in viral load can be higher than 65%. The treatment response is defined as complete response, partial response and mixed response. In certain embodiments, the rCTL MTD is not effective if the response rate is lower than 30%. By a one-arm binomial sample size calculation, an additional 10 patients may be treated at the MTD level (total 16 including 6 treated at phase I trial for safety consideration). The sample size of 16 provides an exact 84.1% power to detect the hypothesized 65% rate, compared to an uninteresting rate of change of 30%, for a type-I error of 0.05. The phase I/II trial will accrue maximum 28 subjects.

B. Multiple Tumor Antigen-Specific CTLs There are a variety of mechanisms by which tumors can evade the immune system, including suppression of antigen expression, secretion of negative immunoregulatory cytokines, etc. The power of simultaneously targeting multiple tumor antigens is that it affords a strategy for overcoming and compensating for suppression of antigen expression by the tumor, such that a CTL product directed against a single antigen might not be effective if the tumor expresses low levels of that antigen, but if multiple antigens are simultaneously targeted in a single CTL product, the probability of stimulating a robust antitumor response is increased.

In specific embodiments, the present invention concerns generation of CTLs for multiple tumor antigens. Although the invention may be utilized for any cancer, including lung, breast, brain, stomach, ovarian, pancreatic, kidney, liver, bone, cervical, uterine, testicular, prostate, head and neck tumors, and so forth, in certain embodiments the invention is utilized for cancers associated with blood and bone marrow.

Hodgkin disease. Hodgkin's disease (HD) is a malignant neoplasm of lymphoreticular cell origin, characterized by the presence of large mononucleated Hodgkin (H) and giant multinucleated Reed-Sternberg (RS) cells, and collectively referred to as Hodgkin and Reed-Sternberg cells (HRS) (Anastasi et al., 1989; Harris, 1999). Approximately 7,500 new cases are diagnosed in the US annually, with the highest incidence in the 3rd decade of life. Combination chemotherapy and radiation are effective and overall survival rates are high but long-term morbidity and mortality secondary to treatment remains a significant issue. Therefore, it is desirable to develop novel therapies that improve outcomes and reduce treatment-related complications (Yazbeck et al., 2006).

Epigenetic therapy for relapsed Hodgkin disease. There is growing evidence that the pathogenesis of Hodgkin's lymphoma (HL) involves gene silencing due to aberrant epigenetic changes of gene promoter DNA hypermethylation and histone deacetylation (HDAC). These effects have been reversed in vitro by demethylating agents and HDAC inhibitors in tumor cell lines, and clinical studies using these agents have produced objective responses in relapsed HL patients (Buglio et al., 2008). The observed benefits may be due in part to induction of tumor-associated antigens (TAA) in the malignant cells, and our studies in responding subjects have shown increased activity of antigen-specific T cells directed against these newly expressed epigenetically regulated genes. Upregulated expression has been reported for several TAAs including LAGE-1, SSX-2, NYESO-1, and Survivin (Shichijo et al., 1996). In specific aspects of the invention, it is determined whether TAA-expression profiles are different in biopsies collected pre- and post-epigenetic therapy and in some cases it is assessed whether CTL directed against the expressed antigens can be generated ex vivo from Peripheral blood mononuclear cell (PBMCs) isolated pre- and post-therapy.

Adoptive immunotherapy—virus-associated malignancies. Another treatment option for patients with relapsed or refractory HL is adoptive T cell transfer. Our studies in >100 stem cell recipients have shown that donor-derived Epstein-Barr virus (EBV)—CTL lines can safely protect patients against the development of EBV-driven lymphomas and cure patients even with bulky established disease (Rooney et al., 1995; Rooney et al., 1998; Heslop et al., 1996). This approach has also shown promise for the treatment of EBV-associated tumors that arise in immunocompetent individuals (Straathof et al., 2005; Louis et al., 2008; Bollard et al., 2004; Bollard et al. 2007). In a recent phase I trial, 5 of 6 patients with relapsed EBV+ve HL or NHL who were infused with EBVILMP2-specific CTL had a tumor response, which was complete in 4. These studies combined with earlier gene-marking studies of EBV-CTL demonstrated that functional EBVILMP2-specific T cells increased in frequency in patient blood after infusion (implying expansion in vivo), homed to tumor tissues and eliminated tumor cells (Sollard et al., 2007). However, >80% of patients referred to our studies had EBV negative tumors, which has led us to investigate alternative tumor targets for CTL therapy.

Adoptive immunotherapy—virus-independent malignancies. Efforts to exploit in vitro expanded CTLs for the targeted therapy of virus independent cancer(s) in immunocompetent hosts has been hindered by (i) limited information regarding TAA expression on tumor biopsy samples, and (ii) the lack of reproducible methods to generate TAA-directed CTL lines.

Non Viral Tumor-associated antigens-Cancer testis antigens (CTA) were among the first non-viral TAA to be identified, and were initially shown to be present in melanoma (Scanlan et al., 2004; Carrel and Johnson, 1993). Subsequently many other tumors were shown to express TAAs including MAGE, SSX, NY-ESO-1, PRAME and Survivin (Mashino et al., 2001; Chambost et al., 2000; van et al., 1999; van et al., 2005; Ambrosini et al., 1997). Survivin is expressed during fetal development but is undetectable in terminally differentiated normal tissues. However, it is abundantly expressed in various tumor tissues and cell lines. Importantly, both CTA- and Survivin-specific T cells have been isolated from patients with a range of tumors and have been shown to recognize and kill tumor targets (Yee et al., 2002; Mautner et al., 2005; Tan et al., 2005). TAA expression is documented in HL and their immunogenicity and the potency of reactive CTL in vitro and in vivo are assessed.

Generation of TAA-specific CTL in vitro—EBV-transformed lymphoblastoid cell lines (LCL) and adenoviral vector transduced monocytes/DCs overexpressing viral antigens have been employed to produce polyclonal virus-specific CTL in vitro (Bollard et al., 2004; Bolard et al., 2007; Leen et al., 1997; Leen et al., 2006). However, this approach cannot be used to generate TAA-CTL, because EBV and Adv antigens are significantly more immunogenic than TAA. To date, TAA-CTL generation has required the use of single epitope peptides as a source of antigen and culture of the CTL lines in the presence of enhancing cytokines (Foster et al., 2007; Quintarelli et al., 2008). As described below, this process is optimized to allow the reproducible generation of TAA-CTL from patient PBMC using DCs expressing whole antigen (pepmix or TAA-encoding plasmids, for example) as APCs and co-culture in the presence of an optimal cytokine combination. TAA-CTL efficacy is assessed in vitro and in vivo.

In other cases wherein the invention is employed for cancer, it may be utilized for head and neck tumors. Squamous cell carcinoma (SCC), which accounts for the majority of head and neck tumors, continues to have a 5-year survival rate of 50% or less, a figure that has remained unchanged for 4 decades (Forastiere et al., 2001; Uppaluri et al., 2008). One potential means of improving treatment is based on our understanding of disease biology and uses cytotoxic T lymphocytes (CTLs) as tumor directed immunotherapy.

This approach has been successfully used to target virus-associated malignancies and our studies in immune competent patients with EBV-positive Hodgkin's disease have produced a high complete sustained remission rate even in patients with relapsed, resistant disease (Bollard et al., 2004; Bollard et al., 2007). Moreover, the anti-tumor activity of T cells targeting melanoma-associated tumor antigens has been repeatedly demonstrated (Dudley et al., 2002), and the presence of tumor infiltrating lymphocytes (TILs) in SCC tumor samples has been correlated with better clinical outcome (Wolf et al., 1987; Wolf et al., 1986; Sbrandwein-Gensler et al., 2005; Snyderman et al., 1989). In specific cases of the invention, tumor directed CTLs are employed to treat SCC of the head and neck. Several studies have confirmed that SCC tumors localized in the oropharynx and the oral cavity express several tumor-associated antigens (TAA), including MAGE1, 3, PRAME, and NY-ESO-I, which are potential T cell targets. Further, the rate of expression was generally more widespread in those with advanced stage tumors (T4-100% of analyzed samples), in whom≥2 TAA genes were commonly detected (Kienstra et al., 2003; Figueiredo et al., 2006; Ries et al., 2008; Mollaoglu et al., 2008; Marioni et al., 2005; Atanackovic et al., 2006).

Figure 13:
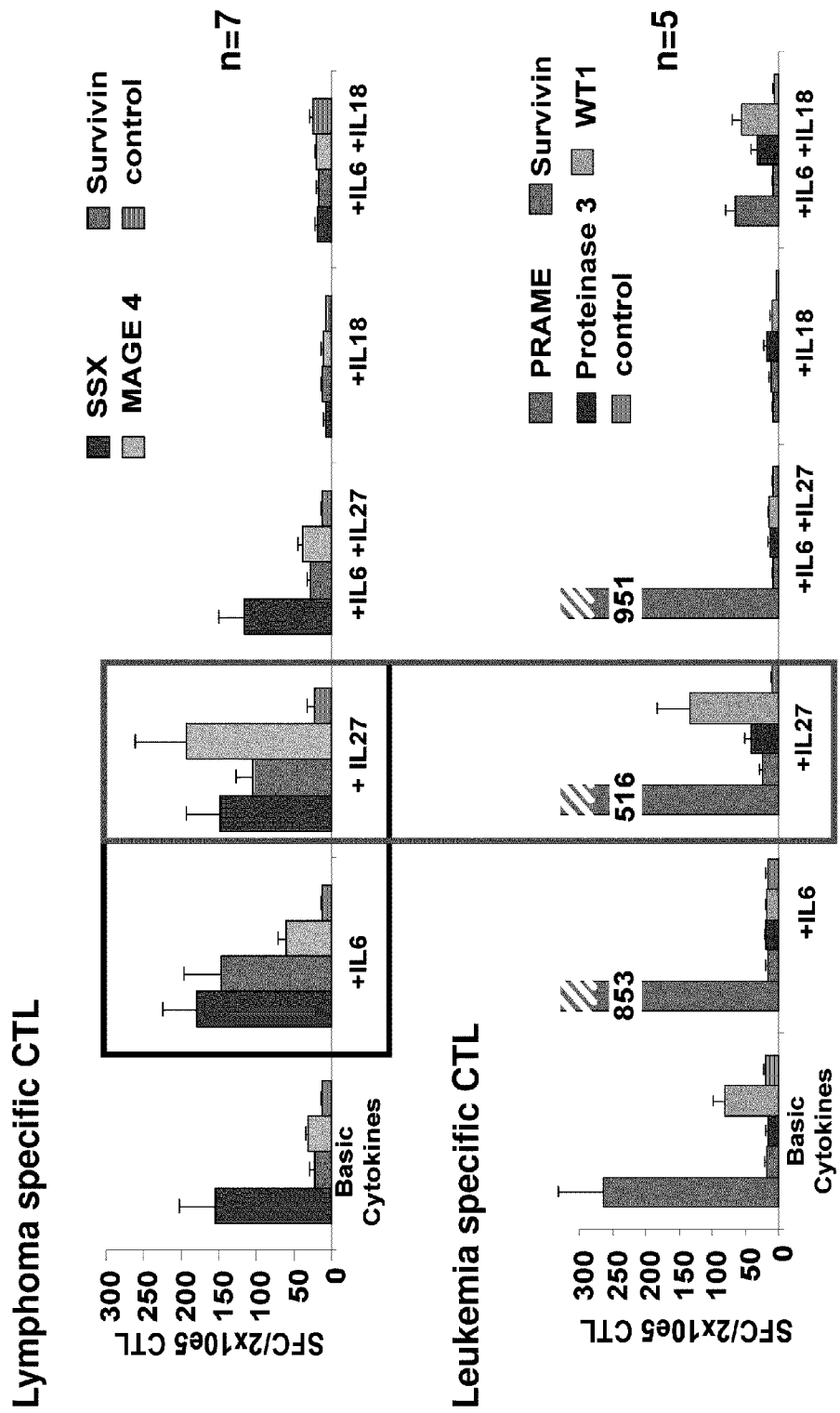
FIG. 13 demonstrates that cytokine cocktail IL7, IL12, IL15, and IL27, for example, broadens spectrum of antigen specificity in multitumor CTLs.
Figure 16:
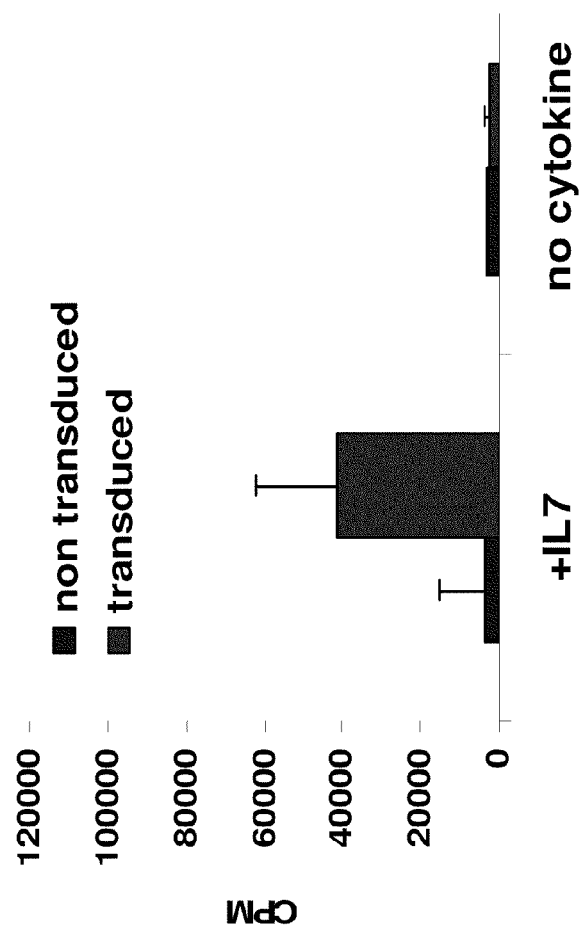
FIG. 16 demonstrates that the transgenic IL7 receptor is functional.
Figure 17:
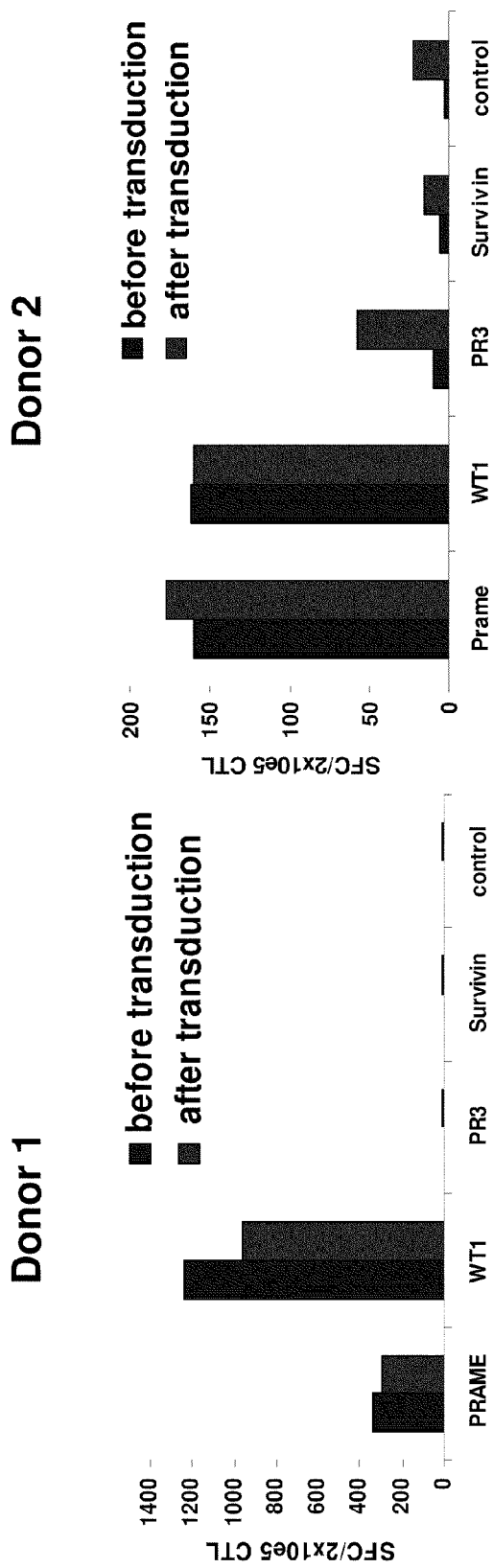
FIG. 17 demonstrates that the tumor CTL in FIG. 17 maintain antigen specificity.

Reactivated T cells may be cultured in the presence of IL-7, IL-12, IL-15, and either IL-6 or IL-27, since these cytokines have proven useful for the activation of TAA-specific CTL in vitro (FIG. 13). FIG. 14 describes CTL lines showing simultaneous specificity for two or more antigens. Such lines demonstrate specific activity against TAAs and specificity in CD4 and CD8 T cell compartment. In vivo efficiency of tumor CTLs is closely associated with in vivo persistence, and in certain aspects of the invention, antitumor CTLs can be genetically modified to enhance their in vivo survival and persistence. For example, tumor CTLs can be transduced with a transgenic IL7 receptor (FIG. 15), the transgenic IL7 receptor is functional therein (FIG. 16), and these tumor CTL maintain their antigen specificity (FIG. 17).

EXAMPLE 1

Figure 2:
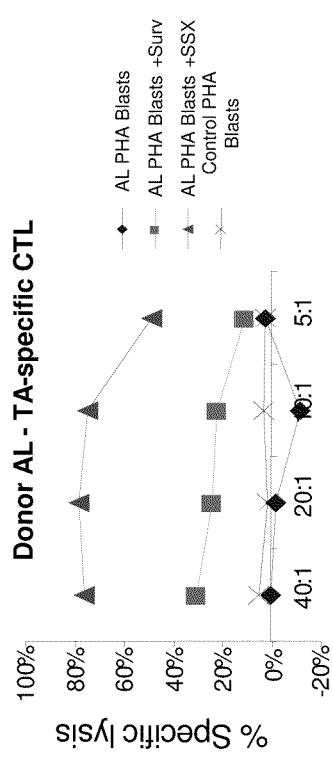
FIG. 2 shows generation of functional TA-specific CTL lines in healthy donors. TAA-CTL with specificity for Survivin and SSX were able to kill pepmix-pulsed autologous APCs in a 4 hr-chromium release assay.

Generation of TAA-Specific CTL from Healthy Donors Using PepMix-Pulsed or TAA-Expressing as APCs Production of TA-specific CTL from healthy donors. TAA pepmix-pulsed or plasmid transfected DCs were used to reactivate tumor antigen-specific T cells at a 10:1 ratio (FIG. 1A). PBMCs were cultured in the presence of IL7 (10 ng/ml), IL12 (10 ng/ml) and IL15 (10 ng/ml). A second stimulation on day 9 with plasmid transfected/pepmix-pulsed DCs with addition of IL-7 restimulates the tumor antigen-specific T cells in the culture, which are subsequently fed with IL-2 twice weekly from day 12. The specificity of the expanded TAA-CTL lines was assessed by IFN-γ ELIspot on day 16-17. Results from 2 healthy donors are shown in FIG. 2B; the left panel shows CTL specificity of a line generated using SSX2 pepmix-pulsed DCs as APCs while the right panel shows the specificity of a line generated DCs transfected with a plasmid encoding Survivin as a stimulus. To optimize the CTL generation protocol to allow the generation of CTL lines with specificity for multiple different TAAs simultaneously, different cytokine combinations were investigated. Using DCs pulsed with a mastermix of pepmixes spanning SSX2, Survivin, and MAGEA4 as APCs, and co-cultured in the presence of IL7, IL12, IL15 and IL6 (1000 U/ml), the inventors were successfully able to generate TAA-CTL with simultaneous specificity against all three of the stimulating antigens (FIG. 1C). Importantly, CTL generated from the same donor using the same source of antigens but cultured in the presence of IL7, IL12, and IL15 produced monospecific CTL directed against SSX2, thus demonstrating the importance of optimizing both antigen source and cytokine combinations for TAA-CTL generation. The multispecific CTL were functional in vitro, as shown by cytotoxicity assay (FIG. 2).

EXAMPLE 2

Exemplary Experimental Design and Methods

In some embodiments, generation of tumor-specific CTL specific for multiple lymphoma-associated target antigens is provided. One can determine whether TAA-CTL can be expanded from subjects with relapsed/refractory HL for adoptive transfer, either alone or in combination with epigenetic pharmacotherapy.

These multispecific CTL are more effective in vivo since tumor immune surveillance evasion mechanisms will be minimized, in particular aspects of the invention.

Regarding exemplary method embodiments, one can compare 2 antigen sources: (i) pepmixes (for example, 15-mers overlapping by 11 aa) spanning the TAAs and (ii) TAA-encoding DNA plasmids, and DCs are APCs for stimulation. Studies showing TAA-CTL generated from healthy donors using both antigen sources are shown in FIG. 1B. For generating multiTAA-CTL one can generate a mastermix of 3 or more pepmixes spanning the most frequently-expressed antigens or one can transfect DCs with multiple plasmids simultaneously (FIG. 1C), although in some cases one can nucleofect each plasmid separately and then pool the nucleofected DCs. Reactivated T cells are cultured in the presence of enhancing cytokines that have proven essential for the activation of TAA-specific CTL in vitro (Foster et al., 2007; Quintarelli et al., 2008). The expanded cells are restimulated on day 9 with either TAA pepmix-pulsed or transfected DCs and cultured with IL7, and twice weekly IL-2 (50 U/ml) from day 12. Specificity is assessed by IFN-γ ELIspot on d16. A schematic is shown in FIG. 1A.

In certain embodiments, TAA-CTL are readily produced from patient PBMC, particularly those collected post-epigenetic therapy (i.e. patients receiving decitabine and HDAC inhibitors, for example). A reproducible method is provided to generate polyclonal multispecific TAA-CTL, which in certain embodiments are predominantly CD8+ and contain T cells derived from both central (CD62L+) and effector memory (CD62L−) populations, and in specific aspects produce IFNγ (and other Th1 cytokines) when stimulated by cognate antigen(s).

In specific embodiments of the invention, by using an optimized cytokine combination one can sustain multispecificity within the lines, as shown in FIG. 1C. Thus, the present invention provides a reproducible technique for the manufacture of polyclonal CTL with specificity for multiple epitopes within multiple tumor antigens. These methodologies are amenable to clinical scale up, because they employ protocols that are translatable to good manufacturing practice (GMP) production.

The specificity and function of TA-specific CTL lines in vitro and in vivo may be assessed. One can measure the expansion, as well as the specificity and function, of TAA-CTL generated as described herein. In vitro-CTL expansion may be assessed, in specific cases, by weekly counting using trypan blue exclusion to ensure that one can reproducibly produce sufficient TAA-CTL for clinical use (or, for example, in a dose escalation study ($4 \times 10^7$-$2 \times 10^8$ cells/m$^2$)). Cytolytic function may be assessed by Cr$^{51}$ release assay using TAA-expressing APCs and autologous tumor as targets, for example. Cytokine producing ability may be assessed by fluorescence-activated cell sorting. Intracellular TNF-α, INF-γ, and IL-2 from both CD4+ and CD8+ T cells are measured post antigenic-stimulation. Regarding in vivo aspects, once it is established that TAA-CTL recognize and kill tumor targets in vitro, one can validate activity in a TAA-expressing xenograft model, for example. Once the anti-tumor activity of TAA-CTL is assessed as a monotherapy, one can characterize whether sequentially combining TAA-CTL with epigenetic therapy augments in vivo efficacy.

In particular embodiments of the invention, the expanded cells retain specificity and activity against all of the stimulating antigens as measured by flow cytometry, IFN-γ ELIspot, and cytolytic assays, for example, and the CTL will kill tumor targets in vitro and in vivo.

The inventors consistently achieve 20-40 fold expansion of TAA-CTL over an exemplary 16 day culture period. However, if expansion is a problem one can employ IL2 instead of IL15, which may augment proliferation without loss of antigen specificity (Quintarelli et al., 2007). In some embodiments, tumor cells may activate anti-apoptotic/survival pathways (e.g. bc1-2) and consequently be resistant to CTL killing. Should this occur, it is likely to be partial or incomplete, and one can overcome this by infusing CTL with specificity for multiple antigens rather than lines with single antigen specificity. Further, in certain embodiments combining CTL therapy with epigenetic therapy (DNA methyltransferase inhibitors and/or histone deacetylase inhibitors) can be used to enhance the antitumor response. Exemplary DNA methyltransferase inhibitors include, for example, 5-azacytidine, 5-aza-2'-deoxycytidine, 1-beta-D-arabinofuranosyl-5-azacytosine and dihydro-5-azacytidine. Exemplary HDAC inhibitors include hydroxamic acids, such as trichostatin A; cyclic tetrapeptides (such as trapoxin B), and the depsipeptides; benzamides; electrophilic ketones; and the aliphatic acid compounds such as phenylbutyrate and valproic acid.

The combination of demethylating agents with TAA-CTL offers highly targeted tumor killing with limited toxicity to bystander organs, for example, in specific embodiments of the invention. The present invention may be administered either alone or in combination with epigenetic pharmacotherapy for the treatment of cancers, including those that express tumor-associated antigens, for example hematological solid malignancies that express tumor-associated antigens.

In some embodiments of the invention, the pattern of TAA expression in SCC biopsy samples is investigated, for example to establish TAA expression in SCC biopsy samples by IRC and RT-PCR. By exemplary methods, one can analyze tumors from 3 different patient groups; i) patients with carcinoma in situ or T1, ii) T2-3, and iii) T4. Classification of these groups is independent of tumor differentiation (grading), lymph node involvement, metastasis, or location of primary tumor (oral cavity, hypopharynx, larynx, etc.) as studies have shown that TAA expression only correlates with local dissemination (Figueiredo et al., 2006; Ries et al., 2008). One can analyze 20 samples/group, for example. The expression of TAA antigens is measured (including but not limited to MAGE-I, 2, 3, 4, MAGECI, MAGEC2, SSX1, SSX2, PRAME, NY-ESO-1 and Survivin, for example) in biopsy samples using both IHC and RT-PCR. MC slides may be graded by an independent histologist using 2 criteria, in certain embodiments, (i) number of positive cells and (ii) intensity of antigen expression.

Expression is detected of at least one TAA in a majority of the patient samples, irrespective of degree of dissemination, and in certain cases for patients with T4 SCC this will increase to 100% with detection of 2 or more TAA (Figueiredo et al., 2006; Ries et al., 2008). A hierarchy is defined with respect to both frequency and intensity of TAA expression. Prior studies indicate that the majority of tumors are positive for MAGE1 or 3. PRAME has been found in approximately 40% and NY-ESO-1 in around 10% (Kienstra et al., 2003; Figueiredo et al., 2006; Ries et al., 2008; Mollaoglu et al., 2008; Marioni et al., 2005; Atanackovic et al., 2006). Those that are the most frequently expressed antigens may be utilized as stimulators for CTL generation, in certain aspects of the invention.

In specific embodiments, the profile of TAA expression in HNSCC biopsy samples is obtained, and it is addressed whether these TAA induce reactive T cells in vitro. One can generate and assess the specificity and function of tumor-specific CTL for multiple SCC-TAA. It is determined whether TAA-CTL can be expanded from subjects with SCC of the H&N for future adoptive transfer. One can first generate TAA-CTL with single antigen specificity and then one can manufacture CTL lines with specificity directed against multiple frequently-expressed TAAs. These multi-TAA-specific CTL are more effective in vivo, in specific embodiments of the invention, because they minimize tumor immune evasion mediated by antigen loss variants.

In exemplary methods, one can obtain 40-50 ml of patient blood that is a source of APCs and responder T cells. Blood may be collected from newly diagnosed patients in the same 3 groups as analyzed as described herein (T1, T2-3, T4). In specific cases, there is matching of tumor and blood from the same patients. For stimulation one can compare and also utilize two antigen sources: (i) pepmixes (for example, 15 mers overlapping by 11 aa) spanning the TAAs and (ii) TAA-encoding DNA plasmids. Patient DCs are prepared for stimulation. For generating multiTAA-CTL a mastermix is generated of 3 or more pepmixes spanning the most frequently-expressed antigens, or one can transfect DCs with multiple plasmids simultaneously (Gerdemann et al., 2009). Reactivated T cells are cultured in the presence of IL-7, IL-12, IL-15, and IL-6 in certain cases, since these cytokines have proven essential for the activation of TAA-specific CTL in vitro (Leen et al., 2007; Foster et al., 2007; Quintarelli et al., 2008).

The expanded cells may be restimulated on day 9 with either TAA pepmix-pulsed or nucleofected DCs and cultured with IL7, and twice weekly IL-2 (50 U/rnl) from day 12. CTL expansion and viability are assessed weekly, for example, by trypan blue exclusion to ensure that one can routinely produce sufficient TAA-CTL for clinical use, or for example in a dose escalation study ($4 \times 10^7$-$2 \times 10^8$ cells/m$^2$). After 3 stimulations, cytolytic function are assessed by Cr$^{51}$ release assay using TAA-expressing APCs and HLA-matched SCC cell lines, such as HSC-2, HSC-3, HNEC, BHY and HN23; 24 as targets, for example. Cytokine production is assessed by FACS. Intracellular TNF-α, INFγ, and IL-2 from both CD4+ and CD8+ T cells may be measured post antigenic-stimulation.

A reproducible method is developed to generate polyclonal multiTAA-CTL, which in some cases is predominantly CD8+ and contains both central (CD62L+) and effector memory (CD62L−) T cells and will produce IFNγ

(and other Th1 cytokines, for example) when stimulated by cognate antigen(s). The expanded CTLs retain specificity and activity against the stimulating antigens as measured by flow, IFN-γELIspot, and cytotoxicity assay(s), in particular aspects.

If not all tumor antigens are equivalently immunogenic and there is antigenic competition and loss of specificity against weaker antigens over multiple rounds of stimulation, one can use an optimized cytokine combination to sustain multispecificity within the lines. It is doubtful that there would be poor proliferation of TAA-CTL in vitro, as the inventors consistently achieve 20-40 fold expansion of TAA-CTL over a 16 day culture period. If there is a proliferation problem, one can substitute IL15 for IL2, since IL15 may augment proliferation without loss of antigen specificity (Teague et al., 2006). If the tumor cells activate anti-apoptotic/survival pathways (e.g. bcl-2) and consequently are resistant to CTL killing, it is likely to be partial or incomplete, and this would be overcome by infusing CTL with specificity for multiple antigens rather than lines with single antigen specificity, for example.

EXAMPLE 3

Administration of Tumor-Associated Antigen (TAA)-Specific Cytotoxic T-Lymphocytes to Patients With Active or Relapsed Hodgkin'S or Non-Hodgkin'S Lymphoma The present example considers exemplary embodiments for administration of TAA-specific CTLs for individuals with active or relapsed Hodgkin or non-Hodgkin lymphoma, although the skilled artisan recognizes that these practices can be applied to and/or adapted to any other types of cancer.

In certain embodiments, the present invention concerns injections (such as intravenous) of autologous or allogeneic TAA-specific CTLs in individuals with Hodgkin's (HL) or non-Hodgkin's lymphoma (NHL).
Immunotherapy Using EBV-Specific T Cells for Ebv+Ve HL and NHL EBV is associated with HL and NHL in immunocompetent patients and in these cases, the tumor cells express three of about 90 EB viral antigens. To optimize the antigenic targeting of CTLs directed against HL/NHL in immunocompetent subjects, the inventors have prepared CTLs whose specificity was directed towards the three (exemplary) expressed viral antigens by sequentially using dendritic cells (DCs) and then EBV-LCL genetically modified to overexpress LMP1 and LMP2 to reactivate and expand LMP-specific CTLs from patients or their HLA-matched allogeneic donors. The LMP antigens were expressed from an adenoviral vector. The clinical results were impressive, and 16 of 17 patients treated in remission of high-risk HD remained in remission, while 12/15 patients with active relapsed disease had tumor responses. However, >70% of the patients referred to the studies have EBV negative lymphomas and are not eligible for EBV antigen-specific T cells.
Adoptive Immunotherapy for EBV–ve HL and NHL One of the challenges of adoptive immunotherapy for non-viral cancers remains the identification of strongly immunogenic target antigens. The model tumor antigens should be specifically and universally expressed on tumor cells in order to limit collateral damage, and in some cases may be essential for the maintenance of the oncogenic phenotype of the tumor. However, the majority of antigens do not meet these criteria because they are not necessarily neo-antigens uniquely present in cancer cells but rather antigens that are also expressed in normal cells and against which peripheral blood T cells are tolerized or deleted. However antigens that are essentially tumor-specific have been identified as discussed below, but the pattern of tumor antigens expressed is highly tumor type-dependent. This underscores the importance of identifying appropriate antigens that are not expressed or poorly expressed on normal tissues and of optimizing cell culture conditions for tumor-specific CTL production, to overcome the mechanisms that establish T cell tolerance against "self" antigens.
Tumor Antigens and T Cell Immunogenicity Tumor associated antigens (TAA) can be classified into four main groups based on their expression and tissue distribution:

(I) Unique antigens (e.g. MUM1) result from single mutations that are tumor and patient specific and therefore are only expressed in neoplastic cells. They are often considered ideal for immunotherapy since tumor cells can be specifically targeted without destroying nearby normal tissue and they may be relatively strong antigens. However, because they are also usually patient-specific, the identification of the mutated gene and then the generation of an individualized CTL product targeting the identified antigen is highly labor and cost intensive.

(II) The shared lineage-restricted antigens, expressed on melanoma cells as well as their normal tissue of origin, such as MART, gp100 or Melan-A. These antigens are also strongly immunostimulatory, equivalent almost to weak viral antigens, enabling the efficient and relatively simple generation and expansion of tumor-specific T cells from healthy donors and patients with minimal in vitro manipulation. However, T cell mediated destruction of normal melanocytes has resulted in vitiligo as well as ocular and systemic autoimmunity in patients treated with melanoma-specific CTL or TILs.

(III) Shared tumor-specific TAA (e.g. the cancer testis antigens [CTA]-MAGE, BAGE, GAGE, NY-ESO-1, SSX, PRAME) are expressed in multiple tumors but not in healthy organs, with the exception of germ line tissues that are immune privileged and therefore not susceptible to T cell attack. CTAs are optimal targets for CTLs, since these can be produced on a large scale to provide broad-spectrum protection against a variety of tumors. CTAs have been targeted in both vaccine and T cell therapy protocols, with evidence of clinical efficacy.

(IV) The latter group are antigens that are overexpressed in many different tumors but expressed at low levels in healthy tissue (e.g. hTERT, CEA and Survivin). T cells targeted to these antigens carry the risk of inducing some collateral damage to normal tissues co-expressing the antigen (e.g. CEA and normal biliary epithelium), and there is limited clinical data available regarding the safety of targeting these antigens in vivo. However, Survivin- and CEA-specific T cells have been isolated from the peripheral blood of patients who have cleared their tumors, and increases in Survivin-specific T cells in patients receiving oncolytic viruses have been reported suggesting that they can have efficacy without toxicity in patients.
T Cell Immunotherapy Targeting TAAs T cell immunotherapies for non-viral tumor antigen have been described, with promising clinical results in some studies. Rosenberg and colleagues reported that infusion of melanoma-specific tumor-infiltrating lymphocytes (TILs) together with high-dose interleukin 2 (IL-2) produced clinical responses in approximately 35% of patients with metastatic melanoma. The specificity of the infused cells was not analyzed but it is likely that they targeted multiple epitopes/tumor associated antigens. More promising results were subsequently achieved using a modified treatment protocol which incorporated a lymphodepletion step prior to CTL infusion, in order to improve the expansion and persistence of adoptively-transferred cells. Ninety three patients with metastatic melanoma refractory to standard therapies received immunodepleting chemotherapy−/+total body irradiation followed by the adoptive transfer of highly selected, TIL-derived, tumor-reactive T cells and high-dose IL-2 (720,000 IU/kg q 8 h to tolerance). Fifty two of the 93 patients had objective clinical responses to treatment (39 PR, 12 CR), including regression of large bulky tumors. However, the collection of autologous TILs is not possible for most tumors. Furthermore the in vitro expansion of large numbers of tumor-specific T cells (>$10^{10}$ CTL) is a complex and expensive procedure.

The same group also infused T cell clones directed targeting a single epitope in the melanoma-associated antigen, gp100+/−IL-2 but reported poor clinical responses, with only one minor response and one mixed response, and showed that the cells failed to engraft or persist in vivo. This highlights the importance of targeting multiple epitopes/antigens to produce optimal clinical results.

Developing an Adoptive Immunotherapeutic Approach to Treat EBV−ve HL and NHL

Choosing TAA expressed in HL and NHL. The CTAs, NY-ESO-1, PRAME, MAGE-A4 and SSX2 are expressed in up to 55% of Hodgkin Reed Sternberg cells. In addition, Survivin is a good target for CTLs, which can be expanded in vitro from cancer patients and healthy donors (Pisarev et al., 2003). The expression of these tumor antigens in HL and NHL and their evident immunogenicity make them useful targets for CTL therapy. In certain embodiments of the invention, broad-spectrum antigen-specific T cells targeting multiple antigens for all patients can be generated.

As a means of stimulating T cells one can use clinically applicable peptide mixtures (pepmixes) that comprise, for example, 15 mer peptides overlapping by 11 amino acids spanning the entire sequence NY-ESO-1, SSX2, Survivin, Prame and MAGEA4. These peptide libraries encompass all possible HLA class I epitopes of each protein. The pepmixes are pooled for T cell stimulation so that T cells with specificity for multiple epitopes from all their antigens can be produced from all patients or donors, regardless of their HLA phenotype. Since the individual peptides are 15 amino acids in length, in some cases both CD4+ and CD8+ T cells are activated.

Generation of Tumor-Specific CTL Using DCs as APCs

In addition to choosing the optimal tumor antigens for T cell stimulation, the inventors have determined that dendritic cells (DCs) are the most potent antigen-presenting cells in patients, since they provide costimulation and cytokines (e.g. IL-12) which drive T cell differentiation along the appropriate effector pathway (Tc1/Th1).

Generation of TAA-Specific CTL Using Th1-Polarizing/Pro-Proliferative Cytokines

The inventors and others have shown that effective induction of cellular anti-tumor immunity also relies on immune-modulating and growth promoting cytokines. Tumor-specific T cells isolated from whole blood or tumor biopsy samples are often anergized/tolerized, with poor proliferative capabilities. To overcome this limitation and reproducibly produce tumor-specific CTL lines with multi-antigen specificity one can supplement the CTL cultures with exogenous IL-15, IL-7, IL-12 and IL-6 (in specific cases): IL-15 is common gamma chain cytokine, which overcomes T cell tolerance of tumor-specific CTL without promoting Treg growth; IL-7 improves the survival of naive, memory and activated tumor-specific T cells; IL-12, is a Th1/Tc1 polarizing cytokine that acts in an additive/synergistic manner to enhance IFN-γ production, proliferation, and cytotoxic function of antigen-specific T cells. IL-6 also benefits TAA CTL generation, as it can skew naive CD4 to Th17 T cells while preventing Treg formation.

Generation of Tumor-Specific CTL Using an Optimized Culture Device

Currently CTLs are manufactured by progressive expansion in traditional tissue-culture treated 24-well plates, using weekly restimulation with antigen expressed on antigen-presenting cells. This system is labor intensive, requires skilled technologists and is difficult to scale. Despite frequent media changes and splitting to optimize cell numbers, nutrient levels and removal of waste products, T cells undergo significant cell death during the expansion period, while the risk of infection increases with the number of plates that are manipulated. Efforts to substitute the closed, scalable bioreactor systems that are widely used in other types of clinical cell culture systems have failed for the production of antigen-specific cytotoxic T cells. The resultant T cell product has been either non-functional or non-specific.

In certain embodiments, a new gas permeable rapid expansion device (G-Rex) is employed that dramatically reduces T cell apoptosis during culture, resulting in more efficient expansion in vitro. Gas exchange ($O_2$ in and $CO_2$ out) occurs across a gas permeable silicon membrane at the base of the flask, preventing hypoxia while allowing a greater depth of medium above the cells, providing more nutrients and diluting waste products. These culture conditions allow the stable cell:cell interactions essential for CTL production to proceed unencumbered by physical disruptions, reducing technician time>10 fold, increasing cell output by >3 fold, and accelerating CTL manufacturing time>2 fold without affecting the phenotype or function of the CTLs (Vera et al., 2010).

In the event that the infusion of T cells targeting self antigens expressed in normal tissue induces an inflammatory response post-infusion one can administer steroids to effect a reversal in pulmonary symptoms, for example, thereby rapidly and effectively controlling the associated toxicity.

Patients may be included in the study described herein that have a diagnosis of Hodgkin's or non-Hodgkin's Lymphoma and that have active disease or in relapse or after autologous or syngeneic SCT or after allogeneic SCT; that have life expectancy>6 weeks; that have a Karnofsky/Lansky score of >50; that are HIV negative at time of procurement (if autologous product—patient must be HIV negative); if post allogeneic SCT must not have less than 50% donor chimerism in either peripheral blood or bone marrow; that have bilirubin<3× normal, AST<5× normal, and Hgb>8.0; that have creatinine<2× normal for age; that have been off other investigational therapy for one month prior to entry in the study; that have been off conventional therapy for at least 1 week prior to entry in this study. Patients are excluded that have severe intercurrent infection, who are HIV positive, and have GVHD>Grade II.

Exemplary Protocol

Blood Procurement for CTL and Antigen-Presenting Cell (APC) Generation

Generation of tumor-specific CTL lines requires the generation of several different components from peripheral blood mononuclear cells (PBMC). The CTL line may be derived from patient (or donor) peripheral blood T cells, by stimulation with antigen-presenting cells (APCs) pulsed with a mastermix of pepmixes (for example) spanning the exemplary tumor-associated antigens SSX2, MAGEA4, Survivin, PRAME, and NY-ESO-1 (although other tumor antigens and combinations may be employed). The initial stimulation is performed in the presence of the Th1/pro-proliiferative cytokines interleukin (IL) 7, IL-12, IL-15, and IL6 and cells will be expanded in the presence of IL-2, in particular embodiments. The APCs used to stimulate and expand the tumor-specific T cells are dendritic cells derived from patient mononuclear cells.

For CTL generation, one can either use an mononuclear cell-apheresis collection procedure (for patients with ALCs<500) or one can request a maximum blood draw of 100 ml peripheral blood×2 for a total maximum volume of 200 ml, for example. Blood may be collected from the patient or the allogeneic stem cell donor (subjects must be at least 12 kg or 24 pounds). For donors or patients<18 years a maximum of 3 mls/kg blood is taken in an 8 week period. Peripheral blood mononuclear cells (PBMC) are separated from whole blood using ficoll gradients. T cells and monocyte-derived dendritic cells (DCs) can be prepared from fresh or cryopreserved PBMC.

To initiate tumor-specific CTL lines one can make DCs by culture of PBMC-derived monocytes with cytokines (GM-CSF, IL-4) followed by maturation with a standard DC maturation cocktail (IL-1β, IL6, TNFα and PGE2, as an example). These mature dendritic cells are pulsed for 30-60 mins with a mastermix of pepmixes spanning SSX2, MAGEA4, Survivin, PRAME, and NY-ESO-1 such that the final concentration of each peptide is 50 ng/tube. Subsequently the DCs are washed once and used to stimulate PBMC-derived T cells in the presence of a T cell activating cocktail, IL-7, IL15, IL12 and IL-6 at responder:stimulator ratio of 10:1. For initiation, DCs are prepared from about 60 mL of blood and the T cells are derived from 20 to 40 mL of blood, for example.

To expand the tumor-specific T cells one can use pepmix-pulsed DCs for the second and subsequent stimulations and cells are cultured in the presence of IL-2. At least 100×10$^6$ mononuclear cells are required to generate the second batch of DCs.

At the end of the culture period, CTLs may be cryopreserved and aliquots tested for phenotype, function, specificity, identity and sterility. The frequency of tumor-specific CTLs is determined using intracellular cytokine staining, ELIspot assay, and HLA-peptide tetramers if available. Effector memory phenotype and T cell subsets are analyzed by FLOW cytometry.

Release criteria may include identity, viability>70%, negative culture for bacteria and fungi after 7 days, endotoxin testing<5EU/ml, negative result for Mycoplasma, <10% killing of patient PHA blasts or skin fibroblasts at 20:1 ratio (if an allogeneic product), <2% CD83pos/CD3neg cells and HLA identity.

One can use pepmixes (for example produced by JPT Technologies) as an antigen source. These pepmixes are overlapping peptide libraries (15 mers overlapping by 11 amino acids) spanning the entire sequence of each of the antigens of interest. Each peptide has been chemically synthesized to at least >90% purity, for example.

Administration and Monitoring

Patients are evaluated in the clinic and 2 doses of CTL are administered two weeks apart, in certain cases. Patients are monitored for clinical toxicity by the NCI Common Toxicity Criteria Scale. One can also analyze immunological parameters including phenotype and CTL frequencies by ELIspot and tetramer studies in patients who have HLA types for which tetramers are available. Functional analyses (antigen-specific cytotoxicity and cytokine release) are performed by chromium release assays and ELIspot/intracellular cytokine staining, respectively. The levels of serum cytokines before and following infusion are compared. A time period of 6 weeks, for example, will constitute the time for clinical safety monitoring. If patients have had a partial response or have stable disease they are eligible to receive up to 6 further doses of CTLs, each of which may consist of the same number as their second injection.

Treatment Plan

The following exemplary doses may be employed: $5×10^6$ cells/m$^2$; $1×10^7$ cells/m$^2$; $2×10^7$ cells/m$^2$; and $4×10^7$ cells/m$^2$.

Four exemplary dosing schedules are evaluated. Two to six patients are evaluated on each dosing schedule. This protocol is designed as a phase I study. Each patient will receive 2 injections, 14 days apart, according to the following dosing schedules:

Dose Level One:

| Day 0  | $5 \times 10^6$ cells/m$^2$ |
| Day 14 | $5 \times 10^6$ cells/m$^2$ |

Dose Level Two:

| Day 0  | $1 \times 10^7$ cells/m$^2$ |
| Day 14 | $1 \times 10^7$ cells/m$^2$ |

Dose Level Three:

| Day 0  | $2 \times 10^7$ cells/m$^2$ |
| Day 14 | $2 \times 10^7$ cells/m$^2$ |

Dose Level Four:

| Day 0  | $4 \times 10^7$ cells/m$^2$ |
| Day 14 | $4 \times 10^7$ cells/m$^2$ |

If patients with active disease have stable disease or a partial response by the RECIST criteria at their 8 week or subsequent evaluations they are eligible to receive up to 6 additional doses of CTLs at monthly intervals—each of which may consist of the same cell number as their second injection. Patients will not be able to receive additional doses until the initial safety profile is completed at 6 weeks following the second infusion.

Patient may be premedicated with Benadryl 1 mg/kg IV (max 50 mg) and Tylenol 10 mg/kg po (max 650 mg). As for cell administration, tumor-specific T cells may be given by intravenous injection over 1-10 minutes through either a peripheral or a central line. Monitoring may be undertaken according to institutional standards for administration of blood products with the exception that the injection will be given by a physician. Patients may receive supportive care for acute or chronic toxicity, including blood components or antibiotics, and other intervention as appropriate.

Patient Evaluation

The following investigations may be obtained pre-infusion, at 2, 4 and 6 weeks post-infusion and then at 3, 6, 9, and 12 months: CBC and differential, BUN, creatinine, bilirubin, SGOT, SGPT, alkaline phosphatase, Na, K, Cl, $CO_2$, albumin, and/or total protein.

Diagnostic imaging (CT scans, MRI, nuclear imaging) and/or blood tests (serum cytokines) to document measurable disease and response to therapy at pre-infusion and 6 weeks following the second infusion may be employed. If diagnostic imaging studies are performed at other times either during or after treatment on this study, that data is collected and information gained is used. If the patient receives extended dosing, imaging is done 1-3 months after the final infusion.

The following investigations may be obtained pre-infusion, 1, 2, 4 and 6 weeks post-infusion and then at 3, 6, 9, and 12 months and then yearly thereafter for 1 year. Peripheral blood in preservative free heparin and ACD (acid citrate dextrose) anticoagulant (20-40 ml). This blood may be used for phenotyping of peripheral blood T cells and analysis of specificity of CTL response using HLA-peptide tetramer analysis and immune function assays including ELIspot, intracellular cytokine staining and cytotoxicity assays.

If the patient has additional injections of cells after the first two infusions, these tests are also obtained pre each infusion, at the end of each infusion, 3-4 days post each infusion (day optional depending on patient preference), and at 1, and 2 weeks post each infusion. Follow up may then continue at 3 times monthly and may continue until 12 months after the last infusion and then yearly thereafter for 1 year. No study specific blood tests are done after two years (if the patients have had additional injections), in some cases, but one can continue to keep in contact with patients to follow long term disease responses.

In cases where the patient requires a tumor biopsy at any stage during the first year, a sample of this may be used to assess the tumor antigen expression profile. If a patients' hemoglobin is less than 8.0 g/dl at any of the evaluation times, the amount of blood drawn for the evaluation will be reduced and may be obtained over more than one venipuncture, if necessary. Monitoring parameters can include infusion tumor CTLs, CBC differential, electrolytes and liver function tests, imagin studies, phenotyping, and immune function studies, for example.

Evaluation During Study

For follow up interval, patients may be evaluated (seen in clinic or contacted by research coordinator) at two-week intervals for the first eight weeks, then at 3, 6, 9 and 12 months, then yearly for 1 year. Additional visits may be obtained as clinically indicated or if the patient is having more than 2 infusions. Regarding early termination of study and modifications of drug dosages, this study may be considered complete when 2-6 patients have been entered at each dose level in each group. Therapy for an individual patient can be terminated if a dose limiting toxicity has been observed. For the purpose of this study, dose limiting toxicity may be defined as any toxicity that is irreversible, life threatening or Grade 3-4 considered to be primarily related to the CTL injection.

Therapy for an individual patient can be terminated if a dose-limiting toxicity (DLT) has been observed. For purpose of this study, DLT is defined as: development of Grade III-IV GVHD or toxicities. The criteria listed in the NCI Common Toxicity Criteria Scale may be used in grading toxicity. GVHD may be graded by the method of Przepiorka et al. (2006). A 6-week period after the second infusion may constitute a course, which may be evaluated for critical toxicity, and a 6-week period after CTL infusion may be required for evaluation for antitumor activity. Although response is not the primary endpoint of this trial, patients with measurable disease are assessed by standard criteria. Evaluations of tumor size are performed within 2 weeks of beginning treatment and 6 weeks after the second injection. All patients who receive the first infusion are evaluable for response. Patient long term overall and progression free survival may also be evaluated at 1 year.

In patients with detectable tumors and/or lymphadenopathy—response and progression may be evaluated in this study using the international criteria proposed by the Response Evaluation Criteria in Solid Tumors (RECIST) Committee. Changes in only the largest diameter (unidimensional measurement) of the tumor lesions are used in the RECIST criteria. Measurable lesions are defined as those that can be accurately measured in at least one dimension (longest diameter to be recorded) as >20 mm with conventional techniques (CT, MRI, x-ray) or as >10 mm with spiral CT scan. The investigator may identify up to 10 measurable lesions to be followed for response. Serial measurements are to be done with CT or MRI. The same method of assessment is to be used to characterize each identified and reported lesion at baseline and during follow-up.

Complete response (CR) is defined as disappearance of all target lesions. Partial response (PR) is defined as at least a 30% decrease in the sum of the longest diameter (LD) of target lesions, taking as reference the baseline sum LD. Progressive disease (PD) is defined as at least a 20% increase in the sum of the LD of target lesions, taking as reference the smallest sum LD recorded since the treatment started or the appearance of one or more new lesions. Stable disease is defined as neither sufficient shrinkage to qualify for PR nor sufficient increase to qualify for PD, taking as reference the smallest sum LD since the treatment started. In specific embodiments of the invention, individuals may have CR or PR or stable disease.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PUBLICATIONS

Ambrosini G, Adida C, Altieri D C. A novel anti-apoptosis gene, survivin, expressed in cancer and lymphoma. Nat. Med. 1997; 3:917-921.

Anastasi J, Bitter M A, Vardiman J W. The histopathologic diagnosis and subclassification of Hodgkin's disease. Hematol Oncol Clin North Am. 1989; 3:187-204.

Atanackovic D, Blum I, Cao Y et al. Expression of cancer-testis antigens as possible targets for antigen-specific immunotherapy in head and neck squamous cell carcinoma. Cancer BioLTher. 2006; 5:1218-1225.

Boeckh M, Nichols W G, Papanicolaou G, Rubin R, Wingard J R, Zaia J. Cytomegalovirus in hematopoietic stem cell transplant recipients: Current status, known challenges, and future strategies. Biol Blood Marrow Transplant. 2003; 9:543-558.

Bollard C M, Aguilar L, Straathof K C et al. Cytotoxic T lymphocyte therapy for Epstein-Barr virus+Hodgkin's disease. J. Exp. Med. 2004; 200:1623-1633.

Bollard C M, Gottschalk S, Leen A M, Weiss H, Straathof K C, Carrum G, Khalil M, Wu M F, Huls M H, Chang C C, Gresik M Y, Gee A P, Brenner M K, Rooney C M, Heslop H E. Complete responses of relapsed lymphoma following genetic modification of tumor-antigen presenting cells and T-lymphocyte transfer. Blood. 2007; 110:2838-2845.

Bollard C M, Straathof K C, Huls M H, Leen A, Lacuesta K, Davis A, Gottschalk S, Brenner M K, Heslop H E, Rooney C M. The generation and characterization of LMP2-specific CTLs for use as adoptive transfer from patients with relapsed EBV-positive Hodgkin disease. J. Immunother. 2004; 27:317-327.

Brandwein-Gensler M, Teixeira M S, Lewis C M et al. Oral squamous cell carcinoma: histologic risk assessment, but not margin status, is strongly predictive of local disease-free and overall survival. Am. J. Surg. Pathol. 2005; 29:167-178.

Brunstein C G, Weisdorf D J, DeFor T, Barker J N, Tolar J, van Burik J A, Wagner J E. Marked increased risk of Epstein-Ban virus-related complications with the addition of antithymocyte globulin to a nonmyeloablative conditioning prior to unrelated umbilical cord blood transplantation. Blood. 2006; 108:2874-2880.

Buglio D, Georgakis G V, Hanabuchi S, Arima K, Khaskhely N M, Liu Y J, Younes A. Vorinostat inhibits STATE-mediated TH2 cytokine and TARC production and induces cell death in Hodgkin lymphoma cell lines. Blood. 2008; 112:1424-1433.

Carrel S, Johnson J P. Immunologic recognition of malignant melanoma by autologous T lymphocytes. Curr Opin Oncol. 1993; 5:383-389.

Chambost H, Van Baren N, Brasseur F, Godelaine D, Xerri L, Landi S J, Theate I, Plumas J, Spagnoli G C, Michel G, Coulie P G, Olive D. Expression of gene MAGE-A4 in Reed-Sternberg cells. Blood. 2000; 95:3530-3533.

Cobbold M, Khan N, Pourgheysari B, Tauro S, McDonald D, Osman H, Assenmacher M, Billingham L, Steward C, Crawley C, Olavarria E, Goldman J, Chakraverty R, Mahendra P, Craddock C, Moss P A. Adoptive transfer of cytomegalovirus-specific CTL to stem cell transplant patients after selection by HLA-peptide tetramers. J Exp Med. 2005; 202:379-386.

Cohen J M, Cooper N, Chakrabarti S, Thomson K, Samarasinghe S, Cubitt D, Lloyd C, Woolfrey A, Veys P, Ammolia P J. EBV-related disease following haematopoietic stem cell transplantation with reduced intensity conditioning. Leuk Lymphoma. 2007; 48:256-269.

Comoli P, Basso S, Zecca M, Pagliara D, Baldanti F, Bernardo M E, Barberi W, Moretta A, Labirio M, Paulli M, Furione M, Maccario R, Locatelli F. Preemptive therapy of EBV-related lymphoproliferative disease after pediatric haploidentical stem cell transplantation. Am J. Transplant. 2007; 7:1648-1655.

Curtis R E, Travis L B, Rowlings P A, Socie G, Kingma D W, Banks P M, Jaffe E S, Sale G E, Horowitz M M, Witherspoon R P, Shriner D A, Weisdorf D J, Kolb H J, Sullivan K M, Sobocinski K A, Gale R P, Hoover R N, Fraumeni J F, Jr., Deeg H J. Risk of lymphoproliferative disorders after bone marrow transplantation: a multi-institutional study. Blood. 1999; 94:2208-2216.

Cwynarski K, Ainsworth J, Cobbold M, Wagner S, Mahendra P, Apperley J, Goldman J, Craddock C, Moss P A. Direct visualization of cytomegalovirus-specific T-cell reconstitution after allogeneic stem cell transplantation. Blood. 2001; 97:1232-1240.

Dudley M E, Wunderlich J R, Robbins P F et al. Cancer regression and autoimmunity in patients after clonal repopulation with antitumor lymphocytes. Science 2002; 298:850-854.

Einsele H, Roosnek E, Rufer N, Sinzger C, Riegler S, Loffler J, Grigoleit U, Moris A, Rammensee H G, Kanz L, Kleihauer A, Frank F, Jahn G, Hebart H. Infusion of cytomegalovirus (CMV)-specific T cells for the treatment of CMV infection not responding to antiviral chemotherapy. Blood. 2002; 99:3916-3922.

Erdem N F, Carlson E R, Gerard D A, Ichiki A T. Characterization of 3 oral squamous cell carcinoma cell lines with different invasion and/or metastatic potentials. J. Oral Maxillofac. Surg. 2007; 65:1725-1733.

Feuchtinger T, Lucke J, Hamprecht K, Richard C, Handgretinger R, Schumm M, Greil J, Bock T, Niethammer D, Lang P. Detection of adenovirus-specific T cells in children with adenovirus infection after allogeneic stem cell transplantation. Br J Haematol. 2005; 128:503-509.

Feuchtinger T, Matthes-Martin S, Richard C, Lion T, Fuhrer M, Hamprecht K, Handgretinger R, Peters C, Schuster F R, Beck R, Schumm M, Lotfi R, Jahn G, Lang P. Safe adoptive transfer of virus-specific T-cell immunity for the treatment of systemic adenovirus infection after allogeneic stem cell transplantation. Br J Haematol. 2006; 134:64-76.

Figueiredo D L, Mamede R C, Proto-Siqueira R et al. Expression of cancer testis antigens in head and neck squamous cell carcinomas. Head Neck 2006; 28:614-619.

Forastiere A, Koch W, Trotti A, Sidransky D. Head and neck cancer. N. Engl. J. Med. 2001; 345:1890-1900.

Foster A B, Leen A M, Lee T, Okamura T, Lu A, VeraJ, J, Atkinson R, Bollard C M, Dotti G, Rooney C M. Autologous designer antigen-presenting cells by gene modification of TT lymphocyte blasts with IL-7 and IL-12. J Immunother (1997). 2007; 30:506-516.

Foster A E, Leen A M, Lee T et al. Autologous designer antigen-presenting cells by gene modification of TT lymphocyte blasts with IL-7 and IL-12. J. Immunother. 2007; 30:506-516

Gerdemann U, Christin A S, Vera J F, Ramos C A, Fujita Y, Liu H, Dilloo D, Heslop H E, Brenner M K, Rooney C M, Leen A M. Nucleofection of DCs to generate Multivirus-specific T cells for prevention or treatment of viral infections in the immunocompromised host. Mol Ther. 2009; 17:1616-1625.

Gottschalk S, Ng C Y C, Smith C A, Perez M, Sample C, Brenner M K, Heslop H E, Rooney C M. An Epstein-Barr virus deletion mutant that causes fatal lymphoproliferative disease unresponsive to virus-specific T cell therapy. Blood. 2001; 97:835-843.

Gottschalk S, Rooney C M, Heslop H E. Post-Transplant Lymphoproliferative Disorders. Annu Rev Med. 2005; 56:29-44.

Gustafsson A, Levitsky V, Zou J Z, Frisan T, Dalianis T, Ljungman P, Ringden O, Winiarski J, Ernberg I, Masucci M G. Epstein-Ban virus (EBV) load in bone marrow transplant recipients at risk to develop posttransplant lymphoproliferative disease: prophylactic infusion of EBV-specific cytotoxic T cells. Blood. 2000; 95:807-814.

Hague T, Wilkie G M, Jones M M, Higgins C D, Urquhart G, Wingate P, Burns D, McAulay K, Turner M, Bellamy C, Amlot P L, Kelly D, Macgilchrist A, Gandhi M K, Swerdlow A J, Crawford D H. Allogeneic cytotoxic T-cell therapy for EBV-positive posttransplantation lymphoproliferative disease: results of a phase 2 multicenter clinical trial. Blood. 2007; 110:1123-1131.

Harris N L. Hodgkin's lymphomas: classification, diagnosis, and grading. Semin Hematol. 1999; 36:220-232.

Heslop H E, Ng C Y C, Li C, Smith C A, Loftin S K, Krance R A, Brenner M K, Rooney C M. Long-term restoration of immunity against Epstein-Barr virus infection by adoptive transfer of gene-modified virus-specific T lymphocytes. Nature Medicine. 1996; 2:551-555.

Heslop H E, Slobod K S, Pule M A, Hale G A, Rousseau A, Smith C A, Bollard C M, Liu H, Wu M F, Rochester R J, Ammolia P J, Hurwitz J L, Brenner M K, Rooney C M. Long term outcome of EBV specific T-cell infusions to prevent or treat EBV-related lymphoproliferative disease in transplant recipients. Blood. 2009.

Kienstra M A, Neel H B, Strome S E, Roche P. Identification of NY-ESO-1, MAGE1, and MAGE-3 in head and neck squamous cell carcinoma. Head Neck 2003; 25:457-463.

Kobayashi J, Hirohashi Y, Torigoe T et al. Clonal diversity of cytotoxic T lymphocytes that recognize autologous oral squamous cell carcinoma. Hum. Immunol. 2009; 70:89-95.

Kuehnle I, Huls M H, Liu Z, Semmelmann M, Krance R A, Brenner M K, Rooney C M, Heslop H E. CD20 monoclonal antibody (rituximab) for therapy of Epstein-Barr virus lymphoma after hemopoietic stem-cell transplantation. Blood. 2000; 95:1502-1505.

Leen A M, Myers G D, Sili D, Huls M H, Weiss H, Leung K S, Carrom G, Krance R A, Chang C C, Molldrem n, Gee A P, Brenner M K, Heslop H E, Rooney C M, Bollard C M. Monoculture-derived T lymphocytes specific for multiple viruses expand and produce clinically relevant effects in immunocompromised individuals. Nat Med. 2006; 12:1160-1166.

Leen A, Ratnayake M, Foster A, Heym K, Ahmed N, Rooney C M, Gottschalk S. Contact-activated monocytes: efficient antigen presenting cells for the stimulation of antigen-specific T cells. J Immunother (1997). 2007; 30:96-107.

Leen A M, Rooney C M, Foster A E. Improving T cell therapy for cancer. Annu. Rev. Immunol. 2007; 25:243-265.

Leen A M, Christin A, Khalil M, Weiss H, Gee A P, Brenner M K, Heslop H E, Rooney C M, Bollard C M. Identification of hexon-specific CD4 and CD8 T-cell epitopes for vaccine and immunotherapy. J Virol. 2008; 82:546-554.

Leen A M, Christin A, Myers G D, Liu H, Cruz C R, Hanley P J, Kennedy-Nasser A A, Leung K S, Gee A P, Krance R A, Brenner M K, Heslop H E, Rooney C M, Bollard C M. Cytotoxic T lymphocyte therapy with donor T cells prevents and treats adenovirus and Epstein-Barr virus infections after haploidentical and matched unrelated stem cell transplant. Blood. 2009.

Ljungman P, Deliiers G L, Platzbecker U, Matthes-Martin S, Bacigalupo A, Einsele H, Ullmann J, Musso M, Trenschel R, Ribaud P, Bornhauser M, Cesaro S, Crooks B, Dekker A, Gratecos N, Klingebiel T, Tagliaferri E, Ullmann A J, Wacker P et al. Cidofovir for cytomegalovirus infection and disease in allogeneic stem cell transplant recipients. The Infectious Diseases Working Party of the European Group for Blood and Marrow Transplantation. Blood. 2001; 97:388-392.

Louis C D, Straathof K, Bollard C M, Gerken C, Huls M H, Gresik M V, Wu M F, Weiss H L, Gee A P, Brenner M K, Rooney C M, Heslop H E, Gottschalk S. Enhancing the in vivo expansion of adoptively transferred EBV-specific CTL with lymphodepleting CD45 monoclonal antibodies in NPC patients. Blood. 2008.

Louis C D, Straathof K, Bollard C M et al. Enhancing the in vivo expansion of adoptively transferred EBV-specific CTL with lymphodepleting CD45 monoclonal antibodies in NPC patients. Blood 2009; 113:2442-2450.

Marioni G, Bedogni A, Giacomelli L et al. Survivin expression is significantly higher in pN+ oral and oropharyngeal primary squamous cell carcinomas than in pN0 carcinomas. Acta Otolaryngol. 2005; 125:1218-1223.

Mashino K, Sadanaga N, Tanaka F, Yamaguchi H, Nagashima H, Inoue H, Sugimachi K, Mori M. Expression of multiple cancer-testis antigen genes in gastrointestinal and breast carcinomas. Br J Cancer. 2001; 85:713-720.

Mautner J, Jaffee E M, Pardoll D M. Tumor-specific CD4+ T cells from a patient with renal cell carcinoma recognize diverse shared antigens. Int J Cancer. 2005; 115: 752-759.

Micklethwaite K, Hansen A, Foster A, Snape E, Antonenas V, Sartor M, Shaw P, Bradstock K, Gottlieb D. Ex vivo expansion and prophylactic infusion of CMV-pp65 peptide-specific cytotoxic T-lymphocytes following allogeneic hematopoietic stem cell transplantation. Biol Blood Marrow Transplant. 2007; 13:707-714.

Mollaoglu N, Vairaktaris E, Nkenke E, Neukam F W, Ries J. Expression of MAGEA12 in oral squamous cell carcinoma. Dis. Markers. 2008; 24:27-32.

Myers G D, Krance R A, Weiss H, Kuehnle I, Demmler G, Heslop H E, Bollard C M. Adenovirus infection rates in pediatric recipients of alternate donor allogeneic bone marrow transplants receiving either antithymocyte globulin (ATG) or alemtuzumab (Campath). Bone Marrow Transplant. 2005; 36:1001-1008.

Myers G D, Bollard C M, Wu M F, Weiss H, Rooney C M, Heslop H E, Leen A M. Reconstitution of adenovirus-specific cell-mediated immunity in pediatric patients after hematopoietic stem cell transplantation. Bone Marrow Transplant. 2007; 39:677-686.

Nichols W G, Corey L, Gooley T, Drew W L, Miner R, Huang M, Davis C, Boeckh M. Rising pp65 antigenemia during preemptive anticytomegalovirus therapy after allogeneic hematopoietic stem cell transplantation: risk factors, correlation with DNA load, and outcomes. Blood. 2001; 97:867-874.

Peggs K, Verfuerth S, MacKinnon S. Induction of cytomegalovirus (CMV)-specific T-cell responses using dendritic cells pulsed with CMV antigen: a novel culture system free of live CMV virions. Blood. 2001; 97:994-1000.

Peggs K S, Verfuerth S, Pizzey A, Khan N, Guiver M, Moss P A, MacKinnon S. Adoptive cellular therapy for early cytomegalovirus infection after allogeneic stem-cell transplantation with virus-specific T-cell lines. Lancet. 2003; 362:1375-1377.

Przepiorka D, Weisdorf D, Martin P, Klingemann H G, Beatty P, Hows J, Thomas E D. 1994 Consensus Conference on Acute GVHD Grading. Bone Marrow Transplant. 1995; 15:825-828.

Quintarelli C, Vera J F, Savoldo B, Giordano Attianese G M, Pule M, Foster A E, Heslop H E, Rooney C M, Brenner M K, Dotti G. Co-expression of cytokine and suicide genes to enhance the activity and safety of tumor-specific cytotoxic T lymphocytes. Blood. 2007; 110:2793-2802.

Quintarelli C, Dotti G, De A B, Hoyos V, Mims M, Luciano L, Heslop H E, Rooney C M, Pane F, Savoldo B. Cytotoxic T lymphocytes directed to the preferentially expressed antigen of melanoma (PRAME) target chronic myeloid leukemia. Blood. 2008; 112:1876-1885.

Ries J, Vairaktaris E, Mollaoglu N et al. Expression of melanoma-associated antigens in oral squamous cell carcinoma. J. Oral Pathol. Med. 2008; 37:88-93.

Rooney C M, Smith C A, Ng C, Loftin S K, Li C, Krance R A, Brenner M K, Heslop H E. Use of gene-modified virus-specific T lymphocytes to control Epstein-Barr virus-related lymphoproliferation. Lancet. 1995; 345:9-13.

Rooney C M, Smith C A, Ng C Y, Loftin S K, Sixbey J W, Gan Y, Srivastava D K, Bowman L C, Krance R A, Brenner M K, Heslop H E. Infusion of cytotoxic T cells for the prevention and treatment of Epstein-Barr virus-induced lymphoma in allogeneic transplant recipients. Blood. 1998; 92:1549-1555.

Scanlan M J, Simpson A J, Old L J. The cancer/testis genes: review, standardization, and commentary. Cancer Immun. 2004; 4:1.

Shichijo S, Yamada A, Sagawa K, Iwamoto O, Sakata M, Nagai K, Itoh K. Induction of MAGE genes in lymphoid cells by the demethylating agent 5-aza-2'-deoxycytidine. Jpn J Cancer Res. 1996; 87:751-756.

Snyderman C H, Heo D S, Chen K, Whiteside T L, Johnson J T. T-cell markers in tumor-infiltrating lymphocytes of head and neck cancer. Head Neck 1989; 11:331-336.

Straathof K C, Bollard C M, Popat D, Huls M H, Lopez T, Morriss M C, Gresik M V, Gee A P, Russell H V, Brenner M K, Rooney C M, Heslop H E. Treatment of nasopharyngeal carcinoma with Epstein-Barr virus—specific T lymphocytes. Blood. 2005; 105:1898-1904.

Styczynski J, Reusser P, Einsele H, de la CR, Cordonnier C, Ward K N, Ljungman P, Engelhard D. Management of HSV, VZV and EBV infections in patients with hematological malignancies and after SCT: guidelines from the Second European Conference on Infections in Leukemia. Bone Marrow Transplant. 2009; 43:757-770.

Tang J, Flomenberg P, Harshyne L, Kenyon L, Andrews D W. Glioblastoma patients exhibit circulating tumorspecific CD8+ T cells. Clin Cancer Res. 2005; 11:5292-5299.

Teague R M, Sather B D, Sacks J A, Huang M Z, Dossett M L, et al. Interleukin-15 rescues tolerant CD8+ T cells for use in adoptive immunotherapy of established tumors. Nat Med. 2006; 12:335-341.

Uppaluri R, Dunn G P, Lewis J S, Jr. Focus on TILs: prognostic significance of tumor infiltrating lymphocytes in head and neck cancers. Cancer Immun. 2008; 8:16.

van BN, Brasseur F, Godelaine D, Hames G, Ferrant A, Lehmann F, Andre M, Ravoet C, Doyen C, Spagnoli G C, Bakkus M, Thielemans K, Boon T. Genes encoding tumor-specific antigens are expressed in human myeloma cells. Blood. 1999; 94:1156-1164.

van RF, Szmania S M, Zhan F, Gupta S K, Pomtree M, Lin P, Batchu R B, Moreno A, Spagnoli G, Shaughnessy J, Tricot G. NY-ESO-1 is highly expressed in poor-prognosis multiple myeloma and induces spontaneous humoral and cellular immune responses. Blood. 2005; 105:3939-3944.

Vera J, Savoldo B, Vigouroux S, Biagi E, Pule M, Rossig C, Wu J, Heslop H E, Rooney C M, Brenner M K, Dotti G. T lymphocytes redirected against the kappa light chain of human immunoglobulin efficiently kill mature B lymphocytederived malignant cells. Blood. 2006; 108:3890-3897.

Walter E A, Greenberg P D, Gilbert M J, Finch R J, Watanabe K S, Thomas E D, Riddell S R. Reconstitution of cellular immunity against cytomegalovirus in recipients of allogeneic bone marrow by transfer of T-cell clones from the donor. N Engl J Med. 1995; 333:1038-1044.

Wolf G T, Hudson J L, Peterson K A, Miller H L, McClatchey K D. Lymphocyte subpopulations infiltrating squamous carcinomas of the head and neck: correlations with extent of tumor and prognosis. Otolaryngol. Head Neck Surg. 1986; 95:142-152.

Wolf G T, Schmaltz S, Hudson J et al. Alterations in T-lymphocyte subpopulations in patients with head and neck cancer. Correlations with prognosis. Arch. Otolaryngol. Head Neck Surg. 1987; 113:1200-1206.

Yazbeck V, Georgakis G V, Wedgwood A, Younes A. Hodgkin's lymphoma: molecular targets and novel treatment strategies. Future Oncol. 2006; 2:533-551.

Yee C, Thompson J A, Byrd D, Riddell S R, Roche P, Celis E, Greenberg P D. Adoptive T cell therapy using antigenspecific CD8+ T cell clones for the treatment of patients with metastatic melanoma: in vivo persistence, migration, and antitumor effect of transferred T cells. Proc Natl Acad Sci D S A. 2002; 99:16168-16173.

Young L S, Rickinson A B. Epstein-Barr virus: 40 years on. Nat Rev Cancer. 2004; 4:757-768.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of generating cytotoxic T-lymphocytes (CTLs) that target at least one antigen from two or more viruses, comprising the steps of:
    contacting a population of dendritic cells (DCs) from an individual with more than one library of peptides, which combine to represent at least two different antigens and at least two different viruses, wherein the peptides in each library overlap in sequence to span at least a part of a viral antigen, thereby producing a population of DCs that present at least one epitope from at least two different viruses, wherein the produced DCs present at least one epitope through major histocompatibility complex (MHC) class I and present at least one epitope through MHC class II;
    contacting peripheral blood mononuclear cells (PBMCs) from the individual with the produced DCs, wherein the PBMCs comprise antigen-specific T lymphocytes that recognize at least one said epitope from at least two different viruses; and
    culturing the antigen-specific T lymphocytes in medium in a vessel, wherein the medium comprises one or more cytokines, to produce cytotoxic T-lymphocytes (CTLs) that target at least one antigen from two or more viruses.

2. The method of claim 1, wherein the CTLs are administered to an immunocompromised individual.

3. The method of claim 2, wherein the individual has had an allogeneic stem cell transplant.

4. The method of claim 2, wherein the cells are administered by injection.

5. The method of claim 4, wherein the injection is intravenous.

6. The method of claim 1, wherein the cytokines comprise IL-4 and/or IL-7.

7. The method of claim 1, wherein the vessel comprises a gas permeable membrane.

8. The method of claim 1, wherein the produced DCs present at least one epitope from one antigen of one virus and at least one epitope from a different antigen of the same virus.

9. The method of claim 1, wherein at least one epitope is from an adenovirus antigen.

10. The method of claim 9, wherein at least one epitope is from the hexon antigen and at least one epitope is from the penton antigen.

11. A method of expanding the quantity of antigen specific T-lymphocytes that target at least one antigen from two or more viruses, comprising the steps of:
contacting a population of DCs from an individual with more than one library of peptides, which combine to represent at least two different antigens and at least two different viruses, wherein the peptides in each library overlap in sequence to span at least a part of a viral antigen, thereby producing a population of DCs that present at least one epitope from at least two different viruses; and
contacting PBMCs from the individual with the produced DCs, wherein the PBMCs comprise antigen-specific T lymphocytes that recognize said at least one epitope from at least two different viruses; and
culturing the antigen-specific T lymphocytes in medium in a vessel, wherein the medium comprises one or more cytokines, to increase the quantity of T-lymphocytes that target at least one antigen from two or more viruses, wherein the T lymphocytes comprise CD4 + T-lymphocytes and CD8+ T-lymphocytes.

12. The method of claim 11, wherein the cytokines comprise IL-4 and/or IL-7.

13. The method of claim 11, wherein the vessel comprises a gas permeable membrane.

14. The method of claim 11, wherein the produced DCs present at least one epitope from one antigen of one virus and at least one epitope from a different antigen of the same virus.

15. The method of claim 11, wherein at least one epitope is from an adenovirus antigen.

16. The method of claim 15, wherein at least one epitope is from the hexon antigen and at least one epitope is from the penton antigen.

17. A method of generating cytotoxic T-lymphocytes that target at least one antigen from two or more viruses, comprising the steps of:
nucleofecting DCs from an individual with plasmids that encode at least one epitope from at least two antigens and at least two viruses, thereby producing a population of DCs that present at least one epitope from at least two different antigens and at least two different viruses; wherein the nucleofected DCs present at least one epitope through major histocompatibility complex (MHC) class I and present at least one epitope through MHC class II; and
contacting PBMCs from the individual with the produced population of DCs, wherein the PBMCs comprise antigen-specific T lymphocytes that recognize said at least one epitope from at least two different viruses; and
culturing the antigen-specific T lymphocytes in medium in a vessel, wherein the medium comprises one or more cytokines, to produce cytotoxic T-lymphocytes that target at least one antigen from two or more viruses.

18. The method of claim 17, wherein the cytokines comprise IL-4 and/or IL-7.

19. The method of claim 17, wherein the vessel comprises a gas permeable membrane.

20. The method of claim 17, wherein the produced population of DCs present at least one epitope from one antigen of one virus and at least one epitope from a different antigen of the same virus.

21. The method of claim 17, wherein at least one epitope is from an adenovirus antigen.

22. The method of claim 21, wherein at least one epitope is from the hexon antigen and at least one epitope is from the penton antigen.

23. A method of expanding the quantity of antigen specific T-lymphocytes that target at least one antigen from two or more viruses, comprising the steps of:
nucleofecting DCs from an individual with plasmids that encode at least one epitope from at least two antigens and at least two viruses, thereby producing a population of DCs that present at least one epitope from at least two different antigens and at least two different viruses; and
contacting PBMCs from the individual with the produced population of DCs, wherein the PBMCs comprise antigen-specific T lymphocytes that recognize said at least one epitope from at least two different viruses; and
culturing the antigen-specific T lymphocytes in medium in a vessel, wherein the medium comprises one or more cytokines, to increase the quantity of T-lymphocytes that target at least one antigen from two or more viruses, wherein the T lymphocytes comprise CD4+ T-lymphocytes and CD8+ T-lymphocytes.

24. The method of claim 23, wherein the cytokines comprise IL-4 and/or IL-7.

25. The method of claim 23, wherein the vessel comprises a gas permeable membrane.

26. The method of claim 23, wherein the produced population of DCs present at least one epitope from one antigen of one virus and at least one epitope from a different antigen of the same virus.

27. The method of claim 23, wherein at least one epitope is from an adenovirus antigen.

28. The method of claim 27, wherein at least one epitope is from the hexon antigen and at least one epitope is from the penton antigen.

* * * * *